US012570967B2

(12) United States Patent
Lee et al.

(10) Patent No.: US 12,570,967 B2
(45) Date of Patent: Mar. 10, 2026

(54) SERINE PROTEASE VARIANT

(71) Applicant: CJ CHEILJEDANG CORPORATION, Seoul (KR)

(72) Inventors: Joo Hee Lee, Seoul (KR); A-Ra Cho, Seoul (KR); Chang Jun Ji, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 584 days.

(21) Appl. No.: 17/997,455

(22) PCT Filed: Mar. 11, 2022

(86) PCT No.: PCT/KR2022/003415
§ 371 (c)(1),
(2) Date: Oct. 28, 2022

(87) PCT Pub. No.: WO2022/191563
PCT Pub. Date: Sep. 15, 2022

(65) Prior Publication Data
US 2023/0174964 A1 Jun. 8, 2023

(30) Foreign Application Priority Data

Mar. 12, 2021 (KR) ........................ 10-2021-0032885

(51) Int. Cl.
*C12N 9/52* (2006.01)

(52) U.S. Cl.
CPC .............. *C12N 9/52* (2013.01); *C12Y 304/21* (2013.01)

(58) Field of Classification Search
CPC ................................ C12N 9/52; C12Y 304/21
See application file for complete search history.

(56) References Cited

U.S. PATENT DOCUMENTS

| | | | |
|---|---|---|---|
| 7,618,801 B2 | 11/2009 | Jones et al. | |
| 8,535,927 B1 | 9/2013 | Jones et al. | |
| 9,441,215 B2 | 9/2016 | Olinski et al. | |
| 9,801,398 B2 | 10/2017 | Olinski et al. | |
| 10,619,177 B2 | 4/2020 | Lynglev | |
| 2003/0073222 A1 | 4/2003 | Poulose et al. | |
| 2009/0111161 A1* | 4/2009 | Jones .................... | C11D 3/386 |
| | | | 435/252.35 |
| 2015/0344860 A1 | 12/2015 | Olinski et al. | |
| 2018/0340191 A1 | 11/2018 | Kreel et al. | |

FOREIGN PATENT DOCUMENTS

| | | |
|---|---|---|
| EP | 2 589 651 A2 | 5/2013 |
| EP | 4 053 272 A1 | 9/2022 |
| KR | 10-2005-0068750 A | 7/2005 |
| KR | 10-2009-0129425 A | 12/2009 |
| KR | 10-2014-0136033 A | 11/2014 |
| KR | 10-2019-0086540 A | 7/2019 |
| WO | 2009/058679 A1 | 5/2009 |
| WO | 2014/209789 A1 | 12/2014 |
| WO | 2018/015304 A1 | 1/2018 |
| WO | WO-2018118815 A1 * | 6/2018 ................ A23J 3/34 |

OTHER PUBLICATIONS

Edelman et al. 2001 (Degeneracy and complexity in biological systems; PNAS 98(24): 13763-13768). (Year: 2001).*
Database Uniprot, A0A3NIATLO, 2 pages, Feb. 13, 2019.
NCBI Reference Sequence WP_067965505 Apr. 17, 2020, S1 family peptidase [*Noracardiopsis trehalose*], 1 page, (Apr. 17, 2020).
NCBI Reference Sequence WP_078763344 Apr. 1, 2020, S1 family peptidase [*Marinactinospora thermotolerans*], 1 page, (Apr. 17, 2020).
Database UniProtKB/TrEMBL Accession No. A0A4P6QAJ7, 2 pages (Feb. 10, 2021).
Database UniProtKB/TrEMBL, Accession No. A0A3N1ATL0, 2 pages (Aug. 12, 2020).
Database UniProtKB/TrEMBL, Accession No. A0A368T194, 2 pages (Aug. 12, 2020).
Barrett, "Cathepsin G," *Methods in Enzymology* 80:561-565 (1981).
Hedstrom, "Serine Protease Mechanism and Specificity," *Chem. Rev.* 102:4501-4523 (2002).
NCBI Reference Sequence: WP_067965505.1, 1 page (Apr. 17, 2020).
Kim et al., "Expression and characterization of a thermostable serine protease (TfpA) from *Thermomonospora fusca* YX in *Pichia pastoris*, " *Appl Microbiol Biotechnol* 68:355-359 (2005).
Kelch et al., "Mesophile versus Thermophile: Insights Into the Structural Mechanisms of Kinetic Stability," *J. Mol. Biol.* 370:784-795 (2007).
U.S. Appl. No. 17/780,239, filed May 26, 2022.

* cited by examiner

*Primary Examiner* — Mary Maille Lyons
(74) *Attorney, Agent, or Firm* — Seed Intellectual Property Law Group LLP

(57) ABSTRACT

The present disclosure relates to a novel serine protease variant.

18 Claims, 1 Drawing Sheet
Specification includes a Sequence Listing.

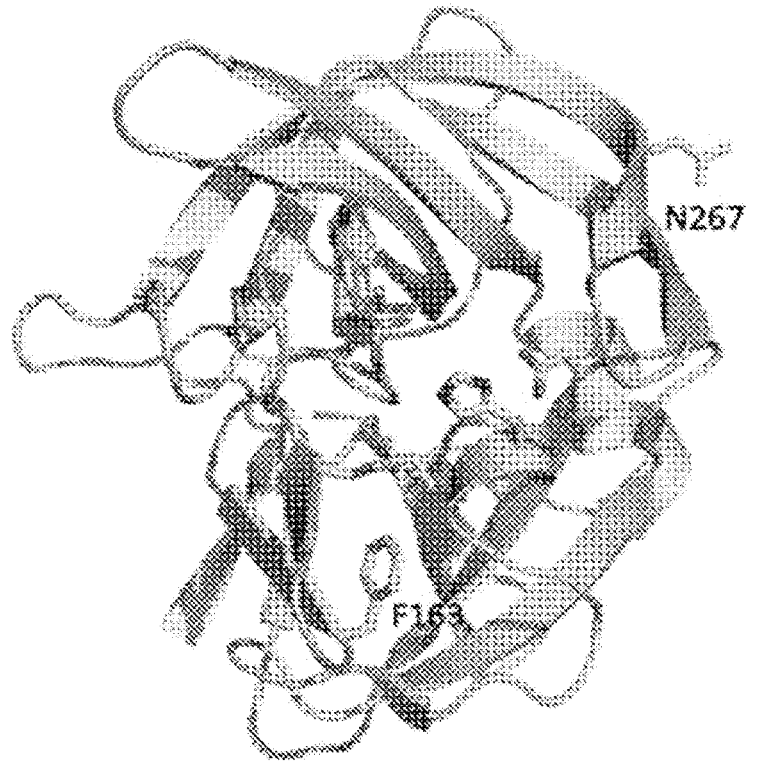

SEQUENCE LISTING

```
<160> NUMBER OF SEQ ID NOS: 72

<210> SEQ ID NO 1
<211> LENGTH: 6922
<212> TYPE: DNA
<213> ORGANISM: Artificial sequence
<220> FEATURE:
<223> OTHER INFORMATION: Synthetic nucleotide sequence - pBE-S-TFP

<400> SEQUENCE: 1
actagtgttc ttttctgtat gaaaatagtt atttcgagtc tctacggaaa tagcgagaga        60
tgatatacct aaatagagat aaaatcatct caaaaaaatg ggtctactaa aatattattc       120
catctattac aataaattca cagaatagtc ttttaagtaa gtctactctg aacttaagca       180
aaaggagagg gacgcgtgtg agaagcaaaa aattgtggat cagcttgttg tttgcgttaa       240
cgttaatctt tacgatggcg ttcagcaaca tgtctgcgca ggctgcggcc ggtgcacata       300
tgcaagagct ggcgttgaaa cgggacctcg gcctctctga cgcagaagta gccgaactcc       360
gggctgctga ggcggaagcg gtcgagctcg aggaggagct ccgcgattca ttagggtcag       420
acttcggcgg tgtatatctg gatgctgaca ccaccgaaat tacggtcgcg gtaaccgacc       480
```

-continued

```
cggcagcggt aagtcgtgtc gacgcggatg atgtcacagt tgatgttgtc gatttcgggg    540
aaacagcttt gaatgatttt gtggcttcat taaatgccat tgccgacacg gcagaccta    600 aagtcactgg atggtatacc gatctcgaaa gtgatgccgt agtcattacg accttgcgtg    660
gcgggactcc tgctgccgag gaacttgctg agagagcggg tctcgacgaa agagccgttc    720
ggattgtgga agaagatgaa gaaccacaga gcttggctgc aattattggt ggaaacccgt    780
actatttcgg aaattacaga tgcagtatcg ggtttagtgt ccgtcagggc tctcaaacgg    840
gattcgcgac cgcaggccac tgcggatcca cggggacgcg tgtgtcttct ccttcaggaa    900
cagttgcagg aagttatttc ccgggtcgcg atatgggctg ggtgcggatt acatcagcag    960
atactgtaac accactcgta aatcggtata atgggggaac tgttacggtc actgggtcac    1020
aagaagctgc caccggatcc tccgtttgtc gctctggagc aacaacgggc tggcgctgcg    1080
gaactatcca atcaaaaaac caaacggttc gctatgcaga agggactgtt actggtttaa    1140
caagaactac agcctgtgct gaaggtgggg attctggagg gccatggctc acaggtagcc    1200
aggcgcaagg ggttacaagc ggcggaacag gcgattgcag aagtggaggg attacctttt    1260
tccaaccaat caatccattg cttagctatt tcggccttca attagtgacc ggctgaaagc    1320
ttgtcgacct gcagtctaga catcaccatc atcaccacta atgcggtagt ttatcacagt    1380
taaattgcta acgcagtcag gcaccgtgta tgaaatctaa caatgcgctc atcgtcatcc    1440
tcggcaccgt caccctggat gctgtaggca taggcttggt tatgccggta ctgccgggcc    1500
tatttcactt tttgcattct acaaactgca taactattat gtaaatcgct ccttttagg    1560 tggcacaaat gtgaggcatt ttcgctcttt ccggcaacca cttccaagta aagtataaca    1620
cactatactt tatattcata aagtgtgtgc tctgcgaggc tgtcggcagt gccgaccaaa    1680
accataaaac ctttaagacc tttctttttt ttacgagaaa aaagaaacaa aaaaacctgc    1740
cctctgccac ctcagcaaag ggggttttg ctctcgtgct cgtttaaaaa tcagcaaggg    1800
acaggtagta ttttttgaga agatcactca aaaaatctcc acctttaaac ccttgccaat    1860
ttttattttg tccgttttgt ctagcttacc gaaagccaga ctcagcaaga ataaaatttt    1920
tattgtcttt cggtttttcta gtgtaacgga caaaaccact caaaataaaa aagatacaag    1980
agaggtctct cgtatctttt attcagcaat cgcgcccgat tgctgaacag attaataata    2040
gattttagct ttttatttgt tgaaaaaagc taatcaaatt gttgtcggga tcaattactg    2100
caaagtctcg ttcatcccac cactgatctt ttaatgatgt attggggtgc aaaatgccca    2160
aaggcttaat atgttgatat aattcatcaa ttccctctac ttcaatgcgg caactagcag    2220
taccagcaat aaacgactcc gcacctgtac aaaccggtga atcattacta cgagagcgcc    2280
agccttcatc acttgcctcc catagatgaa tccgaacctc attacacatt agaactgcga    2340
atccatcttc atggtgaacc aaagtgaaac ctagtttatc gcaataaaaa cctatactct    2400
ttttaatatc cccgactggc aatgccggga tagactgtaa cattctcacg cataaaatcc    2460
cctttcattt tctaatgtaa atctattacc ttattattaa ttcaattcgc tcataattaa    2520
tcctttttct tattacgcaa aatggcccga tttaagcaca ccctttattc cgttaatgcg    2580
ccatgacagc catgataatt actaatacta ggagaagtta ataaatacga gcaaaaggcc    2640
agcaaaaggc caggaaccgt aaaaaggccg cgttgctggc gtttttccat aggctccgcc    2700
cccctgacga gcatcacaaa aatcgacgct caagtcagag gtggcgaaac ccgacaggac    2760
tataaagata ccaggcgttt cccccctggaa gctccctcgt gcgctctcct gttccgaccc    2820
```

```
tgccgcttac cggatacctg tccgcctttc tcccttcggg aagcgtggcg ctttctcata    2880
gctcacgctg taggtatctc agttcggtgt aggtcgttcg ctccaagctg ggctgtgtgc    2940 acgaacccce cgttcagccc gaccgctgcg ccttatccgg taactatcgt cttgagtcca    3000
acccggtaag acacgactta tcgccactgg cagcagccac tggtaacagg attagcagag    3060
cgaggtatgt aggcggtgct acagagttct tgaagtggtg gcctaactac ggctacacta    3120
gaagaacagt atttggtatc tgcgctctgc tgaagccagt taccttcgga aaaagagttg    3180
gtagctcttg atccggcaaa caaaccaccg ctggtagcgg tggtttttttt gtttgcaagc    3240 agcagattac gcgcagaaaa aaaggatctc aagaagatcc tttgatcttt tctacggggt    3300
ctgacgctca gtggaacgaa aactcacgtt aagggatttt ggtcatgaga ttatcaaaaa    3360
ggatcttcac ctagatcctt ttaaattaaa aatgaagttt taaatcaatc taaagtatat    3420
atgagtaaac ttggtctgac agttaccaat gcttaatcag tgaggcacct atctcagcga    3480
tctgtctatt tcgttcatcc atagttgcct gactccccgt cgtgtagata actacgatac    3540
gggagggctt accatctggc cccagtgctg caatgatacc gcgagaccca cgctcaccgg    3600
ctccagattt atcagcaata aaccagccag ccggaagggc cgagcgcaga agtggtcctg    3660
caactttatc cgcctccatc cagtctatta attgttgccg ggaagctaga gtaagtagtt    3720
cgccagttaa tagtttgcgc aacgttgttg ccattgctac aggcatcgtg gtgtcacgct    3780
cgtcgtttgg tatggcttca ttcagctccg gttcccaacg atcaaggcga gttacatgat    3840
cccccatgtt gtgcaaaaaa gcggttagct ccttcggtcc tccgatcgtt gtcagaagta    3900
agttggccgc agtgttatca ctcatggtta tggcagcact gcataattct cttactgtca    3960
tgccatccgt aagatgcttt tctgtgactg gtgagtactc aaccaagtca ttctgagaat    4020
agtgtatgcg gcgaccgagt tgctcttgcc cggcgtcaat acgggataat accgcgccac    4080
atagcagaac tttaaaagtg ctcatcattg gaaaacgttc ttcggggcga aaactctcaa    4140
ggatcttacc gctgttgaga tccagttcga tgtaacccac tcgtgcaccc aactgatctt    4200
cagcatcttt tactttcacc agcgtttctg ggtgagcaaa aacaggaagg caaaatgccg    4260
caaaaaaggg aataagggcg acacggaaat gttgaatact catactcttc ctttttcaat    4320
attattgaag catttatcag ggttattgtc tcatgagcgg atacatattt gaatgtattt    4380
agaaaaataa acaaataggg gttccgcgca catttccccg aaaagtgcca cctgacgtct    4440
aagaaaccat tattatcatg acattaacct ataaaaatag gcgtatcacg aggccctttc    4500
gtctcgcgcg tttcggtgat gacggtgaaa acctctgaca gtaaccaaca tgattaacaa    4560
ttattagagg tcatcgttca aaatggtatg cgttttgaca catccactat atatccgtgt    4620
cgttctgtcc actcctgaat cccattccag aaattctcta gcgattccag aagtttctca    4680
gagtcggaaa gttgaccaga cattacgaac tggcacagat ggtcataacc tgaaggaaga    4740
tctgattgct taactgcttc agttaagacc gaagcgctcg tcgtataaca gatgcgatga    4800
tgcagaccaa tcaacatggc acctgccatt gctacctgta cagtcaagga tggtagaaat    4860
gttgtcggtc cttgcacacg aatattacgc catttgcctg catattcaaa cagctcttct    4920
acgataaggg cacaaatcgc atcgtggaac gtttgggctt ctaccgattt agcagtttga    4980
tacactttct ctaagtatcc acctgaatca taaatcggca aaatagagaa aaattgacca    5040
tgtgtaagcg gccaatctga ttccacctga gatgcataat ctagtagaat ctcttcgcta    5100
tcaaaattca cttccacctt ccactcaccg gttgtccatt catggctgaa ctctgcttcc    5160
tctgttgaca tgacacacat catctcaata tccgaatagg gcccatcagt ctgacgacca    5220
```

-continued

```
agagagccat aaacaccaat agccttaaca tcatccccat attttatccaa tattcgttcc    5280 ttaatttcat gaacaatctt cattctttct tctctagtca ttattattgg tccattcact    5340
attctcattc ccttttcaga taattttaga tttgctttct taaataagaa tatttggaga    5400
gcaccgttct tattcagcta ttaataactc gtcttcctaa gcatccttca atcctttaa    5460 taacaattat agcatctaat cttcaacaaa ctggcccgtt tgttgaacta ctctttaata    5520
aaataatttt tccgttccca attccacatt gcaataatag aaaatccatc ttcatcggct    5580
ttttcgtcat catctgtatg aatcaaatcg ccttcttctg tgtcatcaag gtttaatttt    5640
ttatgtattt cttttaacaa accaccatag gagattaacc ttttacggtg taaaccttcc    5700
tccaaatcag acaaacgttt caaattcttt tcttcatcat cggtcataaa atccgtatcc    5760
tttacaggat attttgcagt ttcgtcaatt gccgattgta tatccgattt atatttattt    5820
ttcggtcgaa tcatttgaac ttttacattt ggatcatagt ctaatttcat tgcctttttc    5880
caaaattgaa tccattgttt ttgattcacg tagttttctg tattcttaaa ataagttggt    5940
tccacacata ccaatacatg catgtgctga ttataagaat tatctttatt atttattgtc    6000
acttccgttg cacgcataaa accaacaaga ttttttattaa tttttttttata ttgcatcatt    6060 cggcgaaatc cttgagccat atctgacaaa ctcttattta attcttcgcc atcataaaca    6120 ttttttaactg ttaatgtgag aaacaaccaa cgaactgttg gcttttgttt aataacttca    6180
gcaacaacct tttgtgactg aatgccatgt ttcattgctc tcctccagtt gcacattgga    6240
caaagcctgg atttacaaaa ccacactcga tacaactttc tttcgcctgt ttcacgattt    6300
tgtttatact ctaatatttc agcacaatct tttactcttt cagccttttt aaattcaaga    6360
atatgcagaa gttcaaagta atcaacatta gcgattttct tttctctcca tggtctcact    6420
tttccacttt ttgtcttgtc cactaaaacc cttgattttt catctgaata aatgctacta    6480
ttaggacaca taatattaaa agaaacccccc atctatttag ttatttgttt agtcacttat    6540
aactttaaca gatggggttt ttctgtgcaa ccaattttaa gggtttttcaa tactttaaaa    6600 cacatacata ccaacacttc aacgcacctt tcagcaacta aaataaaaat gacgttattt    6660
ctatatgtat caagataaga aagaacaagt tcaaaaccat caaaaaaaga cacctttttca    6720 ggtgctttt ttattttttata aactcattcc ctgatctcga cttcgttctt tttttaccctc    6780 tcggttatga gttagttcaa attcgttctt tttaggttct aaatcgtgtt tttcttggaa    6840
ttgtgctgtt ttatcctttta ccttgtctac aaaccccttta aaaacgtttt taaaggcttt    6900
taagccgtct gtacgttcct aa                                              6922
```

```
<210> SEQ ID NO 2
<211> LENGTH: 338
<212> TYPE: PRT
<213> ORGANISM: Unknown
<220> FEATURE:
<223> OTHER INFORMATION: Thermobifida fusca

<400> SEQUENCE: 2

Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
            20                  25                  30

Glu Leu Arg Asp Ser Leu Gly Ser Asp Phe Gly Gly Val Tyr Leu Asp
        35                  40                  45

Ala Asp Thr Thr Glu Ile Thr Val Ala Val Thr Asp Pro Ala Ala Val
```

-continued

```
             50                  55                  60

Ser Arg Val Asp Ala Asp Asp Val Thr Val Asp Val Val Asp Phe Gly
65                  70                  75                  80

Glu Thr Ala Leu Asn Asp Phe Val Ala Ser Leu Asn Ala Ile Ala Asp
                85                  90                  95

Thr Ala Asp Pro Lys Val Thr Gly Trp Tyr Thr Asp Leu Glu Ser Asp
            100                 105                 110

Ala Val Val Ile Thr Thr Leu Arg Gly Gly Thr Pro Ala Ala Glu Glu
        115                 120                 125

Leu Ala Glu Arg Ala Gly Leu Asp Glu Arg Ala Val Arg Ile Val Glu
        130                 135                 140

Glu Asp Glu Glu Pro Gln Ser Leu Ala Ala Ile Ile Gly Gly Asn Pro
145                 150                 155                 160

Tyr Tyr Phe Gly Asn Tyr Arg Cys Ser Ile Gly Phe Ser Val Arg Gln
                165                 170                 175

Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
            195                 200                 205

Gly Arg Asp Met Gly Trp Val Arg Ile Thr Ser Ala Asp Thr Val Thr
        210                 215                 220

Pro Leu Val Asn Arg Tyr Asn Gly Gly Thr Val Thr Val Thr Gly Ser
225                 230                 235                 240

Gln Glu Ala Ala Thr Gly Ser Ser Val Cys Arg Ser Gly Ala Thr Thr
                245                 250                 255

Gly Trp Arg Cys Gly Thr Ile Gln Ser Lys Asn Gln Thr Val Arg Tyr
                260                 265                 270

Ala Glu Gly Thr Val Thr Gly Leu Thr Arg Thr Thr Ala Cys Ala Glu
            275                 280                 285

Gly Gly Asp Ser Gly Gly Pro Trp Leu Thr Gly Ser Gln Ala Gln Gly
        290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
                325                 330                 335

Thr Gly
```

<210> SEQ ID NO 3
<211> LENGTH: 338
<212> TYPE: PRT
<213> ORGANISM: Artificial sequence
<220> FEATURE:
<223> OTHER INFORMATION: Synthetic sequence - Thermobifida fusca (F163Y)

<400> SEQUENCE: 3

```
Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
                20                  25                  30

Glu Leu Arg Asp Ser Leu Gly Ser Asp Phe Gly Gly Val Tyr Leu Asp
            35                  40                  45

Ala Asp Thr Thr Glu Ile Thr Val Ala Val Thr Asp Pro Ala Ala Val
        50                  55                  60

Ser Arg Val Asp Ala Asp Asp Val Thr Val Asp Val Val Asp Phe Gly
65                  70                  75                  80
```

```
Glu Thr Ala Leu Asn Asp Phe Val Ala Ser Leu Asn Ala Ile Ala Asp
                85                  90                  95

Thr Ala Asp Pro Lys Val Thr Gly Trp Tyr Thr Asp Leu Glu Ser Asp
            100                 105                 110

Ala Val Val Ile Thr Thr Leu Arg Gly Gly Thr Pro Ala Ala Glu Glu
            115                 120                 125

Leu Ala Glu Arg Ala Gly Leu Asp Glu Arg Ala Val Arg Ile Val Glu
        130                 135                 140

Glu Asp Glu Glu Pro Gln Ser Leu Ala Ala Ile Ile Gly Gly Asn Pro
145                 150                 155                 160

Tyr Tyr Tyr Gly Asn Tyr Arg Cys Ser Ile Gly Phe Ser Val Arg Gln
                165                 170                 175

Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
        195                 200                 205

Gly Arg Asp Met Gly Trp Val Arg Ile Thr Ser Ala Asp Thr Val Thr
    210                 215                 220

Pro Leu Val Asn Arg Tyr Asn Gly Gly Thr Val Thr Val Thr Gly Ser
225                 230                 235                 240

Gln Glu Ala Ala Thr Gly Ser Ser Val Cys Arg Ser Gly Ala Thr Thr
                245                 250                 255

Gly Trp Arg Cys Gly Thr Ile Gln Ser Lys Asn Gln Thr Val Arg Tyr
            260                 265                 270

Ala Glu Gly Thr Val Thr Gly Leu Thr Arg Thr Thr Ala Cys Ala Glu
            275                 280                 285

Gly Gly Asp Ser Gly Gly Pro Trp Leu Thr Gly Ser Gln Ala Gln Gly
        290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
                325                 330                 335

Thr Gly
```

<210> SEQ ID NO 4
<211> LENGTH: 338
<212> TYPE: PRT
<213> ORGANISM: Artificial sequence
<220> FEATURE:
<223> OTHER INFORMATION: Synthetic Thermobifida fusca (F163Y_N267D)
      sequence

<400> SEQUENCE: 4

```
Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
                20                  25                  30

Glu Leu Arg Asp Ser Leu Gly Ser Asp Phe Gly Gly Val Tyr Leu Asp
        35                  40                  45

Ala Asp Thr Thr Glu Ile Thr Val Ala Val Thr Asp Pro Ala Ala Val
        50                  55                  60

Ser Arg Val Asp Ala Asp Asp Val Thr Val Asp Val Val Asp Phe Gly
65                  70                  75                  80

Glu Thr Ala Leu Asn Asp Phe Val Ala Ser Leu Asn Ala Ile Ala Asp
                85                  90                  95
```

-continued

```
Thr Ala Asp Pro Lys Val Thr Gly Trp Tyr Thr Asp Leu Glu Ser Asp
            100                 105                 110

Ala Val Val Ile Thr Thr Leu Arg Gly Gly Thr Pro Ala Ala Glu Glu
            115                 120                 125

Leu Ala Glu Arg Ala Gly Leu Asp Glu Arg Ala Val Arg Ile Val Glu
            130                 135                 140

Glu Asp Glu Glu Pro Gln Ser Leu Ala Ala Ile Ile Gly Gly Asn Pro
145                 150                 155                 160

Tyr Tyr Tyr Gly Asn Tyr Arg Cys Ser Ile Gly Phe Ser Val Arg Gln
                165                 170                 175

Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
            195                 200                 205

Gly Arg Asp Met Gly Trp Val Arg Ile Thr Ser Ala Asp Thr Val Thr
            210                 215                 220

Pro Leu Val Asn Arg Tyr Asn Gly Gly Thr Val Thr Val Thr Gly Ser
225                 230                 235                 240

Gln Glu Ala Ala Thr Gly Ser Ser Val Cys Arg Ser Gly Ala Thr Thr
                245                 250                 255

Gly Trp Arg Cys Gly Thr Ile Gln Ser Lys Asp Gln Thr Val Arg Tyr
            260                 265                 270

Ala Glu Gly Thr Val Thr Gly Leu Thr Arg Thr Thr Ala Cys Ala Glu
            275                 280                 285

Gly Gly Asp Ser Gly Gly Pro Trp Leu Thr Gly Ser Gln Ala Gln Gly
            290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
                325                 330                 335

Thr Gly
```

```
<210> SEQ ID NO 5
<211> LENGTH: 338
<212> TYPE: PRT
<213> ORGANISM: Artificial sequence
<220> FEATURE:
<223> OTHER INFORMATION: Synthetic sequence - Thermobifida fusca
      (F163Y_N267S)

<400> SEQUENCE: 5
```

```
Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
            20                  25                  30

Glu Leu Arg Asp Ser Leu Gly Ser Asp Phe Gly Gly Val Tyr Leu Asp
        35                  40                  45

Ala Asp Thr Thr Glu Ile Thr Val Ala Val Thr Asp Pro Ala Ala Val
    50                  55                  60

Ser Arg Val Asp Ala Asp Asp Val Thr Val Asp Val Val Asp Phe Gly
65                  70                  75                  80

Glu Thr Ala Leu Asn Asp Phe Val Ala Ser Leu Asn Ala Ile Ala Asp
                85                  90                  95

Thr Ala Asp Pro Lys Val Thr Gly Trp Tyr Thr Asp Leu Glu Ser Asp
            100                 105                 110
```

```
Ala Val Val Ile Thr Thr Leu Arg Gly Gly Thr Pro Ala Ala Glu Glu
        115                 120                 125

Leu Ala Glu Arg Ala Gly Leu Asp Glu Arg Ala Val Arg Ile Val Glu
        130                 135                 140

Glu Asp Glu Glu Pro Gln Ser Leu Ala Ala Ile Ile Gly Gly Asn Pro
145                 150                 155                 160

Tyr Tyr Tyr Gly Asn Tyr Arg Cys Ser Ile Gly Phe Ser Val Arg Gln
                165                 170                 175

Gly Ser Gln Thr Gly Phe Ala Thr Ala Gly His Cys Gly Ser Thr Gly
                180                 185                 190

Thr Arg Val Ser Ser Pro Ser Gly Thr Val Ala Gly Ser Tyr Phe Pro
        195                 200                 205

Gly Arg Asp Met Gly Trp Val Arg Ile Thr Ser Ala Asp Thr Val Thr
        210                 215                 220

Pro Leu Val Asn Arg Tyr Asn Gly Gly Thr Val Thr Val Thr Gly Ser
225                 230                 235                 240

Gln Glu Ala Ala Thr Gly Ser Ser Val Cys Arg Ser Gly Ala Thr Thr
                245                 250                 255

Gly Trp Arg Cys Gly Thr Ile Gln Ser Lys Ser Gln Thr Val Arg Tyr
                260                 265                 270

Ala Glu Gly Thr Val Thr Gly Leu Thr Arg Thr Thr Ala Cys Ala Glu
        275                 280                 285

Gly Gly Asp Ser Gly Gly Pro Trp Leu Thr Gly Ser Gln Ala Gln Gly
        290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
                325                 330                 335

Thr Gly
```

```
<210> SEQ ID NO 6
<211> LENGTH: 338
<212> TYPE: PRT
<213> ORGANISM: Artificial sequence
<220> FEATURE:
<223> OTHER INFORMATION: Synthetic sequence -Thermobifida fusca
     (F163S_N267D)

<400> SEQUENCE: 6
```

```
Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
                20                  25                  30

Glu Leu Arg Asp Ser Leu Gly Ser Asp Phe Gly Gly Val Tyr Leu Asp
        35                  40                  45

Ala Asp Thr Thr Glu Ile Thr Val Ala Val Thr Asp Pro Ala Ala Val
        50                  55                  60

Ser Arg Val Asp Ala Asp Asp Val Thr Val Asp Val Val Asp Phe Gly
65                  70                  75                  80

Glu Thr Ala Leu Asn Asp Phe Val Ala Ser Leu Asn Ala Ile Ala Asp
                85                  90                  95

Thr Ala Asp Pro Lys Val Thr Gly Trp Tyr Thr Asp Leu Glu Ser Asp
                100                 105                 110

Ala Val Val Ile Thr Thr Leu Arg Gly Gly Thr Pro Ala Ala Glu Glu
        115                 120                 125
```

-continued

```
Leu Ala Glu Arg Ala Gly Leu Asp Glu Arg Ala Val Arg Ile Val Glu
    130                 135                 140

Glu Asp Glu Glu Pro Gln Ser Leu Ala Ala Ile Ile Gly Gly Asn Pro
145                 150                 155                 160

Tyr Tyr Ser Gly Asn Tyr Arg Cys Ser Ile Gly Phe Ser Val Arg Gln
                165                 170                 175

Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
            195                 200                 205

Gly Arg Asp Met Gly Trp Val Arg Ile Thr Ser Ala Asp Thr Val Thr
    210                 215                 220

Pro Leu Val Asn Arg Tyr Asn Gly Gly Thr Val Thr Val Thr Gly Ser
225                 230                 235                 240

Gln Glu Ala Ala Thr Gly Ser Ser Val Cys Arg Ser Gly Ala Thr Thr
                245                 250                 255

Gly Trp Arg Cys Gly Thr Ile Gln Ser Lys Asp Gln Thr Val Arg Tyr
                260                 265                 270

Ala Glu Gly Thr Val Thr Gly Leu Thr Arg Thr Thr Ala Cys Ala Glu
            275                 280                 285

Gly Gly Asp Ser Gly Gly Pro Trp Leu Thr Gly Ser Gln Ala Gln Gly
    290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
                325                 330                 335

Thr Gly
```

```
<210> SEQ ID NO 7
<211> LENGTH: 338
<212> TYPE: PRT
<213> ORGANISM: Artificial sequence
<220> FEATURE:
<223> OTHER INFORMATION: Synthetic sequence - Thermobifida fusca
      (F163S_N267T)

<400> SEQUENCE: 7
```

```
Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
                20                  25                  30

Glu Leu Arg Asp Ser Leu Gly Ser Asp Phe Gly Gly Val Tyr Leu Asp
            35                  40                  45

Ala Asp Thr Thr Glu Ile Thr Val Ala Val Thr Asp Pro Ala Ala Val
    50                  55                  60

Ser Arg Val Asp Ala Asp Asp Val Thr Val Asp Val Asp Phe Gly
65                  70                  75                  80

Glu Thr Ala Leu Asn Asp Phe Val Ala Ser Leu Asn Ala Ile Ala Asp
                85                  90                  95

Thr Ala Asp Pro Lys Val Thr Gly Trp Tyr Thr Asp Leu Glu Ser Asp
                100                 105                 110

Ala Val Val Ile Thr Thr Leu Arg Gly Gly Thr Pro Ala Ala Glu Glu
            115                 120                 125

Leu Ala Glu Arg Ala Gly Leu Asp Glu Arg Ala Val Arg Ile Val Glu
    130                 135                 140
```

-continued

```
Glu Asp Glu Glu Pro Gln Ser Leu Ala Ala Ile Ile Gly Gly Asn Pro
145                 150                 155                 160

Tyr Tyr Ser Gly Asn Tyr Arg Cys Ser Ile Gly Phe Ser Val Arg Gln
                165                 170                 175

Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
        195                 200                 205

Gly Arg Asp Met Gly Trp Val Arg Ile Thr Ser Ala Asp Thr Val Thr
    210                 215                 220

Pro Leu Val Asn Arg Tyr Asn Gly Gly Thr Val Thr Val Thr Gly Ser
225                 230                 235                 240

Gln Glu Ala Ala Thr Gly Ser Ser Val Cys Arg Ser Gly Ala Thr Thr
                245                 250                 255

Gly Trp Arg Cys Gly Thr Ile Gln Ser Lys Thr Gln Thr Val Arg Tyr
            260                 265                 270

Ala Glu Gly Thr Val Thr Gly Leu Thr Arg Thr Thr Ala Cys Ala Glu
        275                 280                 285

Gly Gly Asp Ser Gly Gly Pro Trp Leu Thr Gly Ser Gln Ala Gln Gly
    290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
                325                 330                 335

Thr Gly
```

```
<210> SEQ ID NO 8
<211> LENGTH: 338
<212> TYPE: PRT
<213> ORGANISM: Artificial sequence
<220> FEATURE:
<223> OTHER INFORMATION: Synthetic sequence - Thermobifida fusca
      (F163A_N267G)

<400> SEQUENCE: 8
```

```
Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
            20                  25                  30

Glu Leu Arg Asp Ser Leu Gly Ser Asp Phe Gly Gly Val Tyr Leu Asp
        35                  40                  45

Ala Asp Thr Thr Glu Ile Thr Val Ala Val Thr Asp Pro Ala Ala Val
    50                  55                  60

Ser Arg Val Asp Ala Asp Asp Val Thr Val Val Asp Phe Gly
65                  70                  75                  80

Glu Thr Ala Leu Asn Asp Phe Val Ala Ser Leu Asn Ala Ile Ala Asp
                85                  90                  95

Thr Ala Asp Pro Lys Val Thr Gly Trp Tyr Thr Asp Leu Glu Ser Asp
            100                 105                 110

Ala Val Val Ile Thr Thr Leu Arg Gly Gly Thr Pro Ala Ala Glu Glu
        115                 120                 125

Leu Ala Glu Arg Ala Gly Leu Asp Glu Arg Ala Val Arg Ile Val Glu
    130                 135                 140

Glu Asp Glu Glu Pro Gln Ser Leu Ala Ala Ile Ile Gly Gly Asn Pro
145                 150                 155                 160
```

-continued

```
Tyr Tyr Ala Gly Asn Tyr Arg Cys Ser Ile Gly Phe Ser Val Arg Gln
            165                 170                 175

Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
            195                 200                 205

Gly Arg Asp Met Gly Trp Val Arg Ile Thr Ser Ala Asp Thr Val Thr
    210                 215                 220

Pro Leu Val Asn Arg Tyr Asn Gly Gly Thr Val Thr Val Thr Gly Ser
225                 230                 235                 240

Gln Glu Ala Ala Thr Gly Ser Ser Val Cys Arg Ser Gly Ala Thr Thr
            245                 250                 255

Gly Trp Arg Cys Gly Thr Ile Gln Ser Lys Gly Gln Thr Val Arg Tyr
            260                 265                 270

Ala Glu Gly Thr Val Thr Gly Leu Thr Arg Thr Thr Ala Cys Ala Glu
            275                 280                 285

Gly Gly Asp Ser Gly Gly Pro Trp Leu Thr Gly Ser Gln Ala Gln Gly
    290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
            325                 330                 335

Thr Gly

<210> SEQ ID NO 9
<211> LENGTH: 338
<212> TYPE: PRT
<213> ORGANISM: Artificial sequence
<220> FEATURE:
<223> OTHER INFORMATION: Synthetic sequence - Thermobifida fusca (F163A)

<400> SEQUENCE: 9

Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
            20                  25                  30

Glu Leu Arg Asp Ser Leu Gly Ser Asp Phe Gly Gly Val Tyr Leu Asp
            35                  40                  45

Ala Asp Thr Thr Glu Ile Thr Val Ala Val Thr Asp Pro Ala Ala Val
    50                  55                  60

Ser Arg Val Asp Ala Asp Asp Val Thr Val Asp Val Asp Phe Gly
65                  70                  75                  80

Glu Thr Ala Leu Asn Asp Phe Val Ala Ser Leu Asn Ala Ile Ala Asp
            85                  90                  95

Thr Ala Asp Pro Lys Val Thr Gly Trp Tyr Thr Asp Leu Glu Ser Asp
            100                 105                 110

Ala Val Val Ile Thr Thr Leu Arg Gly Gly Thr Pro Ala Ala Glu Glu
            115                 120                 125

Leu Ala Glu Arg Ala Gly Leu Asp Glu Arg Ala Val Arg Ile Val Glu
    130                 135                 140

Glu Asp Glu Glu Pro Gln Ser Leu Ala Ala Ile Ile Gly Gly Asn Pro
145                 150                 155                 160

Tyr Tyr Ala Gly Asn Tyr Arg Cys Ser Ile Gly Phe Ser Val Arg Gln
            165                 170                 175
```

```
Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
            195                 200                 205

Gly Arg Asp Met Gly Trp Val Arg Ile Thr Ser Ala Asp Thr Val Thr
        210                 215                 220

Pro Leu Val Asn Arg Tyr Asn Gly Gly Thr Val Thr Val Thr Gly Ser
    225                 230                 235                 240

Gln Glu Ala Ala Thr Gly Ser Ser Val Cys Arg Ser Gly Ala Thr Thr
                    245                 250                 255

Gly Trp Arg Cys Gly Thr Ile Gln Ser Lys Asn Gln Thr Val Arg Tyr
                260                 265                 270

Ala Glu Gly Thr Val Thr Gly Leu Thr Arg Thr Thr Ala Cys Ala Glu
            275                 280                 285

Gly Gly Asp Ser Gly Gly Pro Trp Leu Thr Gly Ser Gln Ala Gln Gly
        290                 295                 300

Val Thr Ser Gly Gly Thr Gly Asp Cys Arg Ser Gly Gly Ile Thr Phe
305                 310                 315                 320

Phe Gln Pro Ile Asn Pro Leu Leu Ser Tyr Phe Gly Leu Gln Leu Val
                325                 330                 335

Thr Gly

<210> SEQ ID NO 10
<211> LENGTH: 338
<212> TYPE: PRT
<213> ORGANISM: Artificial sequence
<220> FEATURE:
<223> OTHER INFORMATION: Synthetic sequence - Thermobifida fusca (F163R)

<400> SEQUENCE: 10

Met Gln Glu Leu Ala Leu Lys Arg Asp Leu Gly Leu Ser Asp Ala Glu
1               5                   10                  15

Val Ala Glu Leu Arg Ala Ala Glu Ala Glu Ala Val Glu Leu Glu Glu
            20                  25                  30

Glu Leu Arg Asp Ser Leu Gly Ser Asp Phe Gly Gly Val Tyr Leu Asp
        35                  40                  45

Ala Asp Thr Thr Glu Ile Thr Val Ala Val Thr Asp Pro Ala Ala Val
    50                  55                  60

Ser Arg Val Asp Ala Asp Asp Val Thr Val Asp Val Asp Phe Gly
65                  70                  75                  80

Glu Thr Ala Leu Asn Asp Phe Val Ala Ser Leu Asn Ala Ile Ala Asp
                85                  90                  95

Thr Ala Asp Pro Lys Val Thr Gly Trp Tyr Thr Asp Leu Glu Ser Asp
            100                 105                 110

Ala Val Val Ile Thr Thr Leu Arg Gly Gly Thr Pro Ala Ala Glu Glu
        115                 120                 125

Leu Ala Glu Arg Ala Gly Leu Asp Glu Arg Ala Val Arg Ile Val Glu
        130                 135                 140

Glu Asp Glu Glu Pro Gln Ser Leu Ala Ala Ile Ile Gly Gly Asn Pro
145                 150                 155                 160

Tyr Tyr Arg Gly Asn Tyr Arg Cys Ser Ile Gly Phe Ser Val Arg Gln
                165                 170                 175

Gly Ser Gln Thr Gly Phe Ala Thr Ala Gly His Cys Gly Ser Thr Gly
            180                 185                 190

Thr Arg Val Ser Ser Pro Ser Gly Thr Val Ala Gly Ser Tyr Phe Pro
```

-continued

```
                195              200              205

Gly Arg Asp Met Gly Trp Val Arg Ile Thr Ser Ala Asp Thr Val Thr
    210              215              220

Pro Leu Val Asn Arg Tyr Asn Gly Gly Thr Val Thr Val Thr Gly Ser
225              230              235              240

Gln Glu Ala Ala Thr Gly Ser Ser Val Cys Arg Ser Gly Ala Thr Thr
                245              250              255

Gly Trp Arg Cys Gly Thr Ile Gln Ser Lys Asn Gln Thr Val Arg Tyr
                260              265              270

Ala Glu Gly Thr Val Thr Gly Leu Thr Arg Thr Thr Ala Cys Ala Glu
            275              280              285

Gly Gly Asp Ser Gly Gly Pro Trp Leu Thr Gly Ser Gln Ala Gln Gly
        290              295              300

Val Thr Ser Gly Gly Thr Gly Asp Cys Arg Ser Gly Gly Ile Thr Phe
305              310              315              320

Phe Gln Pro Ile Asn Pro Leu Leu Ser Tyr Phe Gly Leu Gln Leu Val
                325              330              335

Thr Gly
```

<210> SEQ ID NO 11
<211> LENGTH: 47
<212> TYPE: DNA
<213> ORGANISM: Artificial sequence
<220> FEATURE:
<223> OTHER INFORMATION: Synthetic sequence - TAP_mature region_F

<400> SEQUENCE: 11
aagaagatga agaaccacag agcttggctg caattattgg tggaaac                47

<210> SEQ ID NO 12
<211> LENGTH: 44
<212> TYPE: DNA
<213> ORGANISM: Artificial sequence
<220> FEATURE:
<223> OTHER INFORMATION: Synthetic sequence - TAP_mature region_R

<400> SEQUENCE: 12
gactgcaggt cgacaagctt tcagccggtc actaattgaa ggcc                44

<210> SEQ ID NO 13
<211> LENGTH: 23
<212> TYPE: DNA
<213> ORGANISM: Artificial sequence
<220> FEATURE:
<223> OTHER INFORMATION: Synthetic sequence - pBE-S-vector-F

<400> SEQUENCE: 13
aagcttgtcg acctgcagtc tag                23

<210> SEQ ID NO 14
<211> LENGTH: 24
<212> TYPE: DNA
<213> ORGANISM: Artificial sequence
<220> FEATURE:
<223> OTHER INFORMATION: Synthetic sequence - pBE-S-vector-R

<400> SEQUENCE: 14
ctgtggttct tcatcttctt ccac                24

<210> SEQ ID NO 15
<211> LENGTH: 37

<212> TYPE: DNA
<213> ORGANISM: Artificial sequence
<220> FEATURE:
<223> OTHER INFORMATION: Synthetic sequence - TAP_F12Y_F

<400> SEQUENCE: 15
gtggaaaccc gtactattac ggaaattaca gatgcag                                37

<210> SEQ ID NO 16
<211> LENGTH: 37
<212> TYPE: DNA
<213> ORGANISM: Artificial sequence
<220> FEATURE:
<223> OTHER INFORMATION: Synthetic sequence - TAP_F12Y_R

<400> SEQUENCE: 16
ctgcatctgt aatttccgta atagtacggg tttccac                                37

<210> SEQ ID NO 17
<211> LENGTH: 38
<212> TYPE: DNA
<213> ORGANISM: Artificial sequence
<220> FEATURE:
<223> OTHER INFORMATION: Synthetic sequence - TAP_N116D_F

<400> SEQUENCE: 17
ggaactatcc aatcaaaaga ccaaacggtt cgctatgc                               38

<210> SEQ ID NO 18
<211> LENGTH: 38
<212> TYPE: DNA
<213> ORGANISM: Artificial sequence
<220> FEATURE:
<223> OTHER INFORMATION: Synthetic sequence - TAP_N116D_R

<400> SEQUENCE: 18
gcatagcgaa ccgtttggtc ttttgattgg atagttcc                               38

<210> SEQ ID NO 19
<211> LENGTH: 37
<212> TYPE: DNA
<213> ORGANISM: Artificial sequence
<220> FEATURE:
<223> OTHER INFORMATION: Synthetic sequence Saturation mutagenesis_F_1
<220> FEATURE:
<221> NAME/KEY: misc_feature
<222> LOCATION: (18)..(20)
<223> OTHER INFORMATION: n is a, c, g, or t

<400> SEQUENCE: 19
gtggaaaccc gtactatnnn ggaaattaca gatgcag                                37

<210> SEQ ID NO 20
<211> LENGTH: 38
<212> TYPE: DNA
<213> ORGANISM: Artificial sequence
<220> FEATURE:
<223> OTHER INFORMATION: Synthetic sequence Saturation mutagenesis_R_1
<220> FEATURE:
<221> NAME/KEY: misc_feature
<222> LOCATION: (18)..(20)
<223> OTHER INFORMATION: n is a, c, g, or t

<400> SEQUENCE: 20
gcatagcgaa ccgtttgnnn ttttgattgg atagttcc                               38

<210> SEQ ID NO 21

-continued

```
<211> LENGTH: 38
<212> TYPE: DNA
<213> ORGANISM: Artificial sequence
<220> FEATURE:
<223> OTHER INFORMATION: Synthetic sequence - Saturation mutagenesis_F_2
<220> FEATURE:
<221> NAME/KEY: misc_feature
<222> LOCATION: (19)..(21)
<223> OTHER INFORMATION: n is a, c, g, or t

<400> SEQUENCE: 21
ggaactatcc aatcaaaann ncaaacggtt cgctatgc                              38

<210> SEQ ID NO 22
<211> LENGTH: 37
<212> TYPE: DNA
<213> ORGANISM: Artificial sequence
<220> FEATURE:
<223> OTHER INFORMATION: Synthetic sequence - Saturation mutagenesis_R_2
<220> FEATURE:
<221> NAME/KEY: misc_feature
<222> LOCATION: (18)..(20)
<223> OTHER INFORMATION: n is a, c, g, or t

<400> SEQUENCE: 22
ctgcatctgt aatttccnnn atagtacggg tttccac                               37

<210> SEQ ID NO 23
<211> LENGTH: 1017
<212> TYPE: DNA
<213> ORGANISM: Artificial sequence
<220> FEATURE:
<223> OTHER INFORMATION: Synthetic sequence - Thermobifida fusca (F12Y)

<400> SEQUENCE: 23
atgcaagagc tggcgttgaa acgggacctc ggcctctctg acgcagaagt agccgaactc     60
cgggctgctg aggcggaagc ggtcgagctc gaggaggagc tccgcgattc attagggtca    120
gacttcggcg gtgtatatct ggatgctgac accaccgaaa ttacggtcgc ggtaaccgac    180
ccggcagcgg taagtcgtgt cgacgcggat gatgtcacag ttgatgttgt cgatttcggg    240
gaaacagctt tgaatgattt tgtggcttca ttaaatgcca ttgccgacac ggcagaccct    300
aaagtcactg gatggtatac cgatctcgaa agtgatgccg tagtcattac gaccttgcgt    360
ggcgggactc ctgctgccga ggaacttgct gagagagcgg gtctcgacga aagagccgtt    420
cggattgtgg aagaagatga agaaccacag agcttggctg caattattgg tggaaacccg    480
tactattacg aaattacag atgcagtatc gggtttagtg tccgtcaggg ctctcaaacg      540
ggattcgcga ccgcaggcca ctgcggatcc acggggacgc gtgtgtcttc tccttcagga    600
acagttgcag gaagttattt cccgggtcgc gatatgggct gggtgcggat tacatcagca    660
gatactgtaa caccactcgt aaatcggtat aatggggggaa ctgttacggt cactgggtca    720
caagaagctg ccaccggatc ctccgtttgt cgctctggag caacaacggg ctggcgctgc    780
ggaactatcc aatcaaaaaa ccaaacggtt cgctatgcag aagggactgt tactggttta    840
acaagaacta cagcctgtgc tgaaggtggg gattctggag ggccatggct cacaggtagc    900
caggcgcaag gggttacaag cggcggaaca ggcgattgca gaagtggagg gattaccttt    960
ttccaaccaa tcaatccatt gcttagctat ttcggccttc aattagtgac cggctga     1017

<210> SEQ ID NO 24
<211> LENGTH: 1017
<212> TYPE: DNA
<213> ORGANISM: Artificial sequence
```

-continued

```
<220> FEATURE:
<223> OTHER INFORMATION: Synthetic sequence - Thermobifida fusca
      (F163Y_N267D)

<400> SEQUENCE: 24
atgcaagagc tggcgttgaa acgggacctc ggcctctctg acgcagaagt agccgaactc     60
cgggctgctg aggcggaagc ggtcgagctc gaggaggagc tccgcgattc attagggtca    120
gacttcggcg gtgtatatct ggatgctgac accaccgaaa ttacggtcgc ggtaaccgac    180
ccggcagcgg taagtcgtgt cgacgcggat gatgtcacag ttgatgttgt cgatttcggg    240
gaaacagctt tgaatgattt tgtggcttca ttaaatgcca ttgccgacac ggcagaccct    300
aaagtcactg gatggtatac cgatctcgaa agtgatgccg tagtcattac gaccttgcgt    360
ggcgggactc ctgctgccga ggaacttgct gagagagcgg gtctcgacga aagagccgtt    420
cggattgtgg aagaagatga agaaccacag agcttggctg caattattgg tggaaacccg    480
tactattacg gaaattacag atgcagtatc gggtttagtg tccgtcaggg ctctcaaacg    540
ggattcgcga ccgcaggcca ctgcggatcc acggggacgc gtgtgtcttc tccttcagga    600
acagttgcag gaagttattt cccgggtcgc gatatgggct gggtgcggat tacatcagca    660
gatactgtaa caccactcgt aaatcggtat aatgggggaa ctgttacggt cactgggtca    720
caagaagctg ccaccggatc ctccgtttgt cgctctggag caacaacggg ctggcgctgc    780
ggaactatcc aatcaaaaga ccaaacggtt cgctatgcag aagggactgt tactggttta    840
acaagaacta cagcctgtgc tgaaggtggg gattctggag gccatggct cacaggtagc     900 caggcgcaag gggttacaag cggcggaaca ggcgattgca gaagtggagg gattaccttt    960
ttccaaccaa tcaatccatt gcttagctat ttcggccttc aattagtgac cggctga      1017

<210> SEQ ID NO 25
<211> LENGTH: 1017
<212> TYPE: DNA
<213> ORGANISM: Artificial sequence
<220> FEATURE:
<223> OTHER INFORMATION: Synthetic sequence - Thermobifida fusca
      (F163Y_N267S)

<400> SEQUENCE: 25
atgcaagagc tggcgttgaa acgggacctc ggcctctctg acgcagaagt agccgaactc     60
cgggctgctg aggcggaagc ggtcgagctc gaggaggagc tccgcgattc attagggtca    120
gacttcggcg gtgtatatct ggatgctgac accaccgaaa ttacggtcgc ggtaaccgac    180
ccggcagcgg taagtcgtgt cgacgcggat gatgtcacag ttgatgttgt cgatttcggg    240
gaaacagctt tgaatgattt tgtggcttca ttaaatgcca ttgccgacac ggcagaccct    300
aaagtcactg gatggtatac cgatctcgaa agtgatgccg tagtcattac gaccttgcgt    360
ggcgggactc ctgctgccga ggaacttgct gagagagcgg gtctcgacga aagagccgtt    420
cggattgtgg aagaagatga agaaccacag agcttggctg caattattgg tggaaacccg    480
tactattacg gaaattacag atgcagtatc gggtttagtg tccgtcaggg ctctcaaacg    540
ggattcgcga ccgcaggcca ctgcggatcc acggggacgc gtgtgtcttc tccttcagga    600
acagttgcag gaagttattt cccgggtcgc gatatgggct gggtgcggat tacatcagca    660
gatactgtaa caccactcgt aaatcggtat aatgggggaa ctgttacggt cactgggtca    720
caagaagctg ccaccggatc ctccgtttgt cgctctggag caacaacggg ctggcgctgc    780
ggaactatcc aatcaaaaag tcaaacggtt cgctatgcag aagggactgt tactggttta    840
```

-continued

```
acaagaacta cagcctgtgc tgaaggtggg gattctggag ggccatggct cacaggtagc      900
caggcgcaag gggttacaag cggcggaaca ggcgattgca gaagtggagg gattaccttt      960
ttccaaccaa tcaatccatt gcttagctat ttcggccttc aattagtgac cggctga        1017

<210> SEQ ID NO 26
<211> LENGTH: 1017
<212> TYPE: DNA
<213> ORGANISM: Artificial sequence
<220> FEATURE:
<223> OTHER INFORMATION: Synthetic sequence - Thermobifida fusca
      (F163S_N267D)

<400> SEQUENCE: 26
atgcaagagc tggcgttgaa acgggacctc ggcctctctg acgcagaagt agccgaactc       60
cgggctgctg aggcggaagc ggtcgagctc gaggaggagc tccgcgattc attagggtca      120
gacttcggcg gtgtatatct ggatgctgac accaccgaaa ttacggtcgc ggtaaccgac      180
ccggcagcgg taagtcgtgt cgacgcggat gatgtcacag ttgatgttgt cgatttcggg      240
gaaacagctt tgaatgattt tgtggcttca ttaaatgcca ttgccgacac ggcagaccct      300
aaagtcactg gatggtatac cgatctcgaa agtgatgccg tagtcattac gaccttgcgt      360
ggcgggactc ctgctgccga ggaacttgct gagagagcgg gtctcgacga aagagccgtt      420
cggattgtgg aagaagatga agaaccacag agcttggctg caattattgg tggaaacccg      480
tactatagtg aaattacag atgcagtatc gggtttagtg tccgtcaggg ctctcaaacg       540
ggattcgcga ccgcaggcca ctgcggatcc acgggacgc gtgtgtcttc tccttcagga       600
acagttgcag gaagttattt cccgggtcgc gatatgggct gggtgcggat tacatcagca      660
gatactgtaa caccactcgt aaatcggtat aatggggggaa ctgttacggt cactgggtca     720
caagaagctg ccaccggatc ctccgtttgt cgctctggag caacaacggg ctggcgctgc      780
ggaactatcc aatcaaaaga tcaaacggtt cgctatgcag aagggactgt tactggttta      840
acaagaacta cagcctgtgc tgaaggtggg gattctggag ggccatggct cacaggtagc      900
caggcgcaag gggttacaag cggcggaaca ggcgattgca gaagtggagg gattaccttt      960
ttccaaccaa tcaatccatt gcttagctat ttcggccttc aattagtgac cggctga        1017

<210> SEQ ID NO 27
<211> LENGTH: 1017
<212> TYPE: DNA
<213> ORGANISM: Artificial sequence
<220> FEATURE:
<223> OTHER INFORMATION: Synthetic sequence - Thermobifida fusca
      (F163S_N267T)

<400> SEQUENCE: 27
atgcaagagc tggcgttgaa acgggacctc ggcctctctg acgcagaagt agccgaactc       60
cgggctgctg aggcggaagc ggtcgagctc gaggaggagc tccgcgattc attagggtca      120
gacttcggcg gtgtatatct ggatgctgac accaccgaaa ttacggtcgc ggtaaccgac      180
ccggcagcgg taagtcgtgt cgacgcggat gatgtcacag ttgatgttgt cgatttcggg      240
gaaacagctt tgaatgattt tgtggcttca ttaaatgcca ttgccgacac ggcagaccct      300
aaagtcactg gatggtatac cgatctcgaa agtgatgccg tagtcattac gaccttgcgt      360
ggcgggactc ctgctgccga ggaacttgct gagagagcgg gtctcgacga aagagccgtt      420
cggattgtgg aagaagatga agaaccacag agcttggctg caattattgg tggaaacccg      480
tactatagtg aaattacag atgcagtatc gggtttagtg tccgtcaggg ctctcaaacg       540
```

```
ggattcgcga ccgcaggcca ctgcggatcc acggggacgc gtgtgtcttc tccttcagga      600
acagttgcag gaagttattt cccgggtcgc gatatgggct gggtgcggat tacatcagca      660
gatactgtaa caccactcgt aaatcggtat aatgggggaa ctgttacggt cactgggtca      720
caagaagctg ccaccggatc ctccgtttgt cgctctggag caacaacggg ctggcgctgc      780
ggaactatcc aatcaaaaac tcaaacggtt cgctatgcag aagggactgt tactggttta      840
acaagaacta cagcctgtgc tgaaggtggg gattctggag ggccatggct cacaggtagc      900
caggcgcaag gggttacaag cggcggaaca ggcgattgca gaagtggagg gattaccttt      960
ttccaaccaa tcaatccatt gcttagctat ttcggccttc aattagtgac cggctga       1017
```

<210> SEQ ID NO 28
<211> LENGTH: 1017
<212> TYPE: DNA
<213> ORGANISM: Artificial sequence
<220> FEATURE:
<223> OTHER INFORMATION: Synthetic sequence - Thermobifida fusca
      (F163A_N267G)

<400> SEQUENCE: 28

```
atgcaagagc tggcgttgaa acgggacctc ggcctctctg acgcagaagt agccgaactc       60
cgggctgctg aggcggaagc ggtcgagctc gaggaggagc tccgcgattc attagggtca      120
gacttcggcg gtgtatatct ggatgctgac accaccgaaa ttacggtcgc ggtaaccgac      180
ccggcagcgg taagtcgtgt cgacgcggat gatgtcacag ttgatgttgt cgatttcggg      240
gaaacagctt tgaatgattt tgtggcttca ttaaatgcca ttgccgacac ggcagaccct      300
aaagtcactg gatggtatac cgatctcgaa agtgatgccg tagtcattac gaccttgcgt      360
ggcgggactc tgctgccgga ggaacttgct gagagagcgg gtctcgacga aagagccgtt      420
cggattgtgg aagaagatga agaaccacag agcttggctg caattattgg tggaaacccg      480
tactatgctg aaattacag atgcagtatc gggtttagtg tccgtcaggg ctctcaaacg      540
ggattcgcga ccgcaggcca ctgcggatcc acggggacgc gtgtgtcttc tccttcagga      600
acagttgcag gaagttattt cccgggtcgc gatatgggct gggtgcggat tacatcagca      660
gatactgtaa caccactcgt aaatcggtat aatgggggaa ctgttacggt cactgggtca      720
caagaagctg ccaccggatc ctccgtttgt cgctctggag caacaacggg ctggcgctgc      780
ggaactatcc aatcaaaagg tcaaacggtt cgctatgcag aagggactgt tactggttta      840
acaagaacta cagcctgtgc tgaaggtggg gattctggag ggccatggct cacaggtagc      900
caggcgcaag gggttacaag cggcggaaca ggcgattgca gaagtggagg gattaccttt      960
ttccaaccaa tcaatccatt gcttagctat ttcggccttc aattagtgac cggctga       1017
```

<210> SEQ ID NO 29
<211> LENGTH: 1017
<212> TYPE: DNA
<213> ORGANISM: Artificial sequence
<220> FEATURE:
<223> OTHER INFORMATION: Synthetic sequence - Thermobifida fusca (F163A)

<400> SEQUENCE: 29

```
atgcaagagc tggcgttgaa acgggacctc ggcctctctg acgcagaagt agccgaactc       60
cgggctgctg aggcggaagc ggtcgagctc gaggaggagc tccgcgattc attagggtca      120
gacttcggcg gtgtatatct ggatgctgac accaccgaaa ttacggtcgc ggtaaccgac      180
ccggcagcgg taagtcgtgt cgacgcggat gatgtcacag ttgatgttgt cgatttcggg      240
```

-continued

```
gaaacagctt tgaatgattt tgtggcttca ttaaatgcca ttgccgacac ggcagaccct      300
aaagtcactg gatggtatac cgatctcgaa agtgatgccg tagtcattac gaccttgcgt      360
ggcgggactc ctgctgccga ggaacttgct gagagagcgg gtctcgacga aagagccgtt      420
cggattgtgg aagaagatga agaaccacag agcttggctg caattattgg tggaaacccg      480
tactatgctg gaaattacag atgcagtatc gggtttagtg tccgtcaggg ctctcaaacg      540
ggattcgcga ccgcaggcca ctgcggatcc acggggacgc gtgtgtcttc tccttcagga      600
acagttgcag gaagttattt cccgggtcgc gatatgggct gggtgcggat tacatcagca      660
gatactgtaa caccactcgt aaatcggtat aatgggggaa ctgttacggt cactgggtca      720
caagaagctg ccaccggatc ctccgtttgt cgctctggag caacaacggg ctggcgctgc      780
ggaactatcc aatcaaaaaa tcaaacggtt cgctatgcag aagggactgt tactggttta      840
acaagaacta cagcctgtgc tgaaggtggg gattctggag ggccatggct cacaggtagc      900
caggcgcaag gggttacaag cggcggaaca ggcgattgca gaagtggagg gattaccttt      960
ttccaaccaa tcaatccatt gcttagctat ttcggccttc aattagtgac cggctga      1017
```

<210> SEQ ID NO 30
<211> LENGTH: 1017
<212> TYPE: DNA
<213> ORGANISM: Artificial sequence
<220> FEATURE:
<223> OTHER INFORMATION: Synthetic sequence - Thermobifida fusca (F163R)

<400> SEQUENCE: 30

```
atgcaagagc tggcgttgaa acgggacctc ggcctctctg acgcagaagt agccgaactc       60
cgggctgctg aggcggaagc ggtcgagctc gaggaggagc tccgcgattc attagggtca      120
gacttcggcg gtgtatatct ggatgctgac accaccgaaa ttacggtcgc ggtaaccgac      180
ccggcagcgg taagtcgtgt cgacgcggat gatgtcacag ttgatgttgt cgatttcggg      240
gaaacagctt tgaatgattt tgtggcttca ttaaatgcca ttgccgacac ggcagaccct      300
aaagtcactg gatggtatac cgatctcgaa agtgatgccg tagtcattac gaccttgcgt      360
ggcgggactc ctgctgccga ggaacttgct gagagagcgg gtctcgacga aagagccgtt      420
cggattgtgg aagaagatga agaaccacag agcttggctg caattattgg tggaaacccg      480
tactatagag gaaattacag atgcagtatc gggtttagtg tccgtcaggg ctctcaaacg      540
ggattcgcga ccgcaggcca ctgcggatcc acggggacgc gtgtgtcttc tccttcagga      600
acagttgcag gaagttattt cccgggtcgc gatatgggct gggtgcggat tacatcagca      660
gatactgtaa caccactcgt aaatcggtat aatgggggaa ctgttacggt cactgggtca      720
caagaagctg ccaccggatc ctccgtttgt cgctctggag caacaacggg ctggcgctgc      780
ggaactatcc aatcaaaaaa tcaaacggtt cgctatgcag aagggactgt tactggttta      840
acaagaacta cagcctgtgc tgaaggtggg gattctggag ggccatggct cacaggtagc      900
caggcgcaag gggttacaag cggcggaaca ggcgattgca gaagtggagg gattaccttt      960
ttccaaccaa tcaatccatt gcttagctat ttcggccttc aattagtgac cggctga      1017
```

<210> SEQ ID NO 31
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region

<400> SEQUENCE: 31

```
Leu Ala Ala Ile Ile Gly Gly Asn Pro Tyr Tyr Phe Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
            35                  40                  45

Gly Thr Val Ala Gly Ser Tyr Phe Pro Gly Arg Asp Met Gly Trp Val
        50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
                85                  90                  95

Ser Val Cys Arg Ser Gly Ala Thr Thr Gly Trp Arg Cys Gly Thr Ile
            100                 105                 110

Gln Ser Lys Asn Gln Thr Val Arg Tyr Ala Glu Gly Thr Val Thr Gly
            115                 120                 125

Leu Thr Arg Thr Thr Ala Cys Ala Glu Gly Gly Asp Ser Gly Gly Pro
        130                 135                 140

Trp Leu Thr Gly Ser Gln Ala Gln Gly Val Thr Ser Gly Gly Thr Gly
145                 150                 155                 160

Asp Cys Arg Ser Gly Gly Ile Thr Phe Phe Gln Pro Ile Asn Pro Leu
                165                 170                 175

Leu Ser Tyr Phe Gly Leu Gln Leu Val Thr Gly
            180                 185
```

<210> SEQ ID NO 32
<211> LENGTH: 187
<212> TYPE: PRT
<213> ORGANISM: Artificial sequence
<220> FEATURE:
<223> OTHER INFORMATION: Synthetic sequence - Thermobifida fusca_mature
       region (F12Y)

<400> SEQUENCE: 32

```
Leu Ala Ala Ile Ile Gly Gly Asn Pro Tyr Tyr Tyr Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
            35                  40                  45

Gly Thr Val Ala Gly Ser Tyr Phe Pro Gly Arg Asp Met Gly Trp Val
        50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
                85                  90                  95

Ser Val Cys Arg Ser Gly Ala Thr Thr Gly Trp Arg Cys Gly Thr Ile
            100                 105                 110

Gln Ser Lys Asn Gln Thr Val Arg Tyr Ala Glu Gly Thr Val Thr Gly
            115                 120                 125

Leu Thr Arg Thr Thr Ala Cys Ala Glu Gly Gly Asp Ser Gly Gly Pro
        130                 135                 140

Trp Leu Thr Gly Ser Gln Ala Gln Gly Val Thr Ser Gly Gly Thr Gly
145                 150                 155                 160
```

-continued

```
Asp Cys Arg Ser Gly Gly Ile Thr Phe Phe Gln Pro Ile Asn Pro Leu
            165                 170                 175

Leu Ser Tyr Phe Gly Leu Gln Leu Val Thr Gly
            180                 185

<210> SEQ ID NO 33
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region (F12Y_N116D)

<400> SEQUENCE: 33

Leu Ala Ala Ile Ile Gly Gly Asn Pro Tyr Tyr Tyr Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
        35                  40                  45

Gly Thr Val Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
                85                  90                  95

Ser Val Cys Arg Ser Gly Ala Thr Thr Gly Trp Arg Cys Gly Thr Ile
            100                 105                 110

Gln Ser Lys Asp Gln Thr Val Arg Tyr Ala Glu Gly Thr Val Thr Gly
            115                 120                 125

Leu Thr Arg Thr Thr Ala Cys Ala Glu Gly Gly Asp Ser Gly Gly Pro
    130                 135                 140

Trp Leu Thr Gly Ser Gln Ala Gln Gly Val Thr Ser Gly Gly Thr Gly
145                 150                 155                 160

Asp Cys Arg Ser Gly Gly Ile Thr Phe Phe Gln Pro Ile Asn Pro Leu
            165                 170                 175

Leu Ser Tyr Phe Gly Leu Gln Leu Val Thr Gly
            180                 185

<210> SEQ ID NO 34
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region (F12Y_N116S)

<400> SEQUENCE: 34

Leu Ala Ala Ile Ile Gly Gly Asn Pro Tyr Tyr Tyr Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
        35                  40                  45

Gly Thr Val Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80
```

```
Gly Gly Thr Val Thr Val Thr Gly Ser Gln Glu Ala Ala Thr Gly Ser
            85                  90                  95

Ser Val Cys Arg Ser Gly Ala Thr Thr Gly Trp Arg Cys Gly Thr Ile
            100                 105                 110

Gln Ser Lys Ser Gln Thr Val Arg Tyr Ala Glu Gly Thr Val Thr Gly
        115                 120                 125

Leu Thr Arg Thr Thr Ala Cys Ala Glu Gly Gly Asp Ser Gly Gly Pro
    130                 135                 140

Trp Leu Thr Gly Ser Gln Ala Gln Gly Val Thr Ser Gly Gly Thr Gly
145                 150                 155                 160

Asp Cys Arg Ser Gly Gly Ile Thr Phe Phe Gln Pro Ile Asn Pro Leu
                165                 170                 175

Leu Ser Tyr Phe Gly Leu Gln Leu Val Thr Gly
            180                 185
```

```
<210> SEQ ID NO 35
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region (F12S_N116D)

<400> SEQUENCE: 35

Leu Ala Ala Ile Ile Gly Gly Asn Pro Tyr Tyr Ser Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
        35                  40                  45

Gly Thr Val Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
            85                  90                  95

Ser Val Cys Arg Ser Gly Ala Thr Thr Gly Trp Arg Cys Gly Thr Ile
            100                 105                 110

Gln Ser Lys Asp Gln Thr Val Arg Tyr Ala Glu Gly Thr Val Thr Gly
        115                 120                 125

Leu Thr Arg Thr Thr Ala Cys Ala Glu Gly Gly Asp Ser Gly Gly Pro
    130                 135                 140

Trp Leu Thr Gly Ser Gln Ala Gln Gly Val Thr Ser Gly Gly Thr Gly
145                 150                 155                 160

Asp Cys Arg Ser Gly Gly Ile Thr Phe Phe Gln Pro Ile Asn Pro Leu
                165                 170                 175

Leu Ser Tyr Phe Gly Leu Gln Leu Val Thr Gly
            180                 185
```

```
<210> SEQ ID NO 36
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region (F12S_N116T)

<400> SEQUENCE: 36
```

```
Leu Ala Ala Ile Ile Gly Gly Asn Pro Tyr Tyr Ser Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
        35                  40                  45

Gly Thr Val Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
                85                  90                  95

Ser Val Cys Arg Ser Gly Ala Thr Thr Gly Trp Arg Cys Gly Thr Ile
            100                 105                 110

Gln Ser Lys Thr Gln Thr Val Arg Tyr Ala Glu Gly Thr Val Thr Gly
        115                 120                 125

Leu Thr Arg Thr Thr Ala Cys Ala Glu Gly Gly Asp Ser Gly Gly Pro
    130                 135                 140

Trp Leu Thr Gly Ser Gln Ala Gln Gly Val Thr Ser Gly Gly Thr Gly
145                 150                 155                 160

Asp Cys Arg Ser Gly Gly Ile Thr Phe Phe Gln Pro Ile Asn Pro Leu
            165                 170                 175

Leu Ser Tyr Phe Gly Leu Gln Leu Val Thr Gly
            180                 185
```

```
<210> SEQ ID NO 37
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region (F12A_N116G)

<400> SEQUENCE: 37
```

```
Leu Ala Ala Ile Ile Gly Gly Asn Pro Tyr Tyr Ala Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
        35                  40                  45

Gly Thr Val Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
                85                  90                  95

Ser Val Cys Arg Ser Gly Ala Thr Thr Gly Trp Arg Cys Gly Thr Ile
            100                 105                 110

Gln Ser Lys Gly Gln Thr Val Arg Tyr Ala Glu Gly Thr Val Thr Gly
        115                 120                 125

Leu Thr Arg Thr Thr Ala Cys Ala Glu Gly Gly Asp Ser Gly Gly Pro
    130                 135                 140

Trp Leu Thr Gly Ser Gln Ala Gln Gly Val Thr Ser Gly Gly Thr Gly
145                 150                 155                 160

Asp Cys Arg Ser Gly Gly Ile Thr Phe Phe Gln Pro Ile Asn Pro Leu
```

-continued

```
                 165                 170                 175

Leu Ser Tyr Phe Gly Leu Gln Leu Val Thr Gly
            180                 185

<210> SEQ ID NO 38
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region (F12A)

<400> SEQUENCE: 38

Leu Ala Ala Ile Ile Gly Gly Asn Pro Tyr Tyr Ala Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
        35                  40                  45

Gly Thr Val Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
                85                  90                  95

Ser Val Cys Arg Ser Gly Ala Thr Thr Gly Trp Arg Cys Gly Thr Ile
            100                 105                 110

Gln Ser Lys Asn Gln Thr Val Arg Tyr Ala Glu Gly Thr Val Thr Gly
            115                 120                 125

Leu Thr Arg Thr Thr Ala Cys Ala Glu Gly Gly Asp Ser Gly Gly Pro
    130                 135                 140

Trp Leu Thr Gly Ser Gln Ala Gln Gly Val Thr Ser Gly Gly Thr Gly
145                 150                 155                 160

Asp Cys Arg Ser Gly Gly Ile Thr Phe Phe Gln Pro Ile Asn Pro Leu
            165                 170                 175

Leu Ser Tyr Phe Gly Leu Gln Leu Val Thr Gly
            180                 185

<210> SEQ ID NO 39
<211> LENGTH: 187
<212> TYPE: PRT
<213> ORGANISM: Artificial sequence
<220> FEATURE:
<223> OTHER INFORMATION: Synthetic sequence - Thermobifida fusca_mature
      region (F12R)

<400> SEQUENCE: 39

Leu Ala Ala Ile Ile Gly Gly Asn Pro Tyr Tyr Arg Gly Asn Tyr Arg
1               5                   10                  15

Cys Ser Ile Gly Phe Ser Val Arg Gln Gly Ser Gln Thr Gly Phe Ala
            20                  25                  30

Thr Ala Gly His Cys Gly Ser Thr Gly Thr Arg Val Ser Ser Pro Ser
        35                  40                  45

Gly Thr Val Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
```

-continued

```
                  85                90                95

Ser Val Cys Arg Ser Gly Ala Thr Thr Gly Trp Arg Cys Gly Thr Ile
              100                105                110

Gln Ser Lys Asn Gln Thr Val Arg Tyr Ala Glu Gly Thr Val Thr Gly
          115                120                125

Leu Thr Arg Thr Thr Ala Cys Ala Glu Gly Gly Asp Ser Gly Gly Pro
      130                135                140

Trp Leu Thr Gly Ser Gln Ala Gln Gly Val Thr Ser Gly Gly Thr Gly
145                150                155                160

Asp Cys Arg Ser Gly Gly Ile Thr Phe Phe Gln Pro Ile Asn Pro Leu
              165                170                175

Leu Ser Tyr Phe Gly Leu Gln Leu Val Thr Gly
          180                185

<210> SEQ ID NO 40
<211> LENGTH: 368
<212> TYPE: PRT
<213> ORGANISM: Artificial sequence
<220> FEATURE:
<223> OTHER INFORMATION: Synthetic sequence - Thermobifida fusca

<400> SEQUENCE: 40

Met Asn His Ser Ser Arg Arg Thr Thr Ser Leu Leu Phe Thr Ala Ala
1                5                10                15

Leu Ala Ala Thr Ala Leu Val Ala Ala Thr Thr Pro Ala Ser Ala Gln
              20                25                30

Glu Leu Ala Leu Lys Arg Asp Leu Gly Leu Ser Asp Ala Glu Val Ala
          35                40                45

Glu Leu Arg Ala Ala Glu Ala Glu Ala Val Glu Leu Glu Glu Glu Leu
      50                55                60

Arg Asp Ser Leu Gly Ser Asp Phe Gly Gly Val Tyr Leu Asp Ala Asp
65                70                75                80

Thr Thr Glu Ile Thr Val Ala Val Thr Asp Pro Ala Ala Val Ser Arg
              85                90                95

Val Asp Ala Asp Asp Val Thr Val Asp Val Val Asp Phe Gly Glu Thr
              100                105                110

Ala Leu Asn Asp Phe Val Ala Ser Leu Asn Ala Ile Ala Asp Thr Ala
          115                120                125

Asp Pro Lys Val Thr Gly Trp Tyr Thr Asp Leu Glu Ser Asp Ala Val
      130                135                140

Val Ile Thr Thr Leu Arg Gly Gly Thr Pro Ala Ala Glu Glu Leu Ala
145                150                155                160

Glu Arg Ala Gly Leu Asp Glu Arg Ala Val Arg Ile Val Glu Glu Asp
              165                170                175

Glu Glu Pro Gln Ser Leu Ala Ala Ile Ile Gly Gly Asn Pro Tyr Tyr
          180                185                190

Phe Gly Asn Tyr Arg Cys Ser Ile Gly Phe Ser Val Arg Gln Gly Ser
          195                200                205

Gln Thr Gly Phe Ala Thr Ala Gly His Cys Gly Ser Thr Gly Thr Arg
      210                215                220

Val Ser Ser Pro Ser Gly Thr Val Ala Gly Ser Tyr Phe Pro Gly Arg
225                230                235                240

Asp Met Gly Trp Val Arg Ile Thr Ser Ala Asp Thr Val Thr Pro Leu
              245                250                255

Val Asn Arg Tyr Asn Gly Gly Thr Val Thr Val Thr Gly Ser Gln Glu
```

-continued

```
            260              265              270
Ala Ala Thr Gly Ser Ser Val Cys Arg Ser Gly Ala Thr Thr Gly Trp
        275              280              285
Arg Cys Gly Thr Ile Gln Ser Lys Asn Gln Thr Val Arg Tyr Ala Glu
    290              295              300
Gly Thr Val Thr Gly Leu Thr Arg Thr Thr Ala Cys Ala Glu Gly Gly
305              310              315              320
Asp Ser Gly Gly Pro Trp Leu Thr Gly Ser Gln Ala Gln Gly Val Thr
            325              330              335
Ser Gly Gly Thr Gly Asp Cys Arg Ser Gly Gly Ile Thr Phe Phe Gln
        340              345              350
Pro Ile Asn Pro Leu Leu Ser Tyr Phe Gly Leu Gln Leu Val Thr Gly
        355              360              365
```

<210> SEQ ID NO 41
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12Y)

<400> SEQUENCE: 41

```
ttggctgcaa ttattggtgg aaacccgtac tattacggaa attacagatg cagtatcggg      60
tttagtgtcc gtcagggctc tcaaacggga ttcgcgaccg caggccactg cggatccacg     120
gggacgcgtg tgtcttctcc ttcaggaaca gttgcaggaa gttatttccc gggtcgcgat     180
atgggctggg tgcggattac atcagcagat actgtaacac cactcgtaaa tcggtataat     240
gggggaactg ttacggtcac tgggtcacaa gaagctgcca ccggatcctc cgtttgtcgc     300
tctggagcaa caacgggctg cgctgcgga actatccaat caaaaaacca aacggttcgc      360
tatgcagaag ggactgttac tggtttaaca agaactacag cctgtgctga aggtggggat     420
tctggagggc catggctcac aggtagccag gcgcaagggg ttacaagcgg cggaacaggc     480
gattgcagaa gtggagggat tacctttttc caaccaatca atccattgct tagctatttc     540
ggccttcaat tagtgaccgg ctga                                            564
```

<210> SEQ ID NO 42
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12Y_N116D)

<400> SEQUENCE: 42

```
ttggctgcaa ttattggtgg aaacccgtac tattacggaa attacagatg cagtatcggg      60
tttagtgtcc gtcagggctc tcaaacggga ttcgcgaccg caggccactg cggatccacg     120
gggacgcgtg tgtcttctcc ttcaggaaca gttgcaggaa gttatttccc gggtcgcgat     180
atgggctggg tgcggattac atcagcagat actgtaacac cactcgtaaa tcggtataat     240
gggggaactg ttacggtcac tgggtcacaa gaagctgcca ccggatcctc cgtttgtcgc     300
tctggagcaa caacgggctg cgctgcgga actatccaat caaaagacca aacggttcgc      360
tatgcagaag ggactgttac tggtttaaca agaactacag cctgtgctga aggtggggat     420
tctggagggc catggctcac aggtagccag gcgcaagggg ttacaagcgg cggaacaggc     480
gattgcagaa gtggagggat tacctttttc caaccaatca atccattgct tagctatttc     540
```

-continued

```
ggccttcaat tagtgaccgg ctga                                                    564

<210> SEQ ID NO 43
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12Y_N116S)

<400> SEQUENCE: 43
ttggctgcaa ttattggtgg aaacccgtac tattacggaa attacagatg cagtatcggg      60
tttagtgtcc gtcagggctc tcaaacggga ttcgcgaccg caggccactg cggatccacg     120
gggacgcgtg tgtcttctcc ttcaggaaca gttgcaggaa gttatttccc gggtcgcgat     180
atgggctggg tgcggattac atcagcagat actgtaacac cactcgtaaa tcggtataat     240
gggggaactg ttacggtcac tgggtcacaa gaagctgcca ccggatcctc cgtttgtcgc     300
tctggagcaa caacgggctg cgctgcggga actatccaat caaaaagtca aacggttcgc     360
tatgcagaag ggactgttac tggtttaaca agaactacag cctgtgctga aggtggggat     420
tctggagggc catggctcac aggtagccag gcgcaagggg ttacaagcgg cggaacaggc     480
gattgcagaa gtggagggat tacctttttc caaccaatca atccattgct tagctatttc     540
ggccttcaat tagtgaccgg ctga                                                    564

<210> SEQ ID NO 44
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12S_N116D)

<400> SEQUENCE: 44
ttggctgcaa ttattggtgg aaacccgtac tatagtggaa attacagatg cagtatcggg      60
tttagtgtcc gtcagggctc tcaaacggga ttcgcgaccg caggccactg cggatccacg     120
gggacgcgtg tgtcttctcc ttcaggaaca gttgcaggaa gttatttccc gggtcgcgat     180
atgggctggg tgcggattac atcagcagat actgtaacac cactcgtaaa tcggtataat     240
gggggaactg ttacggtcac tgggtcacaa gaagctgcca ccggatcctc cgtttgtcgc     300
tctggagcaa caacgggctg cgctgcggga actatccaat caaaagatca aacggttcgc     360
tatgcagaag ggactgttac tggtttaaca agaactacag cctgtgctga aggtggggat     420
tctggagggc catggctcac aggtagccag gcgcaagggg ttacaagcgg cggaacaggc     480
gattgcagaa gtggagggat tacctttttc caaccaatca atccattgct tagctatttc     540
ggccttcaat tagtgaccgg ctga                                                    564

<210> SEQ ID NO 45
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12S_N116T)

<400> SEQUENCE: 45
ttggctgcaa ttattggtgg aaacccgtac tatagtggaa attacagatg cagtatcggg      60
tttagtgtcc gtcagggctc tcaaacggga ttcgcgaccg caggccactg cggatccacg     120
```

```
gggacgcgtg tgtcttctcc ttcaggaaca gttgcaggaa gttatttccc gggtcgcgat        180
atgggctggg tgcggattac atcagcagat actgtaacac cactcgtaaa tcggtataat        240
gggggaactg ttacggtcac tgggtcacaa gaagctgcca ccggatcctc cgtttgtcgc        300
tctggagcaa caacgggctg gcgctgcgga actatccaat caaaaactca aacggttcgc        360
tatgcagaag ggactgttac tggtttaaca agaactacag cctgtgctga aggtggggat        420
tctggagggc catggctcac aggtagccag gcgcaagggg ttacaagcgg cggaacaggc        480
gattgcagaa gtggagggat tacctttttc caaccaatca atccattgct tagctatttc        540
ggccttcaat tagtgaccgg ctga                                               564

<210> SEQ ID NO 46
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12A_N116G)

<400> SEQUENCE: 46
ttggctgcaa ttattggtgg aaacccgtac tatgctggaa attacagatg cagtatcggg         60
tttagtgtcc gtcagggctc tcaaacggga ttcgcgaccg caggccactg cggatccacg        120
gggacgcgtg tgtcttctcc ttcaggaaca gttgcaggaa gttatttccc gggtcgcgat        180
atgggctggg tgcggattac atcagcagat actgtaacac cactcgtaaa tcggtataat        240
gggggaactg ttacggtcac tgggtcacaa gaagctgcca ccggatcctc cgtttgtcgc        300
tctggagcaa caacgggctg gcgctgcgga actatccaat caaaaggtca aacggttcgc        360
tatgcagaag ggactgttac tggtttaaca agaactacag cctgtgctga aggtggggat        420
tctggagggc catggctcac aggtagccag gcgcaagggg ttacaagcgg cggaacaggc        480
gattgcagaa gtggagggat tacctttttc caaccaatca atccattgct tagctatttc        540
ggccttcaat tagtgaccgg ctga                                               564

<210> SEQ ID NO 47
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12A)

<400> SEQUENCE: 47
ttggctgcaa ttattggtgg aaacccgtac tatgctggaa attacagatg cagtatcggg         60
tttagtgtcc gtcagggctc tcaaacggga ttcgcgaccg caggccactg cggatccacg        120
gggacgcgtg tgtcttctcc ttcaggaaca gttgcaggaa gttatttccc gggtcgcgat        180
atgggctggg tgcggattac atcagcagat actgtaacac cactcgtaaa tcggtataat        240
gggggaactg ttacggtcac tgggtcacaa gaagctgcca ccggatcctc cgtttgtcgc        300
tctggagcaa caacgggctg gcgctgcgga actatccaat caaaaaatca aacggttcgc        360
tatgcagaag ggactgttac tggtttaaca agaactacag cctgtgctga aggtggggat        420
tctggagggc catggctcac aggtagccag gcgcaagggg ttacaagcgg cggaacaggc        480
gattgcagaa gtggagggat tacctttttc caaccaatca atccattgct tagctatttc        540
ggccttcaat tagtgaccgg ctga                                               564
```

-continued

```
<210> SEQ ID NO 48
<211> LENGTH: 564
<212> TYPE: DNA
<213> ORGANISM: Artificial sequence
<220> FEATURE:
<223> OTHER INFORMATION: Synthetic sequence - Thermobifida fusca_mature
      region (F12R)

<400> SEQUENCE: 48
ttggctgcaa ttattggtgg aaacccgtac tatagaggaa attacagatg cagtatcggg        60
tttagtgtcc gtcagggctc tcaaacggga ttcgcgaccg caggccactg cggatccacg       120
gggacgcgtg tgtcttctcc ttcaggaaca gttgcaggaa gttatttccc gggtcgcgat       180
atgggctggg tgcggattac atcagcagat actgtaacac cactcgtaaa tcggtataat       240
gggggaactg ttacggtcac tgggtcacaa gaagctgcca ccggatcctc cgtttgtcgc       300
tctggagcaa caacgggctg cgctgcgga actatccaat caaaaaatca aacggttcgc        360
tatgcagaag ggactgttac tggtttaaca gaactacag cctgtgctga aggtggggat        420
tctggagggc catggctcac aggtagccag gcgcaagggg ttacaagcgg cggaacaggc       480
gattgcagaa gtggagggat tacctttttc caaccaatca atccattgct tagctatttc       540
ggccttcaat tagtgaccgg ctga                                              564

<210> SEQ ID NO 49
<211> LENGTH: 187
<212> TYPE: PRT
<213> ORGANISM: Artificial sequence
<220> FEATURE:
<223> OTHER INFORMATION: Synthetic sequence - Thermobifida
      cellulosilytica

<400> SEQUENCE: 49

Phe Ala Asp Val Ile Gly Gly Asn Pro Tyr Tyr Phe Gly Gly Tyr Arg
1               5                   10                  15

Cys Ser Ile Gly Phe Ser Val Arg Lys Gly Ser Asp Thr Gly Phe Ala
            20                  25                  30

Thr Ala Gly His Cys Gly Glu Thr Gly Thr Leu Thr Arg Ser Pro Glu
        35                  40                  45

Gly Val Val Ala Gly Ser Tyr Phe Pro Gly Arg Asp Met Gly Trp Val
    50                  55                  60

Arg Leu Thr Gly Ala Asp Thr Val Thr Pro Leu Val Asn Arg Tyr Asp
65                  70                  75                  80

Gly Gly Thr Val Thr Val Thr Gly Ser Gln Glu Ala Val Thr Gly Ser
                85                  90                  95

Ser Val Cys Arg Ser Gly Ser Thr Thr Gly Trp Arg Cys Gly Ile Ile
            100                 105                 110

Gln Ser Lys Asn Gln Thr Val Arg Tyr Ala Glu Gly Thr Val Thr Gly
        115                 120                 125

Leu Thr Arg Thr Thr Ala Cys Ala Glu Ala Gly Asp Ser Gly Gly Pro
    130                 135                 140

Trp Leu Thr Gly Ser Gln Ala Gln Gly Val Thr Ser Gly Gly Ser Gly
145                 150                 155                 160

Asn Cys Arg Thr Gly Gly Ile Thr Tyr Phe Gln Pro Ile Asn Pro Leu
                165                 170                 175

Leu Ser Tyr Phe Gly Leu Glu Leu Val Thr Gly
            180                 185
```

```
<210> SEQ ID NO 50
<211> LENGTH: 187
<212> TYPE: PRT
<213> ORGANISM: Artificial sequence
<220> FEATURE:
<223> OTHER INFORMATION: Synthetic sequence - Thermobifida halotolerans

<400> SEQUENCE: 50

Phe Thr Asp Ile Ile Gly Gly Asn Pro Tyr Tyr Phe Asp Gly Tyr Arg
1               5                   10                  15

Cys Ser Ile Gly Phe Ser Val Arg Arg Gly Ser Glu Ser Gly Phe Ala
            20                  25                  30

Thr Ala Gly His Cys Gly Glu Glu Gly Thr Glu Thr Ser Asp Pro Glu
        35                  40                  45

Gly Thr Val Ala Gly Ala Tyr Phe Pro Gly Arg Asp Met Gly Trp Val
    50                  55                  60

Arg Ile Thr Asp Ala Asp Thr Val Thr Pro Leu Val Asn Arg Tyr Asn
65                  70                  75                  80

Gly Glu Asn Val Thr Val Ala Gly Ser Arg Glu Ala Ala Thr Gly Ser
                85                  90                  95

Ser Val Cys Arg Ser Gly Ser Thr Thr Gly Trp Arg Cys Gly Thr Ile
            100                 105                 110

Arg Ser Lys Asn Gln Thr Val Arg Tyr Ile Glu Gly Thr Val Thr Gly
            115                 120                 125

Leu Thr Arg Thr Thr Ala Cys Ala Glu Gly Gly Asp Ser Gly Gly Pro
    130                 135                 140

Trp Leu Thr Gly Ser Gln Gly Gln Gly Val Thr Ser Gly Gly Ser Gly
145                 150                 155                 160

Asn Cys Thr Leu Gly Gly Val Thr Tyr Phe Gln Pro Leu Asn Pro Leu
                165                 170                 175

Leu Ser His Phe Asp Leu Asp Leu Val Thr Gly
            180                 185

<210> SEQ ID NO 51
<211> LENGTH: 187
<212> TYPE: PRT
<213> ORGANISM: Artificial sequence
<220> FEATURE:
<223> OTHER INFORMATION: Synthetic sequence - Actinorugispora
      endophytica

<400> SEQUENCE: 51

Leu Ala Asn Val Ile Gly Gly Asn Ala Tyr Tyr Phe Gly Gly Tyr Arg
1               5                   10                  15

Cys Ser Val Gly Phe Ser Val Arg His Ser Ser Gly Pro Gly Phe Ala
            20                  25                  30

Thr Ala Gly His Cys Gly Asp Val Gly Thr Arg Thr Thr Ser Pro Thr
        35                  40                  45

Gly Thr Ile Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Ser Tyr Ile Thr Val Thr Gly Ser Ser Glu Ala Ala Asn Gly Ser
                85                  90                  95

Ser Val Cys Arg Ser Gly Ser Thr Thr Gly Trp His Cys Gly Thr Ile
            100                 105                 110

Gln Ser Lys Asn Gln Thr Val Asn Tyr Ala Glu Gly Ser Val Ala Gly
            115                 120                 125
```

```
Leu Thr Arg Thr Thr Ala Cys Ala Glu Gly Gly Asp Ser Gly Gly Ser
    130                 135                 140

Trp Leu Thr Gly Thr Gln Ala Gln Gly Val Thr Ser Gly Gly Ser Gly
145                 150                 155                 160

Asn Cys Thr Trp Gly Gly Thr Thr Tyr Phe Gln Pro Ile Asn Pro Leu
                165                 170                 175

Leu Ser Tyr Phe Asn Leu Thr Leu Val Thr Gly
            180                 185
```

```
<210> SEQ ID NO 52
<211> LENGTH: 183
<212> TYPE: PRT
<213> ORGANISM: Unknown
<220> FEATURE:
<223> OTHER INFORMATION: Spinactinospora alkalitolerans

<400> SEQUENCE: 52
```

```
Phe Ala Asp Ile Ile Gly Gly Asn Ala Tyr Tyr Pro Gly Ser Ser Arg
1               5                   10                  15

Cys Ser Ile Gly Phe Ala Val Gln Gly Gly Phe Val Thr Ala Gly His
            20                  25                  30

Cys Gly Ser Thr Gly Thr Arg Thr Ser Ser Pro Ser Gly Thr Val Ala
        35                  40                  45

Gly Ser Trp Phe Pro Gly Arg Asp Met Gly Trp Val Arg Thr Gly Ser
    50                  55                  60

Gly Asp Thr Pro Arg Pro Trp Val Asn Asn Tyr Arg Gly Gly Tyr Val
65                  70                  75                  80

Thr Val Ala Gly Ser Gln Glu Ala Gly Ile Gly Ser Ser Val Cys Arg
                85                  90                  95

Ser Gly Ser Thr Thr Gly Trp His Cys Gly Thr Ile Gln Ser Lys Asn
            100                 105                 110

Gln Thr Val Arg Tyr Ser Gln Gly Ser Val Tyr Gly Leu Thr Arg Thr
        115                 120                 125

Ser Ala Cys Ala Glu Pro Gly Asp Ser Gly Gly Ser Trp Val Thr Gly
    130                 135                 140

Asn Gln Ala Gln Gly Val Thr Ser Gly Gly Ser Gly Asn Cys Thr Trp
145                 150                 155                 160

Gly Gly Thr Thr Tyr Phe Gln Pro Val Asn Pro Ile Leu Ser Gln Tyr
                165                 170                 175

Gly Leu Arg Leu Val Thr Gly
            180
```

```
<210> SEQ ID NO 53
<211> LENGTH: 186
<212> TYPE: PRT
<213> ORGANISM: Unknown
<220> FEATURE:
<223> OTHER INFORMATION: Nocardiopsis composta

<400> SEQUENCE: 53
```

```
Phe Gly Asp Ile Val Gly Gly Asn Ala Tyr Tyr Pro Gly Gly Ser Arg
1               5                   10                  15

Cys Ser Ile Gly Phe Ser Val Gln Gly Gly Phe Ala Thr Ala Gly His
            20                  25                  30

Cys Gly Ser Gln Gly Thr Arg Val Thr Gly Gly Ala Gly Glu Ser Gly
        35                  40                  45

Thr Val Ala Gly Ser Ile Phe Pro Gly Arg Asp Met Gly Trp Val Arg
```

```
        50                    55                    60

Val Asn Ser Gly Trp Asn Pro Ser Pro Tyr Val Asn Asn Tyr Ser Gly
65                  70                  75                  80

Gly Arg Val Leu Val Thr Gly Ser Gln Glu Ala Ser Val Gly Ala Ser
                85                  90                  95

Val Cys Arg Ser Gly Ser Thr Thr Gly Trp Arg Cys Gly Thr Ile Gln
                100                 105                 110

Ala Lys Asn Gln Thr Val Arg Tyr Pro Glu Gly Thr Val Asn Gly Leu
                115                 120                 125

Thr Arg Thr Thr Ala Cys Ala Glu Pro Gly Asp Ser Gly Gly Ser Trp
            130                 135                 140

Leu Ser Gly Asn Gln Ala Gln Gly Val Thr Ser Gly Gly Ser Gly Asn
145                 150                 155                 160

Cys Ser Ser Gly Gly Thr Thr Phe Phe Gln Pro Leu Asn Pro Ile Leu
                165                 170                 175

Ser Gln Trp Gly Leu Thr Leu Thr Thr Gly
                180                 185
```

<210> SEQ ID NO 54
<211> LENGTH: 186
<212> TYPE: PRT
<213> ORGANISM: Unknown
<220> FEATURE:
<223> OTHER INFORMATION: Nocardiopsis potens

<400> SEQUENCE: 54

```
Phe Gly Asp Ile Val Gly Gly Asn Ala Tyr Tyr Pro Gly Gly Ser Arg
1               5                   10                  15

Cys Ser Ile Gly Phe Ser Val Gln Gly Gly Phe Ala Thr Ala Gly His
                20                  25                  30

Cys Gly Ser Gln Gly Thr Arg Val Thr Gly Gly Ala Gly Glu Ser Gly
            35                  40                  45

Thr Val Ala Gly Ser Ile Phe Pro Gly Arg Asp Met Gly Trp Val Arg
        50                  55                  60

Val Asn Ser Gly Trp Asn Pro Ser Pro Tyr Val Asn Asn Tyr Ser Gly
65                  70                  75                  80

Gly Arg Val Leu Val Thr Gly Ser Gln Glu Ala Ser Val Gly Ala Ser
                85                  90                  95

Ile Cys Arg Ser Gly Ser Thr Thr Gly Trp His Cys Gly Thr Ile Gln
                100                 105                 110

Ala Lys Asn Gln Thr Val Arg Tyr Pro Gln Gly Thr Val Asn Gly Leu
                115                 120                 125

Thr Arg Thr Asn Val Cys Ala Glu Pro Gly Asp Ser Gly Gly Ser Trp
            130                 135                 140

Ile Ser Gly Ser Gln Ala Gln Gly Val Thr Ser Gly Gly Ser Gly Asn
145                 150                 155                 160

Cys Ser Thr Gly Gly Thr Thr Phe Tyr Gln Pro Ile Asn Pro Ile Leu
                165                 170                 175

Ser Gln Trp Gly Leu Thr Leu Thr Thr Gly
                180                 185
```

<210> SEQ ID NO 55
<211> LENGTH: 187
<212> TYPE: PRT
<213> ORGANISM: Artificial sequence
<220> FEATURE:
<223> OTHER INFORMATION: Synthetic sequence - Thermobifida cellulosilytica_F12Y

<400> SEQUENCE: 55

```
Phe Ala Asp Val Ile Gly Gly Asn Pro Tyr Tyr Tyr Gly Gly Tyr Arg
1               5                   10                  15

Cys Ser Ile Gly Phe Ser Val Arg Lys Gly Ser Asp Thr Gly Phe Ala
            20                  25                  30

Thr Ala Gly His Cys Gly Glu Thr Gly Thr Leu Thr Arg Ser Pro Glu
            35                  40                  45

Gly Val Val Ala Gly Ser Tyr Phe Pro Gly Arg Asp Met Gly Trp Val
        50                  55                  60

Arg Leu Thr Gly Ala Asp Thr Val Thr Pro Leu Val Asn Arg Tyr Asp
65                  70                  75                  80

Gly Gly Thr Val Thr Val Thr Gly Ser Gln Glu Ala Val Thr Gly Ser
                85                  90                  95

Ser Val Cys Arg Ser Gly Ser Thr Thr Gly Trp Arg Cys Gly Ile Ile
            100                 105                 110

Gln Ser Lys Asn Gln Thr Val Arg Tyr Ala Glu Gly Thr Val Thr Gly
        115                 120                 125

Leu Thr Arg Thr Thr Ala Cys Ala Glu Ala Gly Asp Ser Gly Gly Pro
        130                 135                 140

Trp Leu Thr Gly Ser Gln Ala Gln Gly Val Thr Ser Gly Gly Ser Gly
145                 150                 155                 160

Asn Cys Arg Thr Gly Gly Ile Thr Tyr Phe Gln Pro Ile Asn Pro Leu
                165                 170                 175

Leu Ser Tyr Phe Gly Leu Glu Leu Val Thr Gly
        180                 185
```

<210> SEQ ID NO 56
<211> LENGTH: 187
<212> TYPE: PRT
<213> ORGANISM: Artificial sequence
<220> FEATURE:
<223> OTHER INFORMATION: Synthetic sequence - Thermobifida
      cellulosilytica_F12YN116D

<400> SEQUENCE: 56

```
Phe Ala Asp Val Ile Gly Gly Asn Pro Tyr Tyr Tyr Gly Gly Tyr Arg
1               5                   10                  15

Cys Ser Ile Gly Phe Ser Val Arg Lys Gly Ser Asp Thr Gly Phe Ala
            20                  25                  30

Thr Ala Gly His Cys Gly Glu Thr Gly Thr Leu Thr Arg Ser Pro Glu
            35                  40                  45

Gly Val Val Ala Gly Ser Tyr Phe Pro Gly Arg Asp Met Gly Trp Val
        50                  55                  60

Arg Leu Thr Gly Ala Asp Thr Val Thr Pro Leu Val Asn Arg Tyr Asp
65                  70                  75                  80

Gly Gly Thr Val Thr Val Thr Gly Ser Gln Glu Ala Val Thr Gly Ser
                85                  90                  95

Ser Val Cys Arg Ser Gly Ser Thr Thr Gly Trp Arg Cys Gly Ile Ile
            100                 105                 110

Gln Ser Lys Asp Gln Thr Val Arg Tyr Ala Glu Gly Thr Val Thr Gly
        115                 120                 125

Leu Thr Arg Thr Thr Ala Cys Ala Glu Ala Gly Asp Ser Gly Gly Pro
        130                 135                 140

Trp Leu Thr Gly Ser Gln Ala Gln Gly Val Thr Ser Gly Gly Ser Gly
```

145                150                155                160

Asn Cys Arg Thr Gly Gly Ile Thr Tyr Phe Gln Pro Ile Asn Pro Leu
                165                170                175

Leu Ser Tyr Phe Gly Leu Glu Leu Val Thr Gly
        180                185

<210> SEQ ID NO 57
<211> LENGTH: 187
<212> TYPE: PRT
<213> ORGANISM: Artificial sequence
<220> FEATURE:
<223> OTHER INFORMATION: Synthetic sequence - Thermobifida
      halotolerans_F12Y

<400> SEQUENCE: 57

Phe Thr Asp Ile Ile Gly Gly Asn Pro Tyr Tyr Tyr Asp Gly Tyr Arg
1                5                10                15

Cys Ser Ile Gly Phe Ser Val Arg Arg Gly Ser Glu Ser Gly Phe Ala
                20                25                30

Thr Ala Gly His Cys Gly Glu Glu Gly Thr Glu Thr Ser Asp Pro Glu
        35                40                45

Gly Thr Val Ala Gly Ala Tyr Phe Pro Gly Arg Asp Met Gly Trp Val
        50                55                60

Arg Ile Thr Asp Ala Asp Thr Val Thr Pro Leu Val Asn Arg Tyr Asn
65                70                75                80

Gly Glu Asn Val Thr Val Ala Gly Ser Arg Glu Ala Ala Thr Gly Ser
                85                90                95

Ser Val Cys Arg Ser Gly Ser Thr Thr Gly Trp Arg Cys Gly Thr Ile
                100                105                110

Arg Ser Lys Asn Gln Thr Val Arg Tyr Ile Glu Gly Thr Val Thr Gly
        115                120                125

Leu Thr Arg Thr Thr Ala Cys Ala Glu Gly Gly Asp Ser Gly Gly Pro
        130                135                140

Trp Leu Thr Gly Ser Gln Gly Gln Gly Val Thr Ser Gly Gly Ser Gly
145                150                155                160

Asn Cys Thr Leu Gly Gly Val Thr Tyr Phe Gln Pro Leu Asn Pro Leu
                165                170                175

Leu Ser His Phe Asp Leu Asp Leu Val Thr Gly
        180                185

<210> SEQ ID NO 58
<211> LENGTH: 187
<212> TYPE: PRT
<213> ORGANISM: Artificial sequence
<220> FEATURE:
<223> OTHER INFORMATION: Synthetic sequence - Thermobifida
      halotolerans_F12YN116D

<400> SEQUENCE: 58

Phe Thr Asp Ile Ile Gly Gly Asn Pro Tyr Tyr Tyr Asp Gly Tyr Arg
1                5                10                15

Cys Ser Ile Gly Phe Ser Val Arg Arg Gly Ser Glu Ser Gly Phe Ala
                20                25                30

Thr Ala Gly His Cys Gly Glu Glu Gly Thr Glu Thr Ser Asp Pro Glu
        35                40                45

Gly Thr Val Ala Gly Ala Tyr Phe Pro Gly Arg Asp Met Gly Trp Val
        50                55                60

Arg Ile Thr Asp Ala Asp Thr Val Thr Pro Leu Val Asn Arg Tyr Asn

-continued

```
65              70              75              80

Gly Glu Asn Val Thr Val Ala Gly Ser Arg Glu Ala Ala Thr Gly Ser
                85              90              95

Ser Val Cys Arg Ser Gly Ser Thr Thr Gly Trp Arg Cys Gly Thr Ile
            100             105             110

Arg Ser Lys Asp Gln Thr Val Arg Tyr Ile Glu Gly Thr Val Thr Gly
        115             120             125

Leu Thr Arg Thr Thr Ala Cys Ala Glu Gly Gly Asp Ser Gly Gly Pro
    130             135             140

Trp Leu Thr Gly Ser Gln Gly Gln Gly Val Thr Ser Gly Gly Ser Gly
145             150             155             160

Asn Cys Thr Leu Gly Gly Val Thr Tyr Phe Gln Pro Leu Asn Pro Leu
            165             170             175

Leu Ser His Phe Asp Leu Asp Leu Val Thr Gly
        180             185
```

<210> SEQ ID NO 59
<211> LENGTH: 187
<212> TYPE: PRT
<213> ORGANISM: Artificial sequence
<220> FEATURE:
<223> OTHER INFORMATION: Synthetic sequence - Actinorugispora
      endophytica_F12Y

<400> SEQUENCE: 59

```
Leu Ala Asn Val Ile Gly Gly Asn Ala Tyr Tyr Tyr Gly Gly Tyr Arg
1               5               10              15

Cys Ser Val Gly Phe Ser Val Arg His Ser Ser Gly Pro Gly Phe Ala
            20              25              30

Thr Ala Gly His Cys Gly Asp Val Gly Thr Arg Thr Thr Ser Pro Thr
        35              40              45

Gly Thr Ile Ala Gly Ser Tyr Phe Pro Gly Arg Asp Met Gly Trp Val
    50              55              60

Arg Ile Thr Ser Ala Asp Thr Val Thr Pro Leu Val Asn Arg Tyr Asn
65              70              75              80

Gly Ser Tyr Ile Thr Val Thr Gly Ser Ser Glu Ala Ala Asn Gly Ser
                85              90              95

Ser Val Cys Arg Ser Gly Ser Thr Thr Gly Trp His Cys Gly Thr Ile
            100             105             110

Gln Ser Lys Asn Gln Thr Val Asn Tyr Ala Glu Gly Ser Val Ala Gly
        115             120             125

Leu Thr Arg Thr Thr Ala Cys Ala Glu Gly Gly Asp Ser Gly Gly Ser
    130             135             140

Trp Leu Thr Gly Thr Gln Ala Gln Gly Val Thr Ser Gly Gly Ser Gly
145             150             155             160

Asn Cys Thr Trp Gly Gly Thr Thr Tyr Phe Gln Pro Ile Asn Pro Leu
            165             170             175

Leu Ser Tyr Phe Asn Leu Thr Leu Val Thr Gly
        180             185
```

<210> SEQ ID NO 60
<211> LENGTH: 187
<212> TYPE: PRT
<213> ORGANISM: Artificial sequence
<220> FEATURE:
<223> OTHER INFORMATION: Synthetic sequence - Actinorugispora
      endophytica_F12YN116D

```
<400> SEQUENCE: 60

Leu Ala Asn Val Ile Gly Gly Asn Ala Tyr Tyr Tyr Gly Gly Tyr Arg
1               5                   10                  15

Cys Ser Val Gly Phe Ser Val Arg His Ser Ser Gly Pro Gly Phe Ala
                20                  25                  30

Thr Ala Gly His Cys Gly Asp Val Gly Thr Arg Thr Thr Ser Pro Thr
                35                  40                  45

Gly Thr Ile Ala Gly Ser Tyr Phe Pro Gly Arg Asp Met Gly Trp Val
    50                  55                  60

Arg Ile Thr Ser Ala Asp Thr Val Thr Pro Leu Val Asn Arg Tyr Asn
65                  70                  75                  80

Gly Ser Tyr Ile Thr Val Thr Gly Ser Ser Glu Ala Ala Asn Gly Ser
                85                  90                  95

Ser Val Cys Arg Ser Gly Ser Thr Thr Gly Trp His Cys Gly Thr Ile
                100                 105                 110

Gln Ser Lys Asp Gln Thr Val Asn Tyr Ala Glu Gly Ser Val Ala Gly
                115                 120                 125

Leu Thr Arg Thr Thr Ala Cys Ala Glu Gly Gly Asp Ser Gly Gly Ser
    130                 135                 140

Trp Leu Thr Gly Thr Gln Ala Gln Gly Val Thr Ser Gly Gly Ser Gly
145                 150                 155                 160

Asn Cys Thr Trp Gly Gly Thr Thr Tyr Phe Gln Pro Ile Asn Pro Leu
                165                 170                 175

Leu Ser Tyr Phe Asn Leu Thr Leu Val Thr Gly
                180                 185

<210> SEQ ID NO 61
<211> LENGTH: 183
<212> TYPE: PRT
<213> ORGANISM: Artificial sequence
<220> FEATURE:
<223> OTHER INFORMATION: Synthetic sequence - Spinactinospora
      alkalitolerans_F12Y

<400> SEQUENCE: 61

Phe Ala Asp Ile Ile Gly Gly Asn Ala Tyr Tyr Tyr Gly Ser Ser Arg
1               5                   10                  15

Cys Ser Ile Gly Phe Ala Val Gln Gly Gly Phe Val Thr Ala Gly His
                20                  25                  30

Cys Gly Ser Thr Gly Thr Arg Thr Ser Ser Pro Ser Gly Thr Val Ala
        35                  40                  45

Gly Ser Trp Phe Pro Gly Arg Asp Met Gly Trp Val Arg Thr Gly Ser
    50                  55                  60

Gly Asp Thr Pro Arg Pro Trp Val Asn Asn Tyr Arg Gly Gly Tyr Val
65                  70                  75                  80

Thr Val Ala Gly Ser Gln Glu Ala Gly Ile Gly Ser Ser Val Cys Arg
                85                  90                  95

Ser Gly Ser Thr Thr Gly Trp His Cys Gly Thr Ile Gln Ser Lys Asn
                100                 105                 110

Gln Thr Val Arg Tyr Ser Gln Gly Ser Val Tyr Gly Leu Thr Arg Thr
                115                 120                 125

Ser Ala Cys Ala Glu Pro Gly Asp Ser Gly Gly Ser Trp Val Thr Gly
    130                 135                 140

Asn Gln Ala Gln Gly Val Thr Ser Gly Gly Ser Gly Asn Cys Thr Trp
145                 150                 155                 160
```

-continued

```
Gly Gly Thr Thr Tyr Phe Gln Pro Val Asn Pro Ile Leu Ser Gln Tyr
            165                 170                 175

Gly Leu Arg Leu Val Thr Gly
            180

<210> SEQ ID NO 62
<211> LENGTH: 183
<212> TYPE: PRT
<213> ORGANISM: Artificial sequence
<220> FEATURE:
<223> OTHER INFORMATION: Synthetic sequence - Spinactinospora
      alkalitolerans_F12YN116D

<400> SEQUENCE: 62

Phe Ala Asp Ile Ile Gly Gly Asn Ala Tyr Tyr Tyr Gly Ser Ser Arg
1               5                   10                  15

Cys Ser Ile Gly Phe Ala Val Gln Gly Gly Phe Val Thr Ala Gly His
            20                  25                  30

Cys Gly Ser Thr Gly Thr Arg Thr Ser Ser Pro Ser Gly Thr Val Ala
        35                  40                  45

Gly Ser Trp Phe Pro Gly Arg Asp Met Gly Trp Val Arg Thr Gly Ser
    50                  55                  60

Gly Asp Thr Pro Arg Pro Trp Val Asn Asn Tyr Arg Gly Gly Tyr Val
65                  70                  75                  80

Thr Val Ala Gly Ser Gln Glu Ala Gly Ile Gly Ser Ser Val Cys Arg
                85                  90                  95

Ser Gly Ser Thr Thr Gly Trp His Cys Gly Thr Ile Gln Ser Lys Asp
            100                 105                 110

Gln Thr Val Arg Tyr Ser Gln Gly Ser Val Tyr Gly Leu Thr Arg Thr
            115                 120                 125

Ser Ala Cys Ala Glu Pro Gly Asp Ser Gly Gly Ser Trp Val Thr Gly
    130                 135                 140

Asn Gln Ala Gln Gly Val Thr Ser Gly Gly Ser Gly Asn Cys Thr Trp
145                 150                 155                 160

Gly Gly Thr Thr Tyr Phe Gln Pro Val Asn Pro Ile Leu Ser Gln Tyr
            165                 170                 175

Gly Leu Arg Leu Val Thr Gly
            180

<210> SEQ ID NO 63
<211> LENGTH: 186
<212> TYPE: PRT
<213> ORGANISM: Artificial sequence
<220> FEATURE:
<223> OTHER INFORMATION: Synthetic sequence - Nocardiopsis composta_F12Y

<400> SEQUENCE: 63

Phe Gly Asp Ile Val Gly Gly Asn Ala Tyr Tyr Tyr Gly Gly Ser Arg
1               5                   10                  15

Cys Ser Ile Gly Phe Ser Val Gln Gly Gly Phe Ala Thr Ala Gly His
            20                  25                  30

Cys Gly Ser Gln Gly Thr Arg Val Thr Gly Gly Ala Gly Glu Ser Gly
        35                  40                  45

Thr Val Ala Gly Ser Ile Phe Pro Gly Arg Asp Met Gly Trp Val Arg
    50                  55                  60

Val Asn Ser Gly Trp Asn Pro Ser Pro Tyr Val Asn Asn Tyr Ser Gly
65                  70                  75                  80

Gly Arg Val Leu Val Thr Gly Ser Gln Glu Ala Ser Val Gly Ala Ser
```

-continued

```
                85                  90                  95

Val Cys Arg Ser Gly Ser Thr Thr Gly Trp Arg Cys Gly Thr Ile Gln
            100                 105                 110

Ala Lys Asn Gln Thr Val Arg Tyr Pro Glu Gly Thr Val Asn Gly Leu
        115                 120                 125

Thr Arg Thr Thr Ala Cys Ala Glu Pro Gly Asp Ser Gly Gly Ser Trp
    130                 135                 140

Leu Ser Gly Asn Gln Ala Gln Gly Val Thr Ser Gly Gly Ser Gly Asn
145                 150                 155                 160

Cys Ser Ser Gly Gly Thr Thr Phe Phe Gln Pro Leu Asn Pro Ile Leu
            165                 170                 175

Ser Gln Trp Gly Leu Thr Leu Thr Thr Gly
            180                 185

<210> SEQ ID NO 64
<211> LENGTH: 186
<212> TYPE: PRT
<213> ORGANISM: Artificial sequence
<220> FEATURE:
<223> OTHER INFORMATION: Synthetic sequence - Nocardiopsis
      composta_F12YN116D

<400> SEQUENCE: 64

Phe Gly Asp Ile Val Gly Gly Asn Ala Tyr Tyr Tyr Gly Gly Ser Arg
1               5                   10                  15

Cys Ser Ile Gly Phe Ser Val Gln Gly Gly Phe Ala Thr Ala Gly His
            20                  25                  30

Cys Gly Ser Gln Gly Thr Arg Val Thr Gly Gly Ala Gly Glu Ser Gly
        35                  40                  45

Thr Val Ala Gly Ser Ile Phe Pro Gly Arg Asp Met Gly Trp Val Arg
    50                  55                  60

Val Asn Ser Gly Trp Asn Pro Ser Pro Tyr Val Asn Asn Tyr Ser Gly
65                  70                  75                  80

Gly Arg Val Leu Val Thr Gly Ser Gln Glu Ala Ser Val Gly Ala Ser
            85                  90                  95

Val Cys Arg Ser Gly Ser Thr Thr Gly Trp Arg Cys Gly Thr Ile Gln
            100                 105                 110

Ala Lys Asp Gln Thr Val Arg Tyr Pro Glu Gly Thr Val Asn Gly Leu
        115                 120                 125

Thr Arg Thr Thr Ala Cys Ala Glu Pro Gly Asp Ser Gly Gly Ser Trp
    130                 135                 140

Leu Ser Gly Asn Gln Ala Gln Gly Val Thr Ser Gly Gly Ser Gly Asn
145                 150                 155                 160

Cys Ser Ser Gly Gly Thr Thr Phe Phe Gln Pro Leu Asn Pro Ile Leu
            165                 170                 175

Ser Gln Trp Gly Leu Thr Leu Thr Thr Gly
            180                 185

<210> SEQ ID NO 65
<211> LENGTH: 186
<212> TYPE: PRT
<213> ORGANISM: Artificial sequence
<220> FEATURE:
<223> OTHER INFORMATION: Synthetic sequence - Nocardiopsis potens_F12Y

<400> SEQUENCE: 65

Phe Gly Asp Ile Val Gly Gly Asn Ala Tyr Tyr Tyr Gly Gly Ser Arg
1               5                   10                  15
```

```
Cys Ser Ile Gly Phe Ser Val Gln Gly Gly Phe Ala Thr Ala Gly His
        20                  25                  30

Cys Gly Ser Gln Gly Thr Arg Val Thr Gly Gly Ala Gly Glu Ser Gly
        35                  40                  45

Thr Val Ala Gly Ser Ile Phe Pro Gly Arg Asp Met Gly Trp Val Arg
    50                  55                  60

Val Asn Ser Gly Trp Asn Pro Ser Pro Tyr Val Asn Asn Tyr Ser Gly
65                  70                  75                  80

Gly Arg Val Leu Val Thr Gly Ser Gln Glu Ala Ser Val Gly Ala Ser
                85                  90                  95

Ile Cys Arg Ser Gly Ser Thr Thr Gly Trp His Cys Gly Thr Ile Gln
            100                 105                 110

Ala Lys Asn Gln Thr Val Arg Tyr Pro Gln Gly Thr Val Asn Gly Leu
        115                 120                 125

Thr Arg Thr Asn Val Cys Ala Glu Pro Gly Asp Ser Gly Gly Ser Trp
    130                 135                 140

Ile Ser Gly Ser Gln Ala Gln Gly Val Thr Ser Gly Gly Ser Gly Asn
145                 150                 155                 160

Cys Ser Thr Gly Gly Thr Thr Phe Tyr Gln Pro Ile Asn Pro Ile Leu
                165                 170                 175

Ser Gln Trp Gly Leu Thr Leu Thr Thr Gly
            180                 185
```

```
<210> SEQ ID NO 66
<211> LENGTH: 186
<212> TYPE: PRT
<213> ORGANISM: Artificial sequence
<220> FEATURE:
<223> OTHER INFORMATION: Synthetic sequence - Nocardiopsis
      potens_F12YN116D
```

```
<400> SEQUENCE: 66
```

```
Phe Gly Asp Ile Val Gly Gly Asn Ala Tyr Tyr Tyr Gly Gly Ser Arg
1                   5                   10                  15

Cys Ser Ile Gly Phe Ser Val Gln Gly Gly Phe Ala Thr Ala Gly His
        20                  25                  30

Cys Gly Ser Gln Gly Thr Arg Val Thr Gly Gly Ala Gly Glu Ser Gly
        35                  40                  45

Thr Val Ala Gly Ser Ile Phe Pro Gly Arg Asp Met Gly Trp Val Arg
    50                  55                  60

Val Asn Ser Gly Trp Asn Pro Ser Pro Tyr Val Asn Asn Tyr Ser Gly
65                  70                  75                  80

Gly Arg Val Leu Val Thr Gly Ser Gln Glu Ala Ser Val Gly Ala Ser
                85                  90                  95

Ile Cys Arg Ser Gly Ser Thr Thr Gly Trp His Cys Gly Thr Ile Gln
            100                 105                 110

Ala Lys Asp Gln Thr Val Arg Tyr Pro Gln Gly Thr Val Asn Gly Leu
        115                 120                 125

Thr Arg Thr Asn Val Cys Ala Glu Pro Gly Asp Ser Gly Gly Ser Trp
    130                 135                 140

Ile Ser Gly Ser Gln Ala Gln Gly Val Thr Ser Gly Gly Ser Gly Asn
145                 150                 155                 160

Cys Ser Thr Gly Gly Thr Thr Phe Tyr Gln Pro Ile Asn Pro Ile Leu
                165                 170                 175

Ser Gln Trp Gly Leu Thr Leu Thr Thr Gly
```

-continued

```
                 180               185

<210> SEQ ID NO 67
<211> LENGTH: 374
<212> TYPE: PRT
<213> ORGANISM: Unknown
<220> FEATURE:
<223> OTHER INFORMATION: Thermobifida cellulosilytica

<400> SEQUENCE: 67

Met Asn Arg Pro Ser Thr Arg Arg Thr Val Arg Ala Leu Leu Thr Ala
1               5                   10                  15

Ala Leu Ala Ala Thr Ala Leu Thr Ala Pro Ala Ala Pro Ser Leu Ala
            20                  25                  30

Gln Glu Ala Ser Gln Glu Ala Ala Leu Thr Arg Asp Leu Asp Leu Thr
        35                  40                  45

Gly Thr Glu Val Ala Leu Leu Arg Ala Ala Glu Ser Glu Ala Met Asp
    50                  55                  60

Arg Glu Glu Glu Leu Ser Ala Val Leu Gly Ser Asp Phe Gly Gly Val
65                  70                  75                  80

Tyr Leu Ala Pro Glu Thr Gly Glu Val Thr Val Ala Val Thr Asp Pro
                85                  90                  95

Ala Ala Val Pro Val Val Glu Gln Ser Gly Ala Thr Ala Gln Val Val
            100                 105                 110

Thr Phe Gly Glu Thr Ala Leu Asn Asp Phe Val Asp Ser Leu Asn Ala
            115                 120                 125

Val Ala Asp Arg Ala Asp Glu Gln Ile Thr Gly Trp Tyr Thr Asp Leu
    130                 135                 140

Ala Ala Asp Thr Val Val Ile Thr Ala Phe Pro Gly Gly Ser Ala Ala
145                 150                 155                 160

Ala Glu Glu Leu Ala Ala Leu Ala Gly Val Asp Glu Arg Ala Val Arg
                165                 170                 175

Val Thr Glu Ser Ala Ala Arg Pro Gln Leu Phe Ala Asp Val Ile Gly
            180                 185                 190

Gly Asn Pro Tyr Tyr Phe Gly Gly Tyr Arg Cys Ser Ile Gly Phe Ser
            195                 200                 205

Val Arg Lys Gly Ser Asp Thr Gly Phe Ala Thr Ala Gly His Cys Gly
    210                 215                 220

Glu Thr Gly Thr Leu Thr Arg Ser Pro Glu Gly Val Val Ala Gly Ser
225                 230                 235                 240

Tyr Phe Pro Gly Arg Asp Met Gly Trp Val Arg Leu Thr Gly Ala Asp
                245                 250                 255

Thr Val Thr Pro Leu Val Asn Arg Tyr Asp Gly Gly Thr Val Thr Val
            260                 265                 270

Thr Gly Ser Gln Glu Ala Val Thr Gly Ser Ser Val Cys Arg Ser Gly
    275                 280                 285

Ser Thr Thr Gly Trp Arg Cys Gly Ile Ile Gln Ser Lys Asn Gln Thr
    290                 295                 300

Val Arg Tyr Ala Glu Gly Thr Val Thr Gly Leu Thr Arg Thr Thr Ala
305                 310                 315                 320

Cys Ala Glu Ala Gly Asp Ser Gly Gly Pro Trp Leu Thr Gly Ser Gln
                325                 330                 335

Ala Gln Gly Val Thr Ser Gly Gly Ser Gly Asn Cys Arg Thr Gly Gly
            340                 345                 350

Ile Thr Tyr Phe Gln Pro Ile Asn Pro Leu Leu Ser Tyr Phe Gly Leu
```

```
          355                 360                 365

Glu Leu Val Thr Gly Ala
    370

<210> SEQ ID NO 68
<211> LENGTH: 354
<212> TYPE: PRT
<213> ORGANISM: Unknown
<220> FEATURE:
<223> OTHER INFORMATION: Thermobifida halotolerans

<400> SEQUENCE: 68

Met Val Ala Thr Ala Leu Thr Ala Ser Ala Thr Pro Ala Ser Ala Asp
1               5                   10                  15

Arg His Asp Ala Leu Lys Arg Asp Leu Gly Leu Thr Asp Ser Glu Val
                20                  25                  30

Ala Arg Leu Arg Thr Ala Glu Thr Glu Ala Met Asp Arg Glu Ala Glu
            35                  40                  45

Leu Arg Asp Thr Leu Gly Ser Asp Phe Gly Gly Val His Leu Asp Ala
    50                  55                  60

Ala Ser Gly Glu Leu Thr Ile Ala Val Thr Asp Pro Glu Ala Val Pro
65                  70                  75                  80

Thr Val Glu Arg Ala Gly Ala Asn Ala Glu Val Val Thr Phe Gly Glu
                85                  90                  95

Ser Ala Leu Asn Gly Phe Val Asp Ser Leu Asn Ser Val Ala Asp Gln
            100                 105                 110

Ala Asp Glu Gln Val Thr Gly Trp Tyr Ala Asp Ile Ala Asp Asp Ser
            115                 120                 125

Val Val Ile Thr Val Arg Glu Gly Gly Thr Ala Ala Ala Glu Ala Leu
    130                 135                 140

Val Ala Arg Ala Gly Val Asp Glu Arg Ala Val Arg Val Thr Lys Ser
145                 150                 155                 160

Asp Glu Arg Pro Gln Leu Phe Thr Asp Ile Ile Gly Gly Asn Pro Tyr
                165                 170                 175

Tyr Phe Asp Gly Tyr Arg Cys Ser Ile Gly Phe Ser Val Arg Arg Gly
            180                 185                 190

Ser Glu Ser Gly Phe Ala Thr Ala Gly His Cys Gly Glu Glu Gly Thr
            195                 200                 205

Glu Thr Ser Asp Pro Glu Gly Thr Val Ala Gly Ala Tyr Phe Pro Gly
    210                 215                 220

Arg Asp Met Gly Trp Val Arg Ile Thr Asp Ala Asp Thr Val Thr Pro
225                 230                 235                 240

Leu Val Asn Arg Tyr Asn Gly Glu Asn Val Thr Val Ala Gly Ser Arg
                245                 250                 255

Glu Ala Ala Thr Gly Ser Ser Val Cys Arg Ser Gly Ser Thr Thr Gly
            260                 265                 270

Trp Arg Cys Gly Thr Ile Arg Ser Lys Asn Gln Thr Val Arg Tyr Ile
            275                 280                 285

Glu Gly Thr Val Thr Gly Leu Thr Arg Thr Thr Ala Cys Ala Glu Gly
    290                 295                 300

Gly Asp Ser Gly Gly Pro Trp Leu Thr Gly Ser Gln Gly Gln Gly Val
305                 310                 315                 320

Thr Ser Gly Gly Ser Gly Asn Cys Thr Leu Gly Gly Val Thr Tyr Phe
            325                 330                 335

Gln Pro Leu Asn Pro Leu Leu Ser His Phe Asp Leu Asp Leu Val Thr
```

-continued

```
            340             345             350

Gly Ala

<210> SEQ ID NO 69
<211> LENGTH: 383
<212> TYPE: PRT
<213> ORGANISM: Unknown
<220> FEATURE:
<223> OTHER INFORMATION: Actinorugispora endophytica

<400> SEQUENCE: 69

Met Lys Arg Ser Ser Val Phe Arg Ala Leu Gly Gly Thr Ile Leu Thr
1               5                   10                  15

Ala Gly Leu Val Ile Thr Ala Ala Pro Phe Ala Ser Ala Ala Pro Val
                20                  25                  30

His Thr Glu Thr Thr Pro Thr Ala Ala Glu Ala Gly Asp Gln Leu Ser
            35                  40                  45

Ala Leu Lys Arg Asp Leu Gly Leu Ser Thr Ala Glu Val Glu Glu Leu
        50                  55                  60

Gln Ala Ala Glu Ala Glu Ala Met Asp Val Glu Glu Gly Leu Arg Glu
65                  70                  75                  80

Thr Leu Gly Ser Asp Phe Gly Gly Ala His Phe Asp Ile Asp Ser Gly
                85                  90                  95

Glu Leu Thr Val Ser Val Thr Asp Ala Ala Ala Val Ser Thr Val Glu
            100                 105                 110

Ala Ala Gly Ala Asn Ala Glu Val Val Asp Phe Gly Glu Pro Ala Leu
        115                 120                 125

Asp Ala Ile Val Glu Asp Leu Asn Thr Val Ala Glu Glu Ala Asp Asp
    130                 135                 140

Ser Val Thr Gly Trp Tyr Val Asp Thr Ala Asp Asp Ser Val Val Ile
145                 150                 155                 160

Thr Val Leu Glu Gly Asp Thr Glu Ala Ala Glu Ala Leu Val Ala Glu
                165                 170                 175

Ala Asp Val Asp Gly Lys Ala Val Arg Val Glu Glu Thr Thr Glu Gln
            180                 185                 190

Pro Lys Leu Leu Ala Asn Val Ile Gly Gly Asn Ala Tyr Tyr Phe Gly
        195                 200                 205

Gly Tyr Arg Cys Ser Val Gly Phe Ser Val Arg His Ser Ser Gly Pro
    210                 215                 220

Gly Phe Ala Thr Ala Gly His Cys Gly Asp Val Gly Thr Arg Thr Thr
225                 230                 235                 240

Ser Pro Thr Gly Thr Ile Ala Gly Ser Tyr Phe Pro Gly Arg Asp Met
                245                 250                 255

Gly Trp Val Arg Ile Thr Ser Ala Asp Thr Val Thr Pro Leu Val Asn
            260                 265                 270

Arg Tyr Asn Gly Ser Tyr Ile Thr Val Thr Gly Ser Ser Glu Ala Ala
        275                 280                 285

Asn Gly Ser Ser Val Cys Arg Ser Gly Ser Thr Thr Gly Trp His Cys
    290                 295                 300

Gly Thr Ile Gln Ser Lys Asn Gln Thr Val Asn Tyr Ala Glu Gly Ser
305                 310                 315                 320

Val Ala Gly Leu Thr Arg Thr Thr Ala Cys Ala Glu Gly Gly Asp Ser
                325                 330                 335

Gly Gly Ser Trp Leu Thr Gly Thr Gln Ala Gln Gly Val Thr Ser Gly
            340                 345                 350
```

```
Gly Ser Gly Asn Cys Thr Trp Gly Gly Thr Thr Tyr Phe Gln Pro Ile
        355                 360                 365

Asn Pro Leu Leu Ser Tyr Phe Asn Leu Thr Leu Val Thr Gly Ala
    370                 375                 380

<210> SEQ ID NO 70
<211> LENGTH: 375
<212> TYPE: PRT
<213> ORGANISM: Unknown
<220> FEATURE:
<223> OTHER INFORMATION: Spinactinospora alkalitolerans

<400> SEQUENCE: 70

Met Arg Lys Ser Pro Ile Ile Arg Ala Val Gly Gly Ala Ala Ile Thr
1                   5                   10                  15

Phe Gly Leu Val Ile Ala Ala Ala Pro Phe Ala Ser Ala Asp Ser Gly
            20                  25                  30

Ser Glu Thr Thr Ala Gly Ser Val Gly Gln Leu Gly Ala Met Gln Arg
        35                  40                  45

Asp Leu Gly Leu Ser Ala Thr Glu Ala Thr Ala Leu Leu Asp Gln Glu
    50                  55                  60

Glu Gln Ala Arg Thr Leu Glu Gly Glu Leu Arg Glu Thr Leu Gly Gly
65                  70                  75                  80

Asp Phe Gly Gly Ala Val Phe Asp Ile Glu Ser Gly Glu Leu Thr Val
            85                  90                  95

Ser Val Thr Asp Glu Asp Ala Val Asp Glu Val Arg Glu Ala Gly Ala
            100                 105                 110

Glu Ala Glu Val Val Thr Tyr Gly Glu Gln Arg Leu Asp Ala Ile Val
        115                 120                 125

Asp Asp Leu Asn Ala Thr Glu Asp Thr Ala Asp Glu Ser Val Thr Gly
    130                 135                 140

Trp Tyr Val Asp Thr Ala Asp Asp Ser Val Val Val Thr Val Met Glu
145                 150                 155                 160

Gly Glu Glu Ala Ala Ala Glu Lys Leu Ile Ala Thr Ala Asp Val Glu
            165                 170                 175

Gly Thr Ala Val Arg Val Glu Glu Thr Thr Glu Gln Pro Glu Thr Phe
            180                 185                 190

Ala Asp Ile Ile Gly Gly Asn Ala Tyr Tyr Pro Gly Ser Ser Arg Cys
        195                 200                 205

Ser Ile Gly Phe Ala Val Gln Gly Gly Phe Val Thr Ala Gly His Cys
    210                 215                 220

Gly Ser Thr Gly Thr Arg Thr Ser Ser Pro Ser Gly Thr Val Ala Gly
225                 230                 235                 240

Ser Trp Phe Pro Gly Arg Asp Met Gly Trp Val Arg Thr Gly Ser Gly
            245                 250                 255

Asp Thr Pro Arg Pro Trp Val Asn Asn Tyr Arg Gly Gly Tyr Val Thr
            260                 265                 270

Val Ala Gly Ser Gln Glu Ala Gly Ile Gly Ser Ser Val Cys Arg Ser
        275                 280                 285

Gly Ser Thr Thr Gly Trp His Cys Gly Thr Ile Gln Ser Lys Asn Gln
    290                 295                 300

Thr Val Arg Tyr Ser Gln Gly Ser Val Tyr Gly Leu Thr Arg Thr Ser
305                 310                 315                 320

Ala Cys Ala Glu Pro Gly Asp Ser Gly Gly Ser Trp Val Thr Gly Asn
            325                 330                 335
```

```
Gln Ala Gln Gly Val Thr Ser Gly Gly Ser Gly Asn Cys Thr Trp Gly
        340             345             350

Gly Thr Thr Tyr Phe Gln Pro Val Asn Pro Ile Leu Ser Gln Tyr Gly
        355             360             365

Leu Arg Leu Val Thr Gly Ala
    370             375

<210> SEQ ID NO 71
<211> LENGTH: 376
<212> TYPE: PRT
<213> ORGANISM: Unknown
<220> FEATURE:
<223> OTHER INFORMATION: Nocardiopsis composta

<400> SEQUENCE: 71

Met Arg Lys Ser Pro Tyr Ile Pro Leu Leu Gly Ala Ser Val Leu Ala
1               5               10              15

Leu Gly Met Ile Ala Ala Ser Pro Thr Ala Ala Ser Ala Asp Glu Ala
            20              25              30

Thr Asp Ser Ser Pro Ala Arg Ala Leu Ala Ser Gly Leu Asp Met Ser
        35              40              45

Thr Ala Gln Ala Ala Glu Leu Leu Asp Ala Glu Ala Gln Ala Arg Thr
    50              55              60

Ala Glu Gln Glu Ala Arg Glu Leu Ala Gly Ala Ser Phe Ala Gly Ala
65              70              75              80

Val Phe Asp Ala Asp Thr Arg Lys Leu Thr Val Ser Val Thr Asp Ala
            85              90              95

Ala Ala Ala Glu Ala Val Gln Ala Thr Gly Ala Glu Thr Arg Val Val
            100             105             110

Glu Ala Ser Ala Asp Glu Leu Asp Ala Ala Val Ala Asp Leu Asn Ala
        115             120             125

Glu Glu Arg Gly Leu Gly Ser Glu Ile Asp Gly Val Thr Gly Trp Tyr
    130             135             140

Val Asp Gln Ala Ala Asn Glu Leu Val Val Thr Val Leu Asp Gly Glu
145             150             155             160

Thr Glu Ala Ala Glu Thr Leu Leu Asp Glu Ala Gly Val Asp Ser Val
            165             170             175

Pro Val Arg Val Asp Gln Gly Ala Glu Gln Pro Glu Thr Phe Gly Asp
            180             185             190

Ile Val Gly Gly Asn Ala Tyr Tyr Pro Gly Gly Ser Arg Cys Ser Ile
        195             200             205

Gly Phe Ser Val Gln Gly Gly Phe Ala Thr Ala Gly His Cys Gly Ser
    210             215             220

Gln Gly Thr Arg Val Thr Gly Gly Ala Gly Glu Ser Gly Thr Val Ala
225             230             235             240

Gly Ser Ile Phe Pro Gly Arg Asp Met Gly Trp Val Arg Val Asn Ser
            245             250             255

Gly Trp Asn Pro Ser Pro Tyr Val Asn Asn Tyr Ser Gly Gly Arg Val
            260             265             270

Leu Val Thr Gly Ser Gln Glu Ala Ser Val Gly Ala Ser Val Cys Arg
        275             280             285

Ser Gly Ser Thr Thr Gly Trp Arg Cys Gly Thr Ile Gln Ala Lys Asn
    290             295             300

Gln Thr Val Arg Tyr Pro Glu Gly Thr Val Asn Gly Leu Thr Arg Thr
305             310             315             320
```

```
Thr Ala Cys Ala Glu Pro Gly Asp Ser Gly Gly Ser Trp Leu Ser Gly
            325             330             335

Asn Gln Ala Gln Gly Val Thr Ser Gly Gly Ser Gly Asn Cys Ser Ser
            340             345             350

Gly Gly Thr Thr Phe Phe Gln Pro Leu Asn Pro Ile Leu Ser Gln Trp
            355             360             365

Gly Leu Thr Leu Thr Thr Gly Ala
    370             375

<210> SEQ ID NO 72
<211> LENGTH: 376
<212> TYPE: PRT
<213> ORGANISM: Unknown
<220> FEATURE:
<223> OTHER INFORMATION: Nocardiopsis potens

<400> SEQUENCE: 72

Met Arg Lys Ser Pro Tyr Ile Ser Phe Leu Gly Ala Ser Ala Leu Ala
1               5               10              15

Leu Gly Met Ile Ala Ala Ser Pro Ala Ala Ala Ser Ala Asp Glu Ala
            20              25              30

Ala Asp Thr Ser Pro Ala Glu Ala Leu Ala Ser Gly Leu Asp Met Ser
            35              40              45

Ala Ser Gln Ala Ala Asp Leu Leu Asp Ala Glu Ala Glu Ala Arg Gly
    50              55              60

Thr Glu Ala Glu Ala Arg Glu Ala Ala Gly Gly Ser Phe Ala Gly Ala
65              70              75              80

Val Phe Asp Ala Glu Ser Gln Val Leu Thr Val Ser Val Thr Asp Ala
            85              90              95

Ala Ala Ala Glu Ala Val Glu Ala Thr Gly Ala Glu Thr Arg Val Val
            100             105             110

Glu Ala Ser Glu Asp Glu Leu Asp Ser Ala Val Ser Asp Leu Asn Ala
            115             120             125

Glu Glu Ser Ser Leu Gly Ser Ala Ile Glu Gly Val Thr Gly Trp Tyr
    130             135             140

Val Asp Pro Ala Ala Asn Glu Val Val Val Thr Val Leu Asp Gly Glu
145             150             155             160

Thr Ala Ala Ala Glu Thr Leu Leu Asp Glu Ala Gly Val Asp Gly Val
            165             170             175

Pro Val Arg Ile Asp Glu Gly Ala Glu Gln Pro Glu Thr Phe Gly Asp
            180             185             190

Ile Val Gly Gly Asn Ala Tyr Tyr Pro Gly Gly Ser Arg Cys Ser Ile
            195             200             205

Gly Phe Ser Val Gln Gly Gly Phe Ala Thr Ala Gly His Cys Gly Ser
    210             215             220

Gln Gly Thr Arg Val Thr Gly Gly Ala Gly Glu Ser Gly Thr Val Ala
225             230             235             240

Gly Ser Ile Phe Pro Gly Arg Asp Met Gly Trp Val Arg Val Asn Ser
            245             250             255

Gly Trp Asn Pro Ser Pro Tyr Val Asn Asn Tyr Ser Gly Gly Arg Val
            260             265             270

Leu Val Thr Gly Ser Gln Glu Ala Ser Val Gly Ala Ser Ile Cys Arg
    275             280             285

Ser Gly Ser Thr Thr Gly Trp His Cys Gly Thr Ile Gln Ala Lys Asn
    290             295             300
```

-continued

```
Gln Thr Val Arg Tyr Pro Gln Gly Thr Val Asn Gly Leu Thr Arg Thr
305             310             315             320

Asn Val Cys Ala Glu Pro Gly Asp Ser Gly Gly Ser Trp Ile Ser Gly
                325             330             335

Ser Gln Ala Gln Gly Val Thr Ser Gly Gly Ser Gly Asn Cys Ser Thr
            340             345             350

Gly Gly Thr Thr Phe Tyr Gln Pro Ile Asn Pro Ile Leu Ser Gln Trp
        355             360             365

Gly Leu Thr Leu Thr Thr Gly Ala
    370             375
```

SERINE PROTEASE VARIANT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_493USPC_SEQUENCE_LISTING.txt. The text file is 128,963 bytes, was created on Oct. 12, 2022, and is being submitted electronically via EFS-Web.

TECHNICAL FIELD

The present disclosure relates to a novel serine protease variant.

BACKGROUND ART

Proteases are involved in various functions such as digestion, absorption, and defense in living organisms and are classified into serine proteases, cysteine proteases, aspartic proteases, and metalloproteases according to the structures of active sites. Among these, serine proteases (or serine endopeptidases) are enzymes characterized by having in common an active serine residue in their active sites, which cleave peptide bonds in proteins, in which serine serves as a nucleophilic amino acid at a protease's active site (Hedstrom, 2002. *Chem Rev* 102:4501-4524).

Serine proteases have been used in a wide variety of applications. In addition to therapeutic applications to treat human diseases such as lysis of blood clots, serine proteases are used not only as ingredients of laundry detergents and contact lens cleaners, but also in modification of milk proteins, silk degumming, soaking of leather, unhairing, synthesis of oligopeptides, recovery of silver from lung X-ray films, production and improvement of feeds and foods (Korean Patent Publication No. 10-2005-0068750), and the like.

DISCLOSURE

Technical Problem

There is a need to develop a serine protease having improved thermal stability, increased activity, and the like to obtain higher industrial cost-effectiveness and efficiency.

Technical Solution

An object of the present disclosure is to provide a serine protease variant.

Another object of the present disclosure is to provide a polynucleotide encoding the serine protease variant and a vector including the same.

Still another object of the present disclosure is to provide a microorganism including one or more of the serine protease variant; a polynucleotide encoding the serine protease variant; or a vector including the polynucleotide.

Still another object of the present disclosure is to provide a feed composition including one or more of the serine protease variant or a microorganism expressing the serine protease variant.

Advantageous Effects

The serine protease variant of the present disclosure has superior activity compared to the existing serine protease, and thus can be usefully used industrially.

BRIEF DESCRIPTION OF DRAWINGS

FIG. 1 illustrates the position of the residue in which a mutation is introduced into the tertiary structure of the serine protease variant derived from *Thermobifida fusca.*

DETAILED DESCRIPTION OF THE INVENTION

The present disclosure will be described in detail. Meanwhile, each description and embodiment disclosed in the present disclosure may be applied herein to other descriptions and embodiments. In other words, all combinations of various components disclosed in the present disclosure are included within the scope of the present disclosure. Furthermore, the scope of the present disclosure should not be limited by the descriptions provided below.

Additionally, those skilled in the art may recognize or be able to confirm, using no more than routine experimentation, many equivalents to specific embodiments of the present disclosure described in the present disclosure. Such equivalents are intended to be encompassed in the present disclosure.

An aspect of the present disclosure provides a serine protease variant.

As used herein, the term "serine protease" refers to an enzyme that belongs to a sub-group of a protease and has a proteolytic activity. Specifically, the serine protease may be an enzyme that degrades proteins by hydrolyzing peptide bonds, and basically has an active serine residue at active sites thereof, and more specifically an enzyme that has a spatial arrangement of amino acid residues of histidine, aspartate, and serine, which can be referred to as a catalytic triad, but is not limited thereto.

The serine protease according to the present disclosure may be derived from a microorganism of the genus *Thermobifida*, the genus *Nocardiopsis*, the genus *Actinorugispora*, or the genus *Spinactinospora*, but is not limited thereto. Specifically, in the present disclosure, the wild type of the serine protease may be a serine protease derived from *Thermobifida fusca, Thermobifida cellulosilytica, Thermobifda halotolerans, Actinorugispora endophytica, Spinactinospora alkalitolerans, Nocardiopsis composta,* or *Nocardiopsis potens,* but is not limited thereto.

In an embodiment, the serine protease of the present disclosure may be a polypeptide including, consisting essentially of, or consisting of the amino acid sequence set forth in SEQ ID NO: 31, but is not limited thereto. In an embodiment, the amino acid sequence of SEQ ID NO: 31 may be an amino acid sequence derived from SEQ ID NO: 40 or SEQ ID NO: 2, but is not limited thereto.

In an embodiment, the serine protease of the present disclosure may include, consist essentially of, or consist of the amino acid sequence of any one of SEQ ID NOS: 49 to 54, but is not limited thereto. In an embodiment, the amino acid sequences of SEQ ID NOS: 49 to 54 may be derived from the amino acid sequences of any one of SEQ ID NOS: 67 to 72, but is not limited thereto.

The serine protease of the present disclosure may include any sequence having the same activity as that of the amino acid sequences described above, without limitation. In addition, the serine protease may include, consist essentially of, or consist of the amino acid sequence of any one of SEQ ID NOS: 31 and 49 to 54 or an amino acid sequence having 60% or more homology or identity therewith, but is not limited thereto. Specifically, the amino acid sequence may include any one of the amino acid sequences set forth in SEQ ID NOS: 31 and 49 to 54 or an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with any one of the amino acid sequences set forth in SEQ ID NOS: 31 and 49 to 54. Additionally, it is obvious that any protein having an amino acid sequence including deletion, modification, substitution, or addition in part of the sequence is within the scope of the present disclosure as long as the amino acid sequence has such homologies or identities described above and an effect equivalent to that of the protein.

In other words, although the expressions "protein or polypeptide including an amino acid sequence set forth in a predetermined SEQ ID NO:" and "protein or polypeptide including an amino acid sequence set forth in a predetermined SEQ ID NO:" are used in the present disclosure, it is obvious that any protein having an amino acid sequence including deletion, modification, substitution, or addition in part of the sequence may also be used in the present disclosure as long as the protein has an activity identical or equivalent to that of a polypeptide consisting of the corresponding amino acid sequence. For example, it is obvious that the "polypeptide including an amino acid sequence of SEQ ID NO: 31" belongs to the "polypeptide consisting of the amino acid sequence of SEQ ID NO: 31" as long as the former has an activity identical or equivalent to that of the latter.

As used herein, the term "homology" or "identity" refers to a degree of relatedness between two given amino acid sequences or nucleotide sequences and may be shown as a percentage. The terms homology and identity may be used interchangeably.

Sequence homology or identity of conserved polynucleotides or polypeptides may be determined by standard alignment algorithm and default gap penalties established by a program being used may be used together.

Substantially, homologous or identical sequences may generally hybridize with each other along the entire length or at least about 50%, 60%, 70%, 80% or 90% of the entire sequence under moderate or highly stringent conditions.

Polynucleotides including degenerated codons instead of codons are also considered in hybridization.

The sequence homology, similarity, or identity between any two given polynucleotides or polypeptides may be determined using a known computer algorithm such as "FASTA" program using default parameters as introduced by, for example, Pearson et al. (1988) *Proc. Natl. Acad. Sci. USA* 85:2444. Alternatively, the Needleman-Wunsch algorithm (Needleman and Wunsch, 1970, *J. Mol. Biol.* 48:443-453) performed in the Needleman program of the European Molecular Biology Open Software Suite (EMBOSS) package (Rice et al., 2000, *Trends Genet.* 16:276-277) (version 5.0.0 or later) may be used to determine the same (including GCG program package (Devereux, J. et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST from The National Center for Biotechnology Information database, or ClustalW.

The homology, similarity, or identity between polynucleotides or polypeptides may be determined by comparing sequence information using, for example, a GAP computer program, such as a program introduced by Needleman et al. (1970), *J Mol Biol.* 48:443 as disclosed in, for example, Smith and Waterman, *Adv. Appl. Math* (1981) 2:482. In brief, the GAP program defines similarity as the number of aligned symbols (namely, nucleotides or amino acids), which are similar, divided by the total number of symbols in a shorter of two sequences. Default parameters for the GAP program may include: (1) a binary comparison matrix (containing a value of 1 for identity and 0 for non-identity) and a weighted comparison matrix of Gribskov et al. (1986) *Nucl. Acids Res.* 14:6745 as disclosed in Schwartz and Dayhoff, eds., *Atlas Of Protein Sequence And Structure*, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps.

In addition, the sequence homology, similarity, or identity between any two given polynucleotides or polypeptides may be confirmed by comparing sequences thereof by a southern hybridization test under defined stringent conditions, and the defined proper hybridization conditions are within the scope of the technology and may be determined by a method well known to those skilled in the art.

In an embodiment, the serine protease variant provided in the present disclosure may refer to a variant in which an amino acid at a specific position is substituted so as to have an enzyme activity exceeding 100% compared to that of the protein before mutation, among the above-described proteins having the serine protease activity.

In a specific embodiment, the variant provided in the present disclosure may have an enzyme activity exceeding 100%, specifically an increased enzymatic activity of about 110%, about 120%, about 130%, about 140%, about 150%, about 160%, about 170%, about 180%, about 190%, or about 200% or more compared to that of the wild-type enzyme including the amino acid sequence of any one of SEQ ID NOS: 31 and 49 to 54, but is not limited thereto.

The term "about" is a range including all of ±0.5, ±0.4, ±0.3, ±0.2, ±0.1, and the like, and includes all numerical values in the range equivalent to or similar to the numerical value following the term about, but is not limited thereto.

As used herein, the term "variant" refers to a polypeptide obtained by conservative substitution and/or modification of one or more amino acids different from that of the recited sequence while retaining the functions or properties of the protein. A variant is different from the identified sequence due to substitution, deletion, or addition of several amino acids. Such a variant may generally be identified by modifying one of the polypeptide sequences and evaluating properties of the modified polypeptide. That is, the ability of a variant may be enhanced, unchanged, or diminished compared to that of a native protein.

In addition, some variants may include variants in which one or more portions such as an N-terminal leader sequence or transmembrane domain are removed. Other variants may include variants in which a portion is removed from or added to the N- and/or C-terminus of a mature protein.

The term "variant" may also be used interchangeably with other terms such as modification, modified protein, modified polypeptide, mutant, mutein, and divergent, and any terms used to indicate variation may also be used without limitation.

The variant may have an activity of the modified protein enhanced compared to that of natural wild-type or non-modified proteins, but is not limited thereto.

As used herein, the term "conservative substitution" refers to substitution of one amino acid with another amino acid having similar structural and/or chemical properties. For example, the variant may have one or more conservative substitutions while still retaining one or more biological activities. Such amino acid substitution may generally occur based on similarity of polarity, charge, solubility, hydrophobicity, hydrophilicity, and/or amphipathic nature of a residue. For example, among electrically charged amino acids with side chains, positively charged (basic) amino acids include arginine, lysine, and histidine and negatively charged (acidic) amino acids include glutamate and aspartate; among uncharged amino acids with side chains, non-polar amino acids include glycine, alanine, valine, leucine, isoleucine, methionine, phenylalanine, tryptophan and proline and polar or hydrophilic amino acids include serine, threonine, cysteine, tyrosine, asparagine and glutamine; and among the amino acids, aromatic amino acids include phenylalanine, tryptophan and tyrosine. The variant may also include deletion or addition of amino acids having minimum influence on the properties and secondary structure of a polypeptide. For example, a polypeptide may be conjugated to a signal (or leader) sequence of the N-terminus of a protein involved in transfer of the protein co-translationally or post-translationally. The polypeptide may also be conjugated to another sequence or linker to identify, purify, or synthesize the polypeptide As used herein, the term "serine protease variant" refers to a polypeptide including substitution of one or more amino acids in an amino acid sequence of a polypeptide having serine protease activity.

The serine protease variant according to the present disclosure may include substitution of amino acids at positions corresponding to the 12th amino acid and/or 116th amino acid from the N-terminus of the amino acid sequence of SEQ ID NO: 31 with other amino acids. Specifically, the serine protease variant may include substitution of amino acids corresponding to the 12th amino acid and/or 116th amino acid of SEQ ID NO: 31, and may include an amino acid sequence having 60% or more and less than 100% homology or identity with the amino acid sequence of any one of SEQ ID NOS: 31 and 49 to 54.

In an embodiment, the serine protease variant of the present disclosure may include substitution of amino acids at positions corresponding to the 12th amino acid and/or 116th amino acid of SEQ ID NO: 31, and may have 60% or more, for example, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more, and less than 100% homology or identity with the amino acid sequence of any one of SEQ ID NOS: 31 and 49 to 54, but is not limited thereto.

Meanwhile, since the 12th amino acid and 116th amino acid from the N-terminus of SEQ ID NO: 31 correspond to the 12th amino acid and 116th amino acid from the N-terminus of SEQ ID NOS: 49 to 54, the description of the positions of the amino acids based on SEQ ID NO: 31 may be equally applied to the 12th amino acid and 116th amino acid of the amino acid sequence of any one of SEQ ID NOS: 49 to 54.

In an embodiment, the serine protease variant of the present disclosure may include substitution of amino acids at positions corresponding to the 12th amino acid and/or 116th amino acid of SEQ ID NO: 54, and may include an amino acid sequence having 60% or more, for example, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more, and less than 100% homology or identity with the amino acid sequence of any one of SEQ ID NOS: 52 to 54. Specifically, the serine protease variant may include substitution of an amino acid at a position corresponding to the 12th amino acid of SEQ ID NO: 54, and may have 60% or more, for example, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more, and less than 100% homology or identity with the amino acid sequence of SEQ ID NO: 54, but is not limited thereto.

In an embodiment, the serine protease variant of the present disclosure may be a protein in which amino acids corresponding to position 12, position 116, or positions 12 and 116 from the N-terminus in the amino acid sequence of any one selected from SEQ ID NOS: 31 and 49 to 54 are all substituted with other amino acids. The "other amino acids" refer to amino acids different from those before the substitution, and are not limited as long as they are amino acids other than the amino acids before the substitution.

In an embodiment, the serine protease variant according to the present disclosure may be a variant in which phenylalanine at position 12 in the amino acid sequence of any one selected from SEQ ID NOS: 31 and 49 to 51 is substituted with glycine, alanine, arginine, aspartate, cysteine, glutamate, asparagine, glutamine, histidine, proline, serine, tyrosine, isoleucine, leucine, lysine, tryptophan, valine, methionine, or threonine; and/or asparagine at position 116 is substituted with glycine, alanine, arginine, aspartate, cysteine, glutamate, glutamine, histidine, proline, serine, tyrosine, isoleucine, leucine, lysine, phenylalanine, tryptophan, valine, methionine, or threonine, but is not limited thereto.

In an embodiment, the serine protease variant according to the present disclosure may be a variant in which proline at position 12 in the amino acid sequence of any one selected from SEQ ID NOS: 52 to 54 is substituted with phenylalanine, glycine, alanine, arginine, aspartate, cysteine, glutamate, asparagine, glutamine, histidine, serine, tyrosine, isoleucine, leucine, lysine, tryptophan, valine, methionine, or threonine; and/or asparagine at position 116 is substituted with glycine, alanine, arginine, aspartate, cysteine, glutamate, glutamine, histidine, proline, serine, tyrosine, isoleucine, leucine, lysine, phenylalanine, tryptophan, valine, methionine, or threonine, but is not limited thereto.

Specifically, the variant may be a protein in which an amino acid corresponding to position 12 in the amino acid sequence of any one selected from SEQ ID NOS: 31 and 49 to 54 is substituted with tyrosine (Y), serine (S), alanine (A), or arginine (R); an amino acid corresponding to position 116 is substituted with aspartate (D), serine (S), threonine (T), or glycine (G); or amino acids at positions 12 and 116 in the amino acid sequence of SEQ ID NO: 31 are substituted with tyrosine (Y) and aspartate (D), tyrosine (Y) and serine (S), serine (S) and aspartate (D), serine (S) and threonine (T), or alanine (A) and glycine (G), respectively, but is not limited thereto. In an embodiment, the serine protease variant may be a variant in which proline at position 12 in the amino acid sequence of any one selected from SEQ ID NOS: 52 to 54 is substituted with tyrosine, alanine, serine or arginine, but is not limited thereto.

It is obvious that the variant, in which the amino acids at position 12 and/or position 116 in the amino acid sequence of any one selected from SEQ ID NOS: 31 and 49 to 54 are substituted with other amino acids, includes variants in which the amino acids corresponding to the positions are substituted with other amino acids.

Additionally, the variant also includes variants in which the amino acids at positions corresponding to the 12th amino acid and/or 116th amino acid from the N-terminus of the amino acid sequence of any one selected from SEQ ID NOS: 31 and 49 to 54 are substituted with other amino acids in the above-described amino acid sequence set forth in any one selected from SEQ ID NOS: 31 and 49 to 54 or an amino acid sequence having at least 60% or more, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with the amino acid sequence of any one selected from SEQ ID NOS: 31 and 49 to 54.

In an embodiment, among the variants, the variant, in which the amino acids at positions corresponding to the 12th amino acid and/or 116th amino acid in the amino acid sequence of SEQ ID NO: 31 are substituted with other amino acids, may include, consist essentially of, or consist of an amino acid sequence set forth in any one selected from SEQ ID NOS: 32 to 39, but is not limited thereto. In an embodiment, among the variants, the variant, in which the amino acids at positions corresponding to the 12th amino acid and/or 116th amino acid in the amino acid sequence of SEQ ID NO: 49 are substituted with other amino acids, may include, consist essentially of, or consist of the amino acid sequence of SEQ ID NO: 55 or 56, but is not limited thereto.

In an embodiment, among the variants, the variant, in which the amino acids at positions corresponding to the 12th amino acid and/or 116th amino acid in the amino acid sequence of SEQ ID NO: 50 are substituted with other amino acids, may include, consist essentially of, or consist of the amino acid sequence of SEQ ID NO: 57 or 58, but is not limited thereto.

In an embodiment, among the variants, the variant, in which the amino acids at positions corresponding to the 12th amino acid and/or 116th amino acid in the amino acid sequence of SEQ ID NO: 51 are substituted with other amino acids, may include, consist essentially of, or consist of the amino acid sequence of SEQ ID NO: 59 or 60, but is not limited thereto.

In an embodiment, among the variants, the variant, in which the amino acids at positions corresponding to the 12th amino acid and/or 116th amino acid in the amino acid sequence of SEQ ID NO: 52 are substituted with other amino acids, may include, consist essentially of, or consist of the amino acid sequence of SEQ ID NO: 61 or 62, but is not limited thereto.

In an embodiment, among the variants, the variant, in which the amino acids at positions corresponding to the 12th amino acid and/or 116th amino acid in the amino acid sequence of SEQ ID NO: 53 are substituted with other amino acids, may include, consist essentially of, or consist of the amino acid sequence of SEQ ID NO: 63 or 64, but is not limited thereto.

In an embodiment, among the variants, the variant, in which the amino acids at positions corresponding to the 12th amino acid and/or 116th amino acid in the amino acid sequence of SEQ ID NO: 54 are substituted with other amino acids, may include, consist essentially of, or consist of the amino acid sequence of SEQ ID NO: 65 or 66, but is not limited thereto.

In an embodiment, the serine protease variant according to the present disclosure may include substitution with other amino acids at positions corresponding to position 12 and/or position 116 of the amino acid sequence of any one selected from SEQ ID NOS: 31 and 49 to 54; may have 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more, and less than 100% sequence homology to the amino acid sequence of any one selected from SEQ ID NOS: 31 and 49 to 54; and may have serine protease activity.

The serine protease variant of the present disclosure may have an activity enhanced compared to that of a polypeptide before modification, a natural wild-type polypeptide, or a non-modified polypeptide, but is not limited thereto. In addition, it is obvious that any protein including an amino acid sequence having deletion, modification, substitution, or addition in part of the sequence is within the scope of the present disclosure as long as the protein has the above-described homology and an effect equivalent to that of the protein.

In addition, it is obvious that any variant having addition of a meaningless sequence in the forward or reverse direction of the amino acid sequence of the corresponding SEQ ID NO or a naturally occurring mutation, or a silent mutation thereof, in addition to the mutations in the 12th amino acid and/or 116th amino acid or mutations at positions corresponding thereto, are not excluded from but included within the scope of the present disclosure, as long as the variant has an activity identical or equivalent to that of the variant according to the present disclosure.

Meanwhile, a mature region of NCBI Reference Sequence WP_016188200.1 (SEQ ID NO: 40) corresponds to the amino acid sequence of SEQ ID NO: 31 of the present disclosure, and the sequence excluding the signal peptide from SEQ ID NO: 40 corresponds to SEQ ID NO: 2 of the present disclosure.

It is obvious as described above that the serine protease variant of the present disclosure may include deletion or addition of amino acids having minimum influence on the properties and secondary structure of the serine protease, in which the amino acids at positions corresponding to 12 and/or 116 of SEQ ID NO: 31 are substituted with other amino acids. In addition, it would be obvious to those skilled in the art, through a sequence alignment well known in the art, that position 12 and position 116 from the N-terminus of SEQ ID NO: 31 according to the present disclosure correspond to positions 193 and 297 in SEQ ID NO: 40 and positions 163 and 267 in SEQ ID NO: 2, and that SEQ ID NO: 31 is included in SEQ ID NO: 2 and SEQ ID NO: 40.

Thus, with respect to the amino acid sequences of SEQ ID NOS: 2 and 40 each including the amino acid sequence of SEQ ID NO: 31, the serine protease variant of the present disclosure includes a variant in which the amino acids at positions corresponding to 12 and 116 of SEQ ID NO: 31 (the 163rd amino acid and/or 267th amino acid of SEQ ID NO: 2 and the 193rd amino acid and/or 297th amino acid of SEQ ID NO: 40) are substituted. Additionally, the descriptions of SEQ ID NO: 31 and the 12th amino acid and 116th amino acid thereof may also be applied to SEQ ID NO: 2 and the 163rd amino acid and/or 267th amino acid thereof and SEQ ID NO: 40 and the 193rd amino acid and/or 297th amino acid thereof.

In an embodiment, the serine protease variant of the present disclosure may include an amino acid sequence in which amino acids at positions corresponding to 12 and/or 116 of SEQ ID NO: 31 are substituted with other amino acids, and may have at least 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more, and less than 100% sequence homology to SEQ ID NO: 2. In another embodiment, the serine protease variant of the present disclosure may include substitution of the 163rd amino acid and/or 267th amino acid of SEQ ID NO: 2 with other amino acids, and may have 60% or more and less than 100% sequence homology to SEQ ID NO: 2, and may have 60% or more sequence homology to the amino acid sequence of any one selected from SEQ ID NOS: 3 to 10, but is not limited thereto.

Meanwhile, it is obvious that a variant including the substitution of amino acids corresponding to position 12 and/or position 116 from the N-terminus of SEQ ID NOS: 49 to 54 in a polypeptide including the amino acid sequence of any one of SEQ ID NOS: 49 to 54 is also included in the scope of serine proteases of the present disclosure.

The sequence of the polypeptide including the amino acid sequence of any one of SEQ ID NOS: 49 to 54 may be, for example, an amino acid sequence described in GenBank Accession: KUP96625.1 (SEQ ID NO: 67), NCBI Reference Sequence: WP_068687914.1 (SEQ ID NO: 68), NCBI Reference Sequence: WP_133739400.1 (SEQ ID NO: 69), NCBI Reference Sequence: WP_179641868.1 (SEQ ID NO: 70), NCBI Reference Sequence: WP_184391208.1 (SEQ ID NO: 71), NCBI Reference Sequence: WP_017594871.1 (SEQ ID NO: 72), or the like.

Those skilled in the art can identify amino acids corresponding to position 12 and/or position 116 from the N-terminus of SEQ ID NOS: 49 to 54 in SEQ ID NOS: 67 to 72 through sequence alignment known in the art, and apply the description of position 12 and/or position 116 from the N-terminus of SEQ ID NOS: 49 to 54.

In an embodiment, the serine protease variant of the present disclosure may include substitution of amino acids corresponding to position 12 and/or position 116 from the N-terminus of the amino acid sequence of any one of SEQ ID NOS: 49 to 54 with other amino acids, and may have 60% or more, for example, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with the amino acid sequence of any one of SEQ ID NOS: 67 to 72.

In an embodiment, the serine protease variant of the present disclosure may include substitution of the amino acid corresponding to position 12 based on the amino acid sequence set forth in SEQ ID NO: 54, and may have 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with the amino acid sequence set forth in any one of SEQ ID NOS: 70 to 72. As an example, the serine protease variant may further include substitution of the amino acid corresponding to position 116 based on the amino acid sequence set forth in SEQ ID NO: 54.

In an embodiment, the serine protease variant of the present disclosure may include substitution of the amino acid corresponding to position 198 based on the amino acid sequence set forth in SEQ ID NO: 67. The variant may have 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with SEQ ID NO: 67. For example, the variant may include an amino acid sequence in which an amino acid at a position corresponding to the 12th amino acid of SEQ ID NO: 49 is substituted with another amino acid and has 70% or more sequence identity with SEQ ID NO: 49. As an example, the serine protease variant may further include substitution of the amino acid corresponding to position 302 based on the amino acid sequence set forth in SEQ ID NO: 67.

In an embodiment, the serine protease variant of the present disclosure may include substitution of the amino acid corresponding to position 178 based on the amino acid sequence set forth in SEQ ID NO: 68. The variant may have 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with SEQ ID NO: 68. For example, the variant may include an amino acid sequence in which an amino acid at a position corresponding to the 12th amino acid of SEQ ID NO: 50 is substituted with another amino acid and has 70% or more sequence identity with SEQ ID NO: 50. As an example, the serine protease variant may further include substitution of the amino acid corresponding to position 282 based on the amino acid sequence set forth in SEQ ID NO: 68.

In an embodiment, the serine protease variant of the present disclosure may include substitution of the amino acid corresponding to position 207 based on the amino acid sequence set forth in SEQ ID NO: 69. The variant may have 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with SEQ ID NO: 69. For example, the variant may include an amino acid sequence in which an amino acid at a position corresponding to the 12th amino acid of SEQ ID NO: 51 is substituted with another amino acid and has 70% or more sequence identity with SEQ ID NO: 51. As an example, the serine protease variant may further include substitution of the amino acid corresponding to position 311 based on the amino acid sequence set forth in SEQ ID NO: 69.

In an embodiment, the serine protease variant of the present disclosure may include substitution of the amino acid corresponding to position 203 based on the amino acid sequence set forth in SEQ ID NO: 70. The variant may have 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with SEQ ID NO: 70. For example, the variant may include an amino acid sequence in which an amino acid at a position corresponding to the 12th amino acid of SEQ ID NO: 52 is substituted with another amino acid and has 70% or more sequence identity with SEQ ID NO: 52. As an example, the serine protease variant may further include substitution of the amino acid corresponding to position 303 based on the amino acid sequence set forth in SEQ ID NO: 70.

In an embodiment, the serine protease variant of the present disclosure may include substitution of the amino acid corresponding to position 201 based on the amino acid sequence set forth in SEQ ID NO: 71. The variant may have 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with SEQ ID NO: 71. For example, the variant may include an amino acid sequence in which an amino acid at a position corresponding to the 12th amino acid of SEQ ID NO: 53 is substituted with another amino acid and has 70% or more sequence identity with SEQ ID NO: 53. As an example, the serine protease variant may further include substitution of the amino acid corresponding to position 304 based on the amino acid sequence set forth in SEQ ID NO: 71.

In an embodiment, the serine protease variant of the present disclosure may include substitution of the amino acid corresponding to position 201 based on the amino acid sequence set forth in SEQ ID NO: 72. The variant may have 60% or more, for example, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more homology or identity with SEQ ID NO: 72. For example, the variant may include an amino acid sequence in which an amino acid at a position corresponding to the 12th amino acid of SEQ ID NO: 54 is substituted with another amino acid and has 70% or more sequence identity with SEQ ID NO: 54. As an example, the serine protease variant may further include substitution of the amino acid corresponding to position 304 based on the amino acid sequence set forth in SEQ ID NO: 72.

However, the serine protease variant of the present disclosure is not limited thereto.

As used herein, the term "corresponding to" refers to an amino acid residue at a recited position in a protein or polypeptide, or an amino acid residue, which is similar, identical or homologous to that recited in a protein or polypeptide. Identifying the amino acid at the corresponding position may be determining the specific amino acid of a sequence that refers to the specific sequence. As used herein, the term "corresponding region" generally refers to a similar or corresponding position in a related protein or a reference protein. For example, any amino acid sequence may be aligned with SEQ ID NO: 31, and based on this, each amino acid residue of the amino acid sequence may be numbered with reference to the numerical position of the amino acid residue corresponding to the amino acid residue of SEQ ID NO: 31. For example, a sequence alignment algorithm such as that described in the present disclosure may identify the position of an amino acid or a position at which modifications, such as substitutions, insertions, or deletions, occur compared to a query sequence (also referred to as a "reference sequence").

For such alignment, the Needleman-Wunsch algorithm (Needleman and Wunsch, 1970, *J. Mol. Biol.* 48:443-453), the Needle program of the EMBOSS package (The European Molecular Biology Open Software Suite, Rice et al., 2000, *Trends Genet.* 16:276-277), and the like may be used, but the program for alignment is not limited thereto. The corresponding amino acid residues may be identified through multiple sequence alignment. Examples of multiple sequence alignment programs known in the art include programs such as MUSCLE (multiple sequence comparison by log-expectation; version 3.5 or higher; Edgar, 2004, *Nucleic Acids Research* 32:1792-1797) and MAFFT (version 6.857 or higher; Katoh and Kuma, 2002, *Nucleic Acids Research* 30:3059-3066; Katoh et al., 2005, *Nucleic Acids Research* 33:511-518; Katoh and Toh, 2007, Bioinformatics 23:372-374; Katoh et al., 2009, *Methods in Molecular Biology* 537:39-64; Katoh and Toh, 2010, *Bioinformatics* 26:1899-1900) and EMBOSS EMMA using ClustalW (1.83 or higher; Thompson et al., 1994, *Nucleic Acids Research* 22:4673-4680), and the basic parameters of each of the programs may be used, but the program is not limited thereto.

Another aspect of the present disclosure provides a polynucleotide encoding the serine protease variant.

As used herein, the term "polynucleotide" refers to a polymer of nucleotides in which nucleotide monomers are connected with one another in a long chain shape by covalent bonds, and a DNA or RNA strand having a certain length or longer, and more specifically, a polynucleotide fragment encoding the variant.

The polynucleotide encoding the serine protease variant of the present disclosure may include any polynucleotide sequence encoding the serine protease variant having an enhanced activity according to the present disclosure without limitation. In an embodiment, a gene encoding a wild-type serine protease in the present disclosure may be derived from a microorganism of the genus *Thermobifida*, the genus *Nocardiopsis*, the genus *Actinorugispora*, or the genus *Spinactinospora*, specifically, may be derived from *Thermobifida fusca*, *Thermobifida cellulosilytica*, *Thermobifida halotolerans*, *Achnorugispora endophytica*, *Spinachnospora alkalitolerans*, *Nocardiopsis composta*, or *Nocardiopsis potens*, but is not limited thereto.

The polynucleotide of the present disclosure may include various modifications made in a coding region in the amino acid sequence of the polypeptide within a range not changing the amino acid sequence, due to codon degeneracy or in consideration of codons preferred by a living organism in which the polypeptide is to be expressed. Specifically, any polynucleotide sequence encoding the variant in which the amino acids at positions corresponding to the 12th amino acid and/or 116th amino acid from the N-terminus of the amino acid sequence of any one selected from SEQ ID NOS: 31 and 49 to 54 are substituted with other amino acids may be included without limitation.

For example, the polynucleotide of the present disclosure may be a polynucleotide sequence encoding the variant of the present disclosure, specifically, a polypeptide consisting of the amino acid sequence set forth in any one selected from SEQ ID NOS: 32 to 39 and 55 to 66 or a polypeptide having a homology thereto, but is not limited thereto.

In an embodiment, the polynucleotide sequence encoding a polypeptide consisting of the amino acid sequence set forth in any one selected from SEQ ID NOS: 32 to 39 may consist of a polynucleotide sequence set forth in any one selected from SEQ ID NOS: 41 to 48, but is not limited thereto.

As described above, the serine protease variant of the present disclosure includes a variant in which amino acids at positions corresponding to 12 and/or 116 of the sequence are substituted in a polypeptide including the amino acid sequence of any one of SEQ ID NOS: 31 and 49 to 54, it is thus obvious that a polynucleotide sequence encoding such a serine protease variant is also included in the scope of the present disclosure.

As an example, in SEQ ID NO: 2 and SEQ ID NO: 40, a variant in which the amino acids at positions corresponding to 12 and/or 116 of SEQ ID NO: 31 (the 163rd amino acid and/or 267th amino acid of SEQ ID NO: 2 and the 193rd amino acid and/or 297th amino acid of SEQ ID NO: 40) are substituted is also included in the scope of the serine protease of the present disclosure, and thus a polynucleotide sequence encoding this is also included in the scope of the present disclosure. For example, the polynucleotide sequence encoding the serine protease variant may be one encoding an amino acid sequence set forth in any one selected from SEQ ID NOS: 3 to 10, specifically, one consisting of a polynucleotide sequence set forth in any one selected from SEQ ID NOS: 23 to 30, but is not limited thereto.

Additionally, any sequence encoding a protein having an activity of the variant in which the amino acids at positions corresponding to the 12th amino acid and/or 116th amino acid from the N-terminus of any one selected from SEQ ID NOS: 31 and 49 to 54 are substituted with other amino acids by hybridizing with a probe that may be prepared from known gene sequences, for example, sequences complementary to all or part of the nucleotide sequence under stringent conditions, may be included without limitation.

The term "stringent conditions" refers to conditions which allow specific hybridization between polynucleotides. Such conditions are disclosed in detail in known literatures. For example, the stringent conditions may include a condition for performing hybridization between genes having a high homology, 40% or more, specifically 90% or more, more specifically 95% or more, still more specifically 97% or more, particularly specifically 99% or more homology while not performing hybridization between genes having a homology lower than these homologies, or a condition for performing washing once, specifically twice or three times, under conventional washing conditions for southern hybridization of 60° C., 1×SSC, and 0.1% SDS, specifically at a salt concentration and a temperature of 60° C., 0.1×SSC, 0.1% SDS, more specifically 68° C., 0.1×SSC, and 0.1% SDS. However, stringent conditions are not limited thereto, but may be appropriately adjusted by those skilled in the art according to the purpose thereof.

Hybridization requires that two polynucleotides have complementary sequences, although bases may mismatch depending on the stringency of hybridization. The term "complementary" is used to describe the relationship between nucleotide bases which are capable of hybridizing with each other. For example, in the case of DNA, adenosine is complementary to thymine and cytosine is complementary to guanine. Thus, the present disclosure may include not only a substantially similar polynucleotide sequence but also an isolated polynucleotide fragment complementary to the entire sequence.

Specifically, the polynucleotide having homology may be detected using the above-described hybridization conditions including a hybridization process at a Tm value of 55° C. Additionally, the Tm value may be 60° C., 63° C., or 65° C., but is not limited thereto, and may be appropriately adjusted by those skilled in the art according to the purpose thereof.

An appropriate degree of stringency for hybridization of polynucleotides may depend on lengths of the polynucleotides and a degree of complementarity and the parameters are well known in the art.

Still another aspect of the present disclosure provides a vector including a polynucleotide encoding the serine protease variant of the present disclosure.

As used herein, the term "vector" refers to a DNA construct containing a nucleotide sequence of a target protein-encoding polynucleotide operably linked to a suitable control sequence so as to be able to express the target protein in a suitable host cell. The control sequence may include a promoter capable of initiating transcription, any operator sequence for regulating the transcription, a sequence encoding a suitable mRNA ribosome binding site, and a sequence for regulating termination of transcription and translation. Once transformed into a suitable host cell, the vector may replicate or function regardless of the host genome, or may integrate into genome thereof.

As used herein, the term "operably linked" refers to that a polynucleotide sequence encoding the target protein of the present disclosure is functionally linked to a promoter sequence which initiates and mediates transcription of the polynucleotide. An operable linkage may be prepared by a genetic recombination technique known in the art, and site-specific DNA cleavage and ligation may be prepared using a restriction enzyme, a ligase, and the like known in the art, but is not limited thereto.

The vector used in the present disclosure is not particularly limited, but any vector known in the art may be used. Examples of conventional vectors may include plasmids, cosmids, viruses and bacteriophages in a natural or recombinant state. For example, pWE15, M13, MBL3, MBL4, IXII, ASHII, APII, t10, t11, Charon4A, and Charon21A may be used as a phage vector or cosmid vector, and those based on pBR, pUC, pBluescriptII, pGEM, pTZ, pCL, pET, and pUB110 may be used as a plasmid vector. Specifically, pDZ, pACYC177, pACYC184, pCL, pECCG117, pUC19, pBR322, pMW118, pCC1BAC, and pSM704 vectors may be used. The vector that can be used in the present disclosure is not particularly limited, but any known expression vector may be used.

In an embodiment, the polynucleotide encoding the target variant in a chromosome may be replaced with a mutated polynucleotide using a vector for chromosomal insertion into cells. The insertion of the polynucleotide into the chromosome may be performed by any method known in the art, for example, homologous recombination, but is not limited thereto. The vector may further include a selection marker to confirm chromosomal insertion. The selection marker is used to select cells transformed with the vector, that is, to confirm whether a target nucleic acid molecule is inserted, and examples of the selection marker may include markers providing selectable phenotypes, such as drug resistance, auxotrophy, resistance to cytotoxic agents, or expression of surface mutant polypeptides. In an environment where a selective agent is treated, only cells expressing the selection marker can survive or show different phenotypes, and thus the transformed cells can be selected.

Still another aspect of the present disclosure provides a host cell including one or more of the serine protease variant of the present disclosure; a polynucleotide encoding the variant; or a vector including the polynucleotide.

The host cell may be, specifically, a microorganism.

A microorganism including one or more of the serine protease variant, a polynucleotide encoding the variant, or a vector including the polynucleotide may be, specifically, a microorganism prepared by transformation with a vector including a polynucleotide encoding a variant, but is not limited thereto.

The microorganism may be a microorganism expressing a serine protease variant.

As used herein, the term "to be expressed/being expressed/expressing" a protein refers to a modified state so that a target protein is introduced into a microorganism or expressed in a microorganism. In view of the objects of the present disclosure, the "target protein" may be the above-described serine protease variant.

Specifically, the term "introduction of a protein" may refer to exhibiting an activity of a particular protein in a microorganism which originally does not possess the protein or exhibiting an enhanced activity of the protein compared to the endogenous activity of the protein or the activity before modification. For example, the introduction of a protein may be the introduction of a polynucleotide encoding a particular protein into the chromosome of a microorganism or the introduction of a vector including the polynucleotide encoding the particular protein into a microorganism, thereby exhibiting the activity of the protein.

The microorganism may be a recombinant microorganism. The recombination may be achieved by genetic modification such as transformation.

As used herein, the term "transformation" refers to a process of introducing a vector including a polynucleotide encoding a target protein into a host cell in such a way that the protein encoded by the polynucleotide is expressed in the host cell. Regardless of whether the transformed polynucleotide is in a form inserted into the chromosome of a host cell or in a form located outside the chromosome, the transformed polynucleotides in both forms are within the scope of the present disclosure, as long as the transformed polynucleotide is expressed in the host cell. In addition, the polynucleotide includes DNA and RNA that encode the target protein. The polynucleotide may be introduced into a host cell in any form as long as the polynucleotide is introduced into the host cell and is expressed therein. For example, the polynucleotide may be introduced into a host cell in the form of an expression cassette, which is a gene construct including all of the essential elements required for self-replication. The expression cassette may generally include a promoter operably linked to the polynucleotide, a transcription termination signal, a ribosome binding site, and a translation termination signal. The expression cassette may be in the form of a self-replicable expression vector. Additionally, the polynucleotide may be introduced into a host cell in its original form and operably linked to a sequence required for the expression in the host cell, but is not limited thereto. Methods for the transformation include any method used to introduce a polynucleotide into cells and may be performed by suitable standard techniques known in the art. For example, the transformation methods include electroporation, calcium phosphate (Ca(H$_2$PO$_4$)$_2$, CaHPO$_4$, or Ca$_3$(PO$_4$)$_2$) precipitation, calcium chloride (CaCl$_2$) precipitation, microinjection, a polyethylene glycol (PEG) method, a DEAE-dextran method, a cationic liposome method, natural competence (for example, see Perry and Kuramitsu, 1981, *Infect. Immun.* 32:1295-1297]), and a lithium acetate-DMSO method, but is not limited thereto.

The recombinant microorganism may be a microorganism in which the activity of the serine protease of the present disclosure is enhanced.

The "enhancement of activity" may refer to that the activity of a particular protein possessed by a microorganism is enhanced compared to the endogenous activity or the activity before modification. The term "endogenous activity" may refer to an activity of a particular protein possessed by a parent strain of a microorganism before transformation when the microorganism is transformed by genetic mutation caused by a natural or artificial factor.

Specifically, the enhancement of the activity of the protein variant in the present disclosure may be achieved by one or more methods including a method of increasing the intracellular copy number of a gene encoding the protein variant, a method of introducing a mutation into an expression control sequence of the gene encoding the protein variant, a method of replacing the expression control sequence of the gene encoding the protein variant with a sequence having a stronger activity, a method of replacing a chromosomal gene encoding a wild-type protein having the serine protease activity with a gene encoding the protein variant, and a method of further introducing a mutation into the gene encoding the protein variant to enhance the activity of the protein variant, but is not limited thereto.

Next, the modification of the expression control sequence to increase the expression of a polynucleotide may be performed by inducing a mutation in the nucleic acid sequence by deletion, insertion, non-conservative substitution, conservative substitution, or a combination thereof to further enhance the activity of the expression control sequence, or by replacing the nucleic acid sequence with a nucleic acid sequence having a stronger activity, but is not limited thereto. The expression control sequence may include a promoter, an operator sequence, a ribosome-binding site encoding sequence, sequences for regulating transcription and translation, and the like, but is not limited thereto.

A strong promoter, instead of the endogenous promoter, may be linked to the upper portion of the polynucleotide expression unit, but the promoter is not limited thereto. Examples of the known strong promoter may include cj1 to cj7 promoters (U.S. Pat. No. 7,662,943 B2), a lac promoter, a trp promoter, a trc promoter, a tac promoter, a lambda phage PR promoter, a P$_L$ promoter, a tet promoter, a gapA promoter, an SPL7 promoter, an SPL13 (sm3) promoter (U.S. Ser. No. 10/584,338 B2), an O2 promoter (U.S. Ser. No. 10/273,491 B2), a tkt promoter, a yccA promoter, and the like, but is not limited thereto.

In addition, the modification of the polynucleotide sequence on the chromosome may be performed by inducing a mutation in the expression control sequence by deletion, insertion, non-conservative substitution, or conservative substitution of a nucleic acid sequence, or a combination thereof to further enhance the activity of the polynucleotide sequence, or by replacing the sequence with a polynucleotide sequence modified to have a stronger activity, but is not limited thereto.

Generally, such introduction and enhancement of a protein activity may increase the activity or concentration of the corresponding protein by a minimum of 1%, 10%, 25%, 50%, 75%, 100%, 150%, 200%, 300%, 400%, or 500% to a maximum of 1,000% or 2,000% based on the activity or concentration in a wild-type or non-modified microorganism strain, but is not limited thereto.

The host cell or microorganism according to the present disclosure may be any microorganism expressing the serine protease variant by including the polynucleotide of the present disclosure or the vector of the present disclosure. Specifically, examples of the host cell or microorganism may include strains of microorganisms of the genus *Escherichia*, the genus *Serratia*, the genus *Erwinia*, the genus *Enterobacteria*, the genus *Providencia*, the genus *Salmonella*, the genus *Streptomyces*, the genus *Pseudomonas*, the genus *Brevibacterium*, the genus *Corynebacterium*, or the genus *Bacillus*, specifically, the host cell or microorganism may be strains of *Bacillus subtilis*, *Bacillus licheniformis*, *Bacillus amyloliquefaciens*, *Bacillus velezensis*, *Escherichia*

*coli, Corynebacterium glutamicum,* or *Aspergillus oryzae,* and more specifically, the host cell or microorganism may be *Bacillus subtilis,* but is not limited thereto.

Still another aspect of the present disclosure provides a method of preparing the serine protease variant of the present disclosure.

The method of preparing the variant of the present disclosure may include a step of culturing a microorganism including one or more of the serine protease variant of the present disclosure; a polynucleotide encoding the variant; or a vector including the polynucleotide.

As used herein, the term "culture" refers to growing the host cell in an appropriately regulated environmental condition. The culture process in the present disclosure may be conducted using a proper medium under proper culture conditions known in the art. Such a culture process may be easily adjusted and used by those skilled in the art depending on the selected strain. Specifically, the culture may be batch culture, continuous culture, and fed-batch culture, but is not limited thereto.

As used herein, the term "medium" refers to a material in which nutrients required for culturing the host cell are mixed as main ingredients, and supplies nutrients and growth factors, including water, which are essential for survival and growth. Specifically, as the medium and other culture conditions used for culturing the host cell of the present disclosure, any medium may be used without particular limitation as long as it is a conventional medium used for culturing host cells, but the host cell of the present disclosure may be cultured in a conventional medium containing proper carbon sources, nitrogen sources, phosphorus sources, inorganic compounds, amino acids and/or vitamins, and the like under aerobic conditions while controlling the temperature, pH, and the like.

In an embodiment, the method of preparing the variant of the present disclosure may further include a step of recovering the variant of the present disclosure expressed in the culture step.

In another embodiment, the variant expressed in the culture step may be recovered using a method known in the art to which the present invention pertains. For example, the variant may be recovered from the nutrient medium by conventional procedures including, but not limited to, collection, centrifugation, filtration, extraction, spray-drying, evaporation or precipitation.

The recovery method may be to collect variants using a suitable method known in the art depending on the culture method of the host cell of the present disclosure, for example, a batch, continuous, or fed-batch culture method. For example, centrifugation, filtration, treatment with a crystallized protein precipitating agent (salting-out method), extraction, sonication, ultrafiltration, dialysis, various kinds of chromatography such as molecular sieve chromatography (gel filtration), adsorption chromatography, ion exchange chromatography, and affinity chromatography, HPLC, and a combination of these methods may be used, and variants may be recovered from media or host cells using suitable methods known in the art.

In another embodiment, the variant expressed by the host cell in the culture step may not be recovered. In the embodiment, the host cell itself expressing the variant may be used as a source of the variant.

Still another aspect of the present disclosure provides a feed composition including one or more of the serine protease variant of the present disclosure or a microorganism expressing the serine protease variant.

The serine protease variant to be included in the feed composition of the present disclosure may be included in the feed composition in such a manner that the microorganism expressing the serine protease variant itself is included or may be in a form isolated from the microorganism expressing the serine protease variant and purified, but is not limited thereto.

As used herein, the term "feed composition" refers to any natural or artificial diet, one meal or the like or an ingredient of the one meal for animals to eat, intake, and digest or being suitable therefor, and the feed may be prepared in various forms known in the art.

The feed composition may be a feed additive.

The kind of the feed is not particularly limited, and feed commonly used in the art may be used. Non-limiting examples of the feed may include: vegetable feeds such as grains, roots/fruits, food processing by-products, algae, fibers, pharmaceutical by-products, oils and fats, starches, gourds, and grain by-products; and animal feeds such as proteins, inorganic substances, oils and fats, minerals, single-cell proteins, animal planktons, or foods. These feeds may be used singly or in combination of two or more thereof.

The feed composition of the present disclosure may further include one or more selected from: organic acids such as citric acid, fumaric acid, adipic acid, lactic acid, and malic acid; phosphates such as sodium phosphate, potassium phosphate, acid pyrophosphate, and polyphosphate (polymerized phosphate); or natural antioxidants such as polyphenol, catechin, alpha-tocopherol, rosemary extract, vitamin C, green tea extract, licorice root extract, chitosan, tannic acid, and phytic acid.

The feed composition of the present disclosure may further include one or more selected from: adjuvant ingredients such as amino acids, minerals, vitamins, antibiotics, antibacterial substances, antioxidants, antifungal enzymes, and microbial preparations in other probiotic forms; grains, for example, pulverized or crushed wheat, oat, barley, corn, and rice; vegetable protein feeds including rape, beans, and sunflowers as a main ingredient; animal protein feeds, for example, powders of blood, meat, bone, and fish; sugar and dairy products, for example, dry ingredients formed of various kinds of dry milk and whey powder; lipids, for example, main ingredients such as animal fats and vegetable oils arbitrarily liquefied by heating; and additives such as nutritional supplements, digestion and absorption promoters, growth promoters, and prophylactic agents.

The feed composition of the present disclosure may be in the form of a dry or liquid preparation and may further include an excipient for feed. The excipient for feed may be, for example, zeolite, corn flour, and rice bran, but is not limited thereto.

The feed composition of the present disclosure may further include an enzyme preparation in addition to the serine protease variant. For example, the feed composition may further include one or more selected from a lipid-degrading enzyme such as lipase, phytase that degrades phytic acid into a phosphate and inositol phosphate, amylase that is an enzyme catalyzing the hydrolysis of $\alpha$-1,4-glycoside bonds included in starch, glycogen and the like, phosphatase that is an enzyme catalyzing the hydrolysis of organophosphate esters, maltase that catalyzes maltose into two glucose molecules, and a converting enzyme that catalyzes the hydrolysis of sucrose into a glucose-fructose mixture. However, the feed composition is not limited thereto.

The feed composition of the present disclosure may be administered to animals singly or in combination with other feed additives included in an edible carrier. In addition, the feed composition may be easily administered as a feed additive or top dressing by being directly mixed in a livestock feed or separately from the feed, or in a separate oral formulation or in combination with other ingredients. In addition, a daily dosage may be employed via once-daily dose or multiple-divided daily dose as commonly known in the art.

Examples of the animal to which the feed composition of the present disclosure is applied may include livestock such as beef cattle, dairy cattle, calves, pigs, piglets, sheep, goats, horses, rabbits, dogs, and cats; and poultry such as chicks, hens, domestic chickens, roosters, ducks, geese, turkeys, quails, and small birds, but the animal is not limited thereto.

The amount of the serine protease variant included in the feed composition of the present disclosure is not particularly limited and may be appropriately adjusted according to the purpose thereof. In an embodiment, the serine protease variant may be included in an appropriate amount for degrading a protein source substance while surviving in the digestive tract of livestock for a long period of time as commonly known in the art to which the present disclosure pertains, but the amount of the serine protease variant is not limited thereto.

Still another aspect of the present disclosure provides a food composition including one or more of the serine protease variant of the present disclosure or a microorganism expressing the serine protease variant. The serine protease can be used in a liquid or solid food composition. In addition, the food may be powders, pills, beverage, tea, or additives for general foods.

In an embodiment, the food may be a group of foods requiring a protease, such as dairy products, health functional foods for improving bowel movement and weight loss, and health functional foods for preventing hypertension.

In another embodiment, the serine protease variant may be included in various food compositions as a food solubilizer, food softening agent, and meat modifier. In various other embodiments, the serine protease variant may be added to baking mixes in a step for gluten network breakdown. Alternatively, the serine protease variant may be used to catalyze the hydrolysis of food proteins (for example, milk proteins). Alternatively, the serine protease variant may be included in various food compositions for the purpose of rendering, preparing flavoring agents, reducing bitterness, changing emulsifying properties, producing bioactive peptides, reducing allergy-causing antigens in proteins. However, this is only an illustrative embodiment and the uses of the serine protease variant are not limited thereto.

The amount of the serine protease variant in the food composition of the present disclosure may be appropriately adjusted by those skilled in the art according to the purpose thereof.

Still another aspect of the present disclosure provides a detergent composition including one or more of the serine protease variant of the present disclosure or a microorganism expressing the serine protease variant.

The detergent composition of the present disclosure may be in the form of first and second aqueous detergent compositions, non-aqueous liquid detergent compositions, cast solids, granules, particles, compressed tablets, gels, pastes, or slurries. The detergent composition may be used to remove stubborn food stains, food residue films, and other small amounts of food compositions.

The detergent composition according to the present disclosure may be provided in the form of a detergent composition for cleaning hard surfaces, a detergent composition for cleaning fabrics, a detergent composition for dishwashing, a detergent composition for oral cleaning, a detergent for cleaning dentures, or a contact lens cleaning solution. However, the detergent composition is not limited thereto.

Still another aspect of the present disclosure provides a pharmaceutical composition including one or more of the serine protease variant of the present disclosure or a microorganism expressing the serine protease variant.

The pharmaceutical composition of the present disclosure may be used as a pharmaceutical composition for digestive enzymes to improve digestive diseases, digestive disorders, and abnormalities after digestive surgery, a thrombolytic or antithrombotic composition directly applied to blood clots to dissolve fibrin, an anti-inflammatory drug acting as an in vivo defense system to remove inflammatory substances or necrotic tissue, or an anti-inflammatory drug to alleviate edema after surgery or wounds.

The pharmaceutical composition may further include a pharmaceutically acceptable or nutritionally acceptable carrier, excipient, diluent, or accessory ingredient according to the methods or purposes of use. The carrier, excipient, or diluent may include one or more selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate and mineral oils, dextrin, calcium carbonate, propylene glycol, liquid paraffin, and physiological saline solution, but is not limited thereto.

The serine protease variant of the present disclosure or the microorganism expressing the serine protease variant may also be used for the purpose of producing cosmetics, processing leather, preparing pharmaceuticals, preparing diagnostic agents, managing wastes, and preparing chemicals for academic research, in addition to the above-described uses. However, the uses are exemplarily described and the serine protease variant may also be used for any other purposes of denaturing, degrading, or removing proteinaceous substances known in the art.

EXAMPLES

Hereinafter, the present disclosure will be described in more detail with reference to the following Examples and Experimental Examples. However, these Examples and Experimental Examples are for illustrative purposes only and are not intended to limit the scope of the present disclosure.

Example 1. Selection of Serine Protease Variant Derived from *Thermobfida fusca*

Example 1-1: Preparation of *Thermobifida fusca*-Derived Serine Protease Library A random mutation was introduced into a gene encoding an amino acid (SEQ ID NO: 31) corresponding to a mature region of a *Thermobifida fusca*-derived serine protease by error-prone PCR. The error-prone PCR was performed using a Diversify™ PCR Random Mutagenesis Kit (Clontech, Cat No. 630703), and the PCR conditions are as described in Table 1. It was confirmed that the mutation was introduced at a frequency of 6.2 mutations/kb under the conditions below.

TABLE 1

| Composition | Amount | Remarks |
|---|---|---|
| Template DNA | 0.5 ng | SEQ ID NO: 1 |
| Primer_forward | 5 µM | SEQ ID NO: 11 |
| Primer_reverse | 5 µM | SEQ ID NO: 12 |
| 10X Titanium Taq buffer | 5 µL | |
| MnSO$_4$ | 640 µM | |
| dGTP | 40 µM | |
| 50X Diversify dNTP mix | 1 µL | |
| 50X dNTP mix | 1 µL | |
| Titanium Taq Polymerase | 1 µL | |
| Total | 50 µL | Adjust to 50 µL with DW |
| | PCR Conditions | |
| I. 94° C. | 30 sec | Repeat 50 cycles of II |
| II. 94° C. | 30 sec | and III |
| III. 68° C. | 1 min | |
| IV. 68° C. | 1 min | |
| V. 4° C. | ∞ | |

PCR fragments obtained through the process were ligated to vectors amplified using primers presented in Table 2 using an In-FusionR HD cloning kit (Clontech) and transformed into DH5a cells to obtain colonies. The plasmids in the obtained colonies were purified to obtain libraries having a size of about 5×10$^4$.

TABLE 2

| | |
|---|---|
| Template DNA (pBE-S-TAP) | SEQ ID NO: 1 |
| Primer_forward | SEQ ID NO: 13 |
| Primer_reverse | SEQ ID NO: 14 |

Example 1-2: Screening of *Thermobifida fusca*-Derived Serine Protease Library A *Bacillus subtilis* LB700 strain, which easily released proteins, was transformed with the protease library prepared in Example 1-1 and screened. The screening was performed by a two-stage process. In a first stage, the *Bacillus subtilis* strain transformed with the library was plated on a 2% skim milk plate, and the desired colonies were selected based on the formed halo size. The transformation of *Bacillus subtilis* was performed according to the Groningen method, and the composition of the skim milk plate used in the screening is as presented in Table 3.

TABLE 3

| Composition | Amount | Remarks |
|---|---|---|
| M9 minimal salts | 11.28 g | BD, Cat. No. 248510 |
| Agar | 20 g | |
| Skim milk | 20 g | BD, Cat. No. 232100 |
| 50% Glucose | 20 g | |
| 1M MgSO$_4$ | 2 mM | |
| 1M CaCl$_2$ | 0.1 mM | |
| Kanamycin | 50 µg/mL | |

(per 1 L)

A second stage relates to a method of re-selecting the colonies, which were selected in the first stage, by azocasein color development. A Brain Heart Infusion (BHI, bd, Cat. No. 53286) liquid medium containing a kanamycin antibiotic was placed in a 96-deep-well plate, and the colonies selected in the first stage were inoculated thereinto, followed by culturing at 37° C. for 20 to 24 hours. After the culture, a supernatant including an enzyme was obtained by centrifugation, and the supernatant was mixed with an equal amount of 2% (w/v) azocasein as a substrate, followed by a reaction at 37° C. for 1 hour. The reaction was terminated by adding a 3-fold volume of 10% trichloro acetic acid (TCA) to the enzyme reaction solution, and coagulated proteins were removed by centrifugation. The color development reaction was performed by mixing the resultant with an equal amount of NaOH, and then the absorbance was measured at 440 nm to compare the degree of color development. Through this process, colonies having an increase in absorbance by 150% or more compared to that of the wild-type serine protease were selected.

Example 2. Preparation of Selected Variant and Evaluation of Activity

Example 2-1: Preparation of Variant

As a result of analyzing the sequences of variants selected through screening, it was confirmed that the 12th amino acid (phenylalanine, Phe) and the 116th amino acid (asparagine, Asn) of SEQ ID NO: 31 were substituted with tyrosine (Tyr) and aspartate (Asp), respectively. In FIG. 1, the positions of the mutations are indicated based on an amino acid sequence set forth in SEQ ID NO: 2. After the two selected variants (F12 and N116) were re-introduced into pBE-S-TAP plasmid in the form of single mutation by site directed mutagenesis, the activities of the strains with a double mutation and a single mutation were compared with the activity of the wild-type strain. Primers used to prepare the variants are as presented in Table 4.

TABLE 4

| | |
|---|---|
| TAP_F12Y_F | SEQ ID NO: 15 |
| TAP_F12Y_R | SEQ ID NO: 16 |
| TAP_N116D_F | SEQ ID NO: 17 |
| TAP_N116D_R | SEQ ID NO: 18 |

Example 2-2: Evaluation of Activity

After the *Bacillus subtilis* LB700 strain was transformed with the prepared plasmid, the activity evaluation of the transformant was performed using a N-succinyl-Ala-Ala-Pro-Phe-p-nitroanilide peptide (Sigma, Cat. No. S7388, hereinafter referred to as Suc-AAPF-pNA) as a substrate. The transformed *Bacillus subtilis* strain was inoculated into the Brain Heart Infusion (BHI, bd, Cat. No. 53286) liquid medium containing a kanamycin antibiotic and cultured at 37° C. for 20 to 24 hours, and a portion of the culture solution except for the cells was mixed with a 25 mM Tris-HCl (pH 7.5) buffer and a 1 mM Suc-AAPF-pNA, followed by a reaction at 37° C. for 30 minutes. The absorbance of the reaction solution was measured at 410 nm. An extinction coefficient of para-nitroaniline produced by an enzyme known in a literature was 8,800 M$^{-1}$cm$^{-1}$ at 410 nm, and the unit of the enzyme was calculated based thereon (Barrett, A. J., Cathepsin G. *Methods Enzymol.,* 80, Pt. C, 561-565, (1981)). The measured activities are as presented in Table 5.

TABLE 5

| | Enzyme activity (unit/mL) |
|---|---|
| Wild type | 16.3 |
| F12Y | 34.0 |
| F12YN116D | 63.8 |

As a result of the measurement, it was confirmed that the activities of the F12Y and F12YN116D variants were increased at pH 7.5 and 37° C. by about 2.1-fold and 3.9-fold, respectively, compared to that of the wild type.

Example 2-3: Evaluation of Thermal Stability

An experiment described below was performed to confirm the influence of variant introduction on thermal stability.

Specifically, the enzyme activities of samples the same as those used in Example 2-2 for the evaluation of activity were measured after placing the samples at room temperature, at 70° C., at 80° C., and at 90° C. for 5 minutes, respectively. The measured activities are as presented in Table 6.

TABLE 6

| | Enzyme activity (unit/mL) | | | |
|---|---|---|---|---|
| Heat treatment conditions | RT, 5 min | 70° C., 5 min | 80° C., 5 min | 90° C., 5 min |
| Wild type | 16.3 | 15.9 | 10.6 | 0.3 |
| F12Y | 34.0 | 34.7 | 22.8 | 0.1 |
| F12YN116D | 63.8 | 63.3 | 41.7 | 0.1 |

As a result of the measurement, it was confirmed that the F12Y and F12YN116D variants maintained enzyme activities higher by about 2-fold and 4-fold compared to that of the wild type even at 80° C., respectively. Through this, it was confirmed that a high activity of the serine protease variant of the present disclosure was maintained even at a high temperature, and thus the serine protease variant can be effectively used in industry.

Example 3. Preparation and Selection of Saturation Mutagenesis Library

Example 3-1. Preparation of Saturation Mutagenesis Library of F12 and N116 Residues In order to confirm the influence of substitution of the residues F12 and N116 (namely, previously selected variants) with residues other than tyrosine and aspartate on the activities, saturation mutagenesis libraries were prepared for the two residues.

Two PCR fragments were obtained using the pBE-S-TAP plasmid as a template and the primer pairs of SEQ ID NOS: 11 and 12 and SEQ ID NOS: 13 and 14, respectively. The fragments were ligated using the In-Fusion HD cloning kit and then transformed into DH5a cells to thereby obtain colonies. The plasmids in the obtained colonies were purified to obtain libraries having a size of about 4×10³.

TABLE 7

| Template DNA (pBE-S-TAP) | SEQ ID NO: 1 |
|---|---|
| Saturation mutagenesis_F_1 | SEQ ID NO: 19 |
| Saturation mutagenesis_R_1 | SEQ ID NO: 20 |
| Saturation mutagenesis_F_2 | SEQ ID NO: 21 |
| Saturation mutagenesis_R_2 | SEQ ID NO: 22 |

Example 3-2: Screening of Saturation Mutagenesis Library and Evaluation of Activity The saturation mutagenesis libraries prepared in Example 3-1 were subjected to screening in the same manner as in Example 1-2. Variants having an activity the same as or increased compared to that of the F12YN116D variant were selected through screening, and sequence analysis and the evaluation of activity was performed on these variants by using Suc-AAPF-pNA as a substrate.

TABLE 8

| | Enzyme activity (unit/mL) |
|---|---|
| Wild type | 23.52 |
| F12YN116D | 65 |
| F12YN116S | 77.35 |
| F12SN116D | 61.75 |
| F12SN116T | 117.65 |
| F12AN116G | 94.9 |
| F12A | 94.25 |
| F12R | 58.5 |

As a result, it was found that the activities of the F12 and N116 variants increased even when the residues were substituted with other amino acids such as F12S, F12A, F12R, N116S, N116T, and N116G in addition to tyrosine and aspartate confirmed in Example 2.

Example 3-3. Preparation of F12S Variant and Evaluation of Activity

After the variant (F12S) was re-introduced into pBE-S-TAP plasmid in the form of single mutation by site-directed mutagenesis, the activity of the variant was compared with the activity of the wild-type.

Activity evaluation was performed on the variant (F12S) using Suc-AAPF-pNA as a substrate.

TABLE 9

| | Enzyme activity (Unit/mL) |
|---|---|
| Wild type | 23.0 |
| F12S | 34.5 |

As a result of the measurement, it was confirmed that the activity of the F12S variant was increased by about 1.5-fold.

Example 4. Confirmation of Influence of Residues 12 and 116 of *Thermobifida fusca*-Derived Serine Protease-Like Protein

Example 4-1: Preparation of Wild Type and Variant

In order to examine whether amino acid residues corresponding to 12 and 116 of SEQ ID NO: 31 affect the increase in activity in other serine proteases having sequence homology to SEQ ID NO: 31, residues 12 and 116 of serine proteases having sequence homology of 87.2%, 81.8%, 81.3%, 73.8%, 69.9%, and 66.7%, respectively, were substituted with tyrosine (Y) and aspartate (D), and then the activities of the serine proteases were compared to that of the wild type. The origin and sequence information of each serine protease are as presented in Table 10.

TABLE 10

| Origin | SEQ ID NO: | Homology to SEQ ID NO: 31 (%) | Homology to SEQ ID NO: 54 (%) |
|---|---|---|---|
| *Thermobifida fusca* | SEQ ID NO: 31 | — | 66.7 |
| *Thermobifida cellulosilytica* | SEQ ID NO: 49 | 87.2 | 65.1 |
| *Thermobifida halotolerans* | SEQ ID NO: 50 | 81.8 | 61.3 |
| *Actinorugispora endophytica* | SEQ ID NO: 51 | 81.3 | 64 |
| *Spinactinospora alkalitolerans* | SEQ ID NO: 52 | 73.8 | 75.4 |
| *Nocardiopsis composta* | SEQ ID NO: 53 | 69.9 | 86.6 |
| *Nocardiopsis potens* | SEQ ID NO: 54 | 66.7 | — |

Residues 12 and 116 of the respective serine proteases were substituted with tyrosine (Y) and aspartate (D) to prepare variants of SEQ ID NOS: 55 to 66.

Example 4-2: Evaluation of Activity

The prepared plasmids were transformed and expressed in the *Bacillus subtilis* LB700 strain, and then the evaluation of activity was performed by the same method as the activity measuring method mentioned in Example 2-2. The measured activities are as presented in Table 11.

TABLE 11

| Origin | Variant | Activity (U/mL) |
|---|---|---|
| *Thermobifida cellulosilytica* | WT | 13.6 |
| | F12Y | 16.3 |
| | F12YN116D | 29.1 |
| *Thermobifida halotolerans* | WT | 4.0 |
| | F12Y | 6.3 |
| *Actinorugispora endophytica* | WT | 10.4 |
| | F12Y | 14.0 |
| *Spinactinospora alkalitolerans* | WT | 2.0 |
| | P12Y | 2.6 |
| *Nocardiopsis composta* | WT | 12.1 |
| | P12Y | 26.5 |
| *Nocardiopsis potens* | WT | 33.1 |
| | P12Y | 86.3 |

As a result of the measurement, it was confirmed that the activities of six kinds of proteins having sequence homology to the *Thermobifida fusca*-derived serine protease also increased when a mutation was introduced into residue 12 as in the *Thermobifida fusca*-derived serine protease.

From the facts, it has been confirmed that residues 12 and 116 are important residues for exhibiting the enzyme activity of serine protease, and the enzyme activity can be increased by substituting these residues with other amino acids as confirmed through SEQ ID NO: 31. Consequently, the serine protease variant of the present disclosure exhibiting increased enzyme activity can be effectively used in industry.

Based on the above description, it will be understood by those skilled in the art that the present disclosure may be implemented in a different specific form without changing the technical spirit or essential characteristics thereof. Therefore, it should be understood that the above-described embodiments are not limitative, but illustrative in all aspects. The scope of the present disclosure is defined by the appended claims rather than by the description preceding them, and all changes and modifications that fall within metes and bounds of the claims or equivalents of such metes and bounds are therefore intended to be embraced by the claims.

---

The invention claimed is:

1. A serine protease variant having at least 75% sequence identity with SEQ ID NO: 54 and comprising tyrosine (Y) at a position corresponding to position 12 of SEQ ID NO: 54.

2. The serine protease variant according to claim 1, wherein the variant further comprises a substitution of an amino acid corresponding to position 116 of SEQ ID NO: 54.

3. The serine protease variant according to claim 1 having at least 75% sequence identity to SEQ ID NO: 70, SEQ ID NO: 71, or SEQ ID NO: 72.

4. The serine protease variant according to claim 2, wherein the amino acid corresponding to position 116 is substituted with a hydrophilic amino acid, a nonpolar amino acid, or an acidic amino acid.

5. The serine protease variant according to claim 2, wherein the amino acid corresponding to position 116 is substituted with aspartate (D), serine(S), threonine (T), or glycine (G).

6. A composition comprising the serine protease variant according to claim 1.

7. A polynucleotide encoding a serine protease variant that comprises:
   (a) the amino acid sequence of SEQ ID NO: 52 except that the amino acid at position 12 of SEQ ID NO: 52 is substituted with tyrosine (Y),
   (b) the amino acid sequence of SEQ ID NO: 53 except that the amino acid at position 12 of SEQ ID NO: 53 is substituted with tyrosine (Y), or
   (c) the amino acid sequence of SEQ ID NO: 54 except that the amino acid at position 12 of SEQ ID NO: 54 is substituted with tyrosine (Y).

8. A vector comprising the polynucleotide according to claim 7.

9. A host cell comprising the serine protease variant according to claim 1.

10. A composition comprising a microorganism expressing the serine protease variant according to claim 1.

11. The serine protease variant according to claim 3, wherein the serine protease variant comprises tyrosine (Y) at a position corresponding to position 203 of SEQ ID NO: 70.

12. A composition comprising the serine protease variant according to claim 3.

13. A polynucleotide encoding a serine protease variant that comprises:
   (a) the amino acid sequence of SEQ ID NO: 70 except that the amino acid at position 203 of SEQ ID NO: 70 is substituted with tyrosine (Y),
   (b) the amino acid sequence of SEQ ID NO: 71 except that the amino acid at position 201 of SEQ ID NO: 71 is substituted with tyrosine (Y), or
   (c) the amino acid sequence of SEQ ID NO: 72 except that the amino acid at position 201 of SEQ ID NO: 72 is substituted with tyrosine (Y).

14. A vector comprising the polynucleotide according to claim 13.

15. A host cell comprising the serine protease variant according to claim 8.

16. A composition comprising a microorganism expressing the serine protease variant according to claim 3.

17. A host cell comprising the polynucleotide according to claim 7; or a vector comprising the polynucleotide.

18. A host cell comprising the polynucleotide according to claim 13; or a vector comprising the polynucleotide.

\* \* \* \* \*